(12) United States Patent
Stegh et al.

(10) Patent No.: US 7,595,158 B2
(45) Date of Patent: Sep. 29, 2009

(54) BCL2L12 POLYPEPTIDE ACTIVATORS AND INHIBITORS

(75) Inventors: Alex Stegh, Boston, MA (US); Hyung Gee Kim, Seoul (KR); Ronald A. Depinho, Brookline, MA (US); Lynda Chin, Brookline, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 268 days.

(21) Appl. No.: 11/259,640

(22) Filed: Oct. 25, 2005

(65) Prior Publication Data

US 2006/0252053 A1 Nov. 9, 2006

Related U.S. Application Data

(63) Continuation-in-part of application No. PCT/US2004/012591, filed on Apr. 23, 2004.

(60) Provisional application No. 60/465,573, filed on Apr. 25, 2003.

(51) Int. Cl.
   *C12Q 1/68* (2006.01)
(52) U.S. Cl. ............................. 435/6; 435/29; 530/350
(58) Field of Classification Search .................. None
   See application file for complete search history.

(56) References Cited

U.S. PATENT DOCUMENTS

| 4,683,195 A | 7/1987 | Mullis et al. |
| 5,580,859 A | 12/1996 | Felgner et al. |
| 5,589,466 A | 12/1996 | Felgner et al. |
| 6,248,904 B1 | 6/2001 | Zhang et al. |

FOREIGN PATENT DOCUMENTS

WO   WO 02/79419   10/2002

OTHER PUBLICATIONS

Richards (1997) Cell Mol. Life Sci. 53:790-802.*
GenBank® accession No. O14727, dated Sep. 19, 2006, 12 pages.
Boletta et al., "High Efficient Non-Viral Gene Delivery to the Rat Kidney by Novel Polycationic Vectors," *J. Am. Soc. Nephrol.*, 1996, 7(9):1728, Abstract No. A2409.
Fujita et al., "Caspase-9 processing by caspase-3 via a feedback amplification loop in vivo," *Cell Death Differ.*, 2001, 8:335-344.
Huhn et al., "Chromosomal Abnormalities in Glioblastoma Multiforme by Comparative Genomic Hybridization: Correlation with Radiation Treatment Outcome," *Clin. Cancer Res.*, 1999, 5:1435-1443.
Ishii et al., "Frequent Co-Alterations of *TP53, p16/CDKN2A, p14^{ARF}, PTEN* Tumor Suppressor Genes in Human Glioma Cell Lines," *Brain Pathology*, 1999, 9:469-479.
Jiang et al., "Distinctive Roles of PHAP Proteins and Prothymosin-α in a Death Regulatory Pathway," *Science*, 203, 299:223-226.
Kong et al., "Mechanisms of Differential Activation of Target Gene Promoters by p53 Hinge Domain Mutants with Impaired Apoptotic Function," *J. Biol. Chem.*, 2001, 276(35):32990-33000.
Mohapatra et al., "Genetic Analysis of Glioblastoma Multiforme Provides Evidence for Subgroups Within the Grade," *Genes Chromosomes Cancer*, 1998, 21:195-206.
Nagane et al., "Drug resistance of human glioblastoma cells conferred by a tumor-specific mutant epidermal growth factor receptor through modulation of Bcl-$X_L$ and caspase-3-like proteases," *Proc. Natl. Acad. Sci. USA*, 1998, 95:5724-5729.
Paddison et al., "Short hairpin RNAs (shRNAs) induce sequence-specific silencing in mammalian cells," *Genes Dev.*, 2002, 16:948-958.
Scorilas et al., "Molecular Cloning, Physical Mapping, and Expression Analysis of a Novel Gene, BCL2L12, Encoding a Proline-Rich Protein with a Highly Conserved BH2 Domain of the Bcl-2 Family," *Genomics*, 2001, 72:217-221.
Slee et al., "Ordering the Cytochrome c-initiated Caspase Cascade: Hierarchical Activation of Caspases-2, -3, -6, -7, -8, and -10 in a Caspase-9-dependent Manner," *J. Cell Biol.* 1999, 144(2):281-292.
St-Pierre et al., "Bioenergetic Analysis of Peroxisome Proliferator-activated Receptor γ Coactivators 1α and 1β (PGC-1α and PGC-1β) in Muscle Cells," *J. Biol. Chem.*, 2003, 278(29):26597-26603.
Templeton et al. "Improved DNA: liposome complexes for increased systemic delivery and gene expression," *Nature Biotechnology*, 1997, 15:647-652.
Thornberry et al., "A Combinatorial Approach Defines Specificities of Members of the Caspase Family and Granzyme B," *J. Biol. Chem.*, 1997, 272(29):17907-17911.
Weber et al., "Characterization of genomic alterations associated with glioma progression by comparative genomic hybridization," *Oncogene*, 1996, 13:983-994.
Yuan and Yankner, "Apoptosis in the nervous system," *Nature*, 2000, 407:802-809.
Waltereit and Weller, "The role of caspases 9 and 9-short (9S) in death ligand- and drug- induced apoptosis in human astrocytoma cells," *Molecular Brain Research*, 2002, 106:42-49.
Talieri et al., "Expression of BCL2L12, a new member of apoptosis-related genes, in breast tumors," *Thromb. Haemost.*, 2003, 89(6):1081-1088.
Scorilas et al., "The new member of apoptosis-related proteins, BCL2L12, is down regulated in aggressive breast tumors and in arrested human fibroblasts," *Proc. Am. Assoc. Cancer Res.*, 2002, 43:529, Abstract No. 2622.

* cited by examiner

*Primary Examiner*—James S Ketter
(74) *Attorney, Agent, or Firm*—Fish & Richardson P.C.

(57) ABSTRACT

The invention provides methods and materials related to Bcl2L12 polypeptides and the biological activities of Bcl2L12 polypeptides. For example, the invention provides methods and materials related to identifying activators and inhibitors of Bcl2L12 polypeptide activities such as the ability to block apoptosis and promote cell growth and transformation. The invention also provides methods and materials for treating mammals having cancer.

20 Claims, 13 Drawing Sheets

Figure 3

```
  1  MGRPAGLFPPLCPFLGFRPEACWERHMQIERAPSVPPFLRWAGYRPGPVR     hu Bcl2L12

51  RRGKVELIKFVRVQWRRPQVEWRRRWGPGAS                        hu Bcl2L12

85  MAGSEELGLREDTLRVLAAFLRRGEAAGSPVTPRRSPAQEEPTDFLSRL      hu Bcl2L12
  1  MAGSEELGLREDTLKVLTAFLKRGEVAGSPVTPRRSPAQEETTDFLSRL      mu Bcl2L12

136  RRCLPCSLGRGAAPSESPRPCSLRFCYGLEPGPATPDFYALVAQRLEQ       hu Bcl2L12
 51  RRCLPCPLGRGAPPTESSRPHFLRPCYGSEPGPASSEFYALVAQRLEQ       mu Bcl2L12

186  LVQEQLKSPPSPELQGPPSTEKEATLRRLVATLEEEAEVINQKLASDPAL     hu Bcl2L12
101  LVQEQLKSPDSSEEQGPPTEKEALLRRLVATLEEEAEVINQKLASDPAL      mu Bcl2L12

236  RSKLVRLSSDSFARLVELFCSRD----DSSRPSRACGPPPPSPEPLAR       hu Bcl2L12
151  HRKLARLSAGSFARLVELFSSRESSSSPNCSSSPLCGPPPPSPDPLAR       mu Bcl2L12

279  LALAMELSRRVAGLGGTLAGLSVEHVHSFTPMQA-CQWEGFLAVSPVDL      hu Bcl2L12
201  LALAMELSRRVAGLGGPLANLSVEHVHSFLPWVQA-GGWAGILASSPVDL     mu Bcl2L12

329  NLPLD                                                   hu
251  NLPLD                                                   mu
```

BCL2L12 POLYPEPTIDE ACTIVATORS AND INHIBITORS

RELATED APPLICATIONS

This application is a continuation-in-part application of and claims priority to International Patent Application Serial No. PCT/US2004/012591, filed Apr. 23, 2004, which claims priority to U.S. Provisional Patent Application No. 60/465,573, filed Apr. 25, 2003.

BACKGROUND

1. Technical Field

The invention relates to methods and materials involved in identifying Bcl2L12 polypeptide activators and inhibitors. The invention also relates to methods and materials involved in treating cancer.

2. Background Information

Many signaling pathways are involved in cancer initiation, progression, maintenance, and regression. Likewise, signaling pathways are involved in preventing or reducing cancer initiation, progression, and maintenance. In fact, organisms have developed apoptosis and survival signaling pathways to control the fate of cells. Several such pathways have been extensively studied. For example, extensive studies of the apoptosis and survival signaling in neurons and neuroblastoma revealed that survival/cell death regulators such as Bax, Apaf-1, caspase 3, caspase 9, PI3K, Akt, Bcl-2, and Bcl-xL play fundamental roles in neuronal cell death (for review, see, Yuan and Yankner, *Nature*, 407:802-809 (2000)).

Malignant gliomas represent the most common and most lethal form of brain tumors. The common gliomas involve the cerebral hemispheres of adults and carry a poor prognosis due to their propensity to infiltrate early and diffusely throughout the brain. These diffuse neoplasms are classified histologically as astrocytomas, oligodendrogliomas, or tumors with morphological features of both lineages. The more common astrocytic tumors are subsequently graded as pilocytic astrocytoma, grade I; astrocytoma, grade II; anaplastic astrocytoma, grade III; and glioblastoma multiforme (GBM), grade IV. Grade I tumors are biologically benign and can be surgically cured if deemed resectable at the time of diagnosis. Grade II tumors are well-differentiated malignancies with a long clinical course yet poor surgical outcome due to their diffuse nature and propensity to progress into grade III/IV lesions. The grade III anaplastic astrocytomas are highly aggressive, poorly differentiated, and intensely mitotic lesions that lead to death within a few years. Grade IV GBM tumors possess all of the Grade III histological features and are characterized further by microvascular proliferation and/or necrosis, extreme resistance to extant therapeutic modalities, and neurologically destructive death within 9-12 months.

GBMs can present with one of two distinct clinical histories. GBMs presenting in patients without evidence of prior low-grade disease are considered "primary" or "de novo" GBM. The primary GBMs typically arise in older patients. In contrast, "secondary" GBM usually arise in younger patients who initially present with a low-grade astrocytoma that eventually transforms into a grade IV GBM lesion within 5-10 years of the initial diagnosis, regardless of prior therapy. Indeed, a hallmark feature of the malignant gliomas is their lethal end-point.

On the molecular level, significant effort has been directed towards cataloging the genetic changes present in low- and high-grade gliomas, resulting in the identification of several signature mutations that mark their genesis and malignant evolution. The low-grade gliomas typically harbor PDGF pathway activation as well as p53 loss-of-function mutations; while high-grade disease often exhibits activation/overexpression of EGFR as well as loss of INK4a/ARF and PTEN tumor suppressor gene function. Equally apparent from molecular analysis of the high-grade disease is the fact that many GBMs do not harbor these signature lesions, implying that many other genetic mutations driving glioma progression remain to be identified. In fact, high-grade gliomas typically exhibit a high number of chromosomal structural aberrations that presumably result from compromised genome stability mechanisms. For example, spectral karyotype analyses of GBM samples reveal the presence of many recurrent complex non-reciprocal translocations (NRTs). NRTs are typically the end-product of a repaired double-stranded DNA break (DSB) that can serve as a nidus for amplification or deletion at the breakage site.

Previous cytogenetic and chromosomal comparative genomic hybridization (CGH) studies have uncovered a number of recurrent regional gains and losses in malignant gliomas that appear to convey important clinical information (Mohapatra et al., *Genes Chromosomes Cancer*, 3:195-206 (1998)). For example, gains of 12q and 19 were found to be more frequent in tumors that were slower to recur, whereas losses of 6q and 13 and gains of 20 were found to be more frequent in tumors that recurred more quickly (Weber et al., *Oncogene*, 13:983-994 (1996)). In addition, the frequency of 7q and 19 gains differs between relatively radiation-sensitive and radiation-resistant GBMs (Huhn et al., *Clin. Cancer Res.*, 5:1435-43 (1999)).

SUMMARY

The invention involves methods and materials related to Bcl2L12 polypeptides and the biological activities of Bcl2L12 polypeptides. For example, the invention provides methods and materials related to identifying activators and inhibitors of Bcl2L12 polypeptide activities such as the ability to block apoptosis and promote cell growth and transformation. Identifying activators and inhibitors of Bcl2L12 polypeptide activities can lead to the development of drugs capable of promoting, for example, apoptosis in tumor cells.

The invention also involves methods and materials related to treating mammals (e.g., humans) having cancer cells that express a Bcl2L12 polypeptide. For example, the invention provides methods and materials related to treating mammals having a glioma by administering a compound that reduces a Bcl2L12 polypeptide activity such as the ability to block apoptosis and promote cell growth and transformation. Such compounds can reduce a Bcl2L12 polypeptide activity by reducing the expression of Bcl2L12 mRNA or Bcl2L12 polypeptides or by binding to a Bcl2L12 polypeptide and inhibiting a function of a Bcl2L12 polypeptide.

In general, one aspect of the invention features a method for identifying a compound that reduces Bcl2L12 polypeptide-induced inhibition of caspase polypeptide (e.g., a caspase-3, caspase-7, or caspase-9 polypeptide) activation. The method includes (a) contacting a sample with a test compound, wherein the sample contains a caspase polypeptide (e.g., a caspase-3, caspase-7, or caspase-9 polypeptide) and a Bcl2L12 polypeptide, and (b) determininig whether or not the presence of the test compound increases caspase polypeptide (e.g., a caspase-3, caspase-7, or caspase-9 polypeptide) activation in the sample to a level greater than the level of caspase polypeptide (e.g., a caspase-3, caspase-7, or caspase-9 polypeptide) activation in a control sample lacking the test compound, wherein an increase in caspase polypeptide (e.g., a caspase-3, caspase-7, or caspase-9 polypeptide) activation in the sample indicates that the test compound is the compound. The sample can contain cells or a lysate of the cells. The cells can be glioma cells, astrocytes, or melanocytes. The cells can be U87MG cells. The cells can contain an isolated nucleic acid containing a nucleic acid sequence encoding the Bcl2L12 polypeptide. The isolated nucleic acid can contain an constitutive promoter sequence operably linked to the nucleic acid sequence encoding the Bcl2L12 polypeptide. The isolated nucleic acid can contain an inducible promoter sequence operably linked to the nucleic acid sequence encoding the Bcl2L12 polypeptide. The cells can contain an isolated nucleic acid containing a nucleic acid sequence encoding the caspase polypeptide (e.g., a caspase-3, caspase-7, or caspase-9 polypeptide). The isolated nucleic acid can contain a constitutive promoter sequence operably linked to the nucleic acid sequence encoding the caspase polypeptide (e.g., a caspase-3, caspase-7, or caspase-9 polypeptide). The isolated nucleic acid can contain an inducible promoter sequence operably linked to the nucleic acid sequence encoding the caspase polypeptide (e.g., a caspase-3, caspase-7, or caspase-9 polypeptide). The sample can contain an Apaf-1 polypeptide. The sample can contain a cytochrome c polypeptide. The sample can contain dATP. The Bcl2L12 polypeptide can be a human Bcl2L12 polypeptide. The Bcl2L12 polypeptide can be a mouse Bcl2L12 polypeptide. The Bcl2L12 polypeptide can lack a BH2 domain sequence. The Bcl2L12 polypeptide can contain the sequence set forth in SEQ ID NO:1 or 2, or amino acid sequence 1 to 310, 1 to 267, or 1 to 167 of the sequence set forth in SEQ ID NO:1. The sample can contain a polypeptide substrate for the caspase polypeptide (e.g., a caspase-3, caspase-7, or caspase-9 polypeptide). The polypeptide substrate can contain a DEVD (SEQ ID NO:27) or LEHD (SEQ ID NO:28) amino acid sequence. The polypeptide substrate can be fluorogenic or colorogenic. The polypeptide substrate can contain aminomethylcoumarin or can contain rhodamine. The polypeptide substrate can contain LEHD-aminomethyl-coumarin. The step (b) can include determining whether or not the presence of the test compound increases the level of fluorescence in the sample to a level greater than the level of fluorescence in the control sample lacking the test compound, wherein an increase in the level of fluorescence in the sample indicates that the test compound is the compound. The step (b) can include determining whether or not the presence of the test compound increases the level of a caspase-7 p20 polypeptide or a caspase-9 p35 polypeptide in the sample to a level greater than the level of a caspase-7 p20 polypeptide or a caspase-9 p35 polypeptide in the control sample lacking the test compound, wherein an increase in the level of a caspase-7 p20 polypeptide or a caspase-9 p35 polypeptide in the sample indicates that the test compound is the compound. The step (b) can include determining whether or not the presence of the test compound increases the level of a caspase-7 p10 polypeptide or a caspase-9 p37 polypeptide in the sample to a level greater than the level of a caspase-7 p10 polypeptide or a caspase-9 p37 polypeptide in the control sample lacking the test compound, wherein an increase in the level of a caspase-7 p10 polypeptide or a caspase-9 p37 polypeptide in the sample indicates that the test compound is the compound.

In another aspect, the invention features a method for identifying a compound that reduces binding of a Bcl2L12 polypeptide to an Apaf-1 polypeptide. The method includes (a) contacting a sample with a test compound, wherein the sample contains the Bcl2L12 polypeptide and the Apaf-1 polypeptide, and (b) determining whether or not the presence of the test compound reduces binding of the Bcl2L12 polypeptide to the Apaf-1 polypeptide in the sample to a level less than the level of binding of the Bcl2L12 polypeptide to the Apaf-1 polypeptide in a control sample lacking the test compound, wherein a decrease in binding of the Bcl2L12 polypeptide to the Apaf-1 polypeptide in the sample indicates that the test compound is the compound. The sample can contain cells or a lysate from the cells. The cells can be glioma cells, astrocytes, or melanocytes. The cells can be U87MG cells. The cells can contain an isolated nucleic acid containing a nucleic acid sequence encoding the Bcl2L12 polypeptide. The isolated nucleic acid can contain a constitutive promoter sequence operably linked to the nucleic acid sequence encoding the Bcl2L12 polypeptide. The isolated nucleic acid can contain an inducible promoter sequence operably linked to the nucleic acid sequence encoding the Bcl2L12 polypeptide. The cells can contain an isolated nucleic acid containing a nucleic acid sequence encoding the Apaf-1 polypeptide. The isolated nucleic acid can contain a constitutive promoter sequence operably linked to the nucleic acid sequence encoding the caspase-9 polypeptide. The isolated nucleic acid can contain an inducible promoter sequence operably linked to the nucleic acid sequence encoding the caspase-9 polypeptide. The sample can contain a caspase-9 polypeptide, a cytochrome c polypeptide, or dATP. The Bcl2L12 polypeptide can be a human or mouse Bcl2L12 polypeptide. The Bcl2L12 polypeptide can lack a BH2 domain sequence. The Bcl2L12 polypeptide can contain the sequence set forth in SEQ ID NO:1 or 2, or amino acid sequence 1 to 310, 1 to 267, or 1 to 167 of the sequence set forth in SEQ ID NO:1. The step (b) can include determining whether or not the presence of the test compound reduces the level of detectable Bcl2L12 polypeptide-Apaf-1 polypeptide complexes in the sample to a level less than the level of detectable Bcl2L12 polypeptide-Apaf-1 polypeptide complexes in the control sample lacking the test compound, wherein a reduction in the level of detectable Bcl2L12 polypeptide-Apaf-1 polypeptide complexes in the sample indicates that the test compound is the compound.

In another aspect, the invention features a method for identifying a compound that inhibits the anti-apoptosis activity of a Bcl2L12 polypeptide. The method includes (a) exposing cells to an apoptotic stimulus in the presence of a test compound, wherein the cells contain the Bcl2L12 polypeptide, and (b) determining whether or not the presence of the test compound increases apoptosis of the cells to a level greater than the level of apoptosis in control cells exposed to the apoptotic stimulus in the absence of the test compound, wherein an increase in apoptosis of the cells indicates that the test compound is the compound. The cells can be glioma cells, astrocytes, or melanocytes. The cells can be U87MG cells. The step (b) can include measuring caspase-3 or caspase-9 activity with a fluorogenic or colorogenic assay. The cells can contain an isolated nucleic acid containing a nucleic acid sequence encoding the Bcl2L12 polypeptide. The isolated nucleic acid can contain a constitutive promoter sequence operably linked to the nucleic acid sequence encoding the Bcl2L12 polypeptide. The isolated nucleic acid can contain an inducible promoter sequence operably linked to the nucleic acid sequence encoding the Bcl2L12 polypeptide. The cells can contain an isolated nucleic acid containing a nucleic acid sequence encoding a caspase-9 polypeptide. The isolated nucleic acid can contain a constitutive promoter sequence operably linked to the nucleic acid sequence encoding the caspase-9 polypeptide. The isolated nucleic acid can contain an inducible promoter sequence operably linked to the nucleic acid sequence encoding the caspase-9 polypeptide. The Bcl2L12 polypeptide can be a human or mouse Bcl2L12 polypeptide. The Bcl2L12 polypeptide can lack a BH2 domain sequence. The Bcl2L12 polypeptide can contain the sequence set forth in SEQ ID NO:1 or 2, or amino acid sequence 1 to 310, 1 to 267, or 1 to 167 of the sequence set forth in SEQ ID NO:1. The apoptotic stimulus can include radiation. The apoptotic stimulus can be staurosporine. The step (b) can include measuring apoptosis with an annexin polypeptide binding assay. The step (b) can include measuring apoptosis with a DNA fragmentation assay.

In another aspect, the invention features a method for identifying a compound that inhibits the pro-necrosis activity of a Bcl2L12 polypeptide. The method includes (a) exposing cells to an apoptotic stimulus in the presence of a test compound, wherein the cells contain the Bcl2L12 polypeptide, and (b) determining whether or not the presence of the test compound reduces necrosis of the cells to a level greater than the level of necrosis in control cells exposed to the apoptotic stimulus in the absence of the test compound, wherein a reduction in necrosis of the cells indicates that the test compound is the compound. The cells can be glioma cells, astrocytes, or melanocytes. The cells can be U87MG cells. The cells can contain an isolated nucleic acid containing a nucleic acid sequence encoding the Bcl2L12 polypeptide. The isolated nucleic acid can contain a constitutive promoter sequence operably linked to the nucleic acid sequence encoding the Bcl2L12 polypeptide. The isolated nucleic acid can contain an inducible promoter sequence operably linked to the nucleic acid sequence encoding the Bcl2L12 polypeptide. The Bcl2L12 polypeptide can be a human or mouse Bcl2L12 polypeptide. The Bcl2L12 polypeptide can lack a BH2 domain sequence. The Bcl2L12 polypeptide can contain the sequence set forth in SEQ ID NO:1 or 2, or amino acid sequence 1 to 310, 1 to 267, or 1 to 167 of the sequence set forth in SEQ ID NO:1. The apoptotic stimulus can include radiation. The apoptotic stimulus can be staurosporine. The step (b) can include determining the level of necrosis of the cells contains measuring nuclear swelling of the cells, measuring plasma membrane integrity of the cells, or measuring mitochondrial membrane potentials of the cells.

Another aspect of the invention features a method for identifying a compound that inhibits Bcl2L12 polypeptide-induced phosphorylation of a MAP kinase polypeptide. The method includes (a) contacting a sample with a test compound, wherein the sample contains a Bcl2L12 polypeptide and the MAP kinase polypeptide, and (b) determining whether or not the presence of the test compound reduces phosphorylation of the MAP kinase polypeptide in the sample to a level less than the level of phosphorylation of the MAP kinase polypeptide in a control sample lacking the test compound, wherein an increase in phosphorylation of the MAP kinase polypeptide in the sample indicates that the test compound is the compound. The sample can contain cells or a lysate from the cells. The cells can be glioma cells, astrocytes, or melanocytes. The cells can contain an isolated nucleic acid containing a nucleic acid sequence encoding the Bcl2L12 polypeptide. The isolated nucleic acid can contain a constitutive promoter sequence operably linked to the nucleic acid sequence encoding the Bcl2L12 polypeptide. The isolated nucleic acid can contain an inducible promoter sequence operably linked to the nucleic acid sequence encoding the Bcl2L12 polypeptide. The cells can contain an isolated nucleic acid containing a nucleic acid sequence encoding the MAP kinase polypeptide. The isolated nucleic acid can contain a constitutive promoter sequence operably linked to the nucleic acid sequence encoding the MAP kinase polypeptide. The isolated nucleic acid can contain an inducible promoter sequence operably linked to the nucleic acid sequence encoding the MAP kinase polypeptide. The Bcl2L12 polypeptide can be a human or mouse Bcl2L12 polypeptide. The Bcl2L12 polypeptide can lack a BH2 domain sequence. The Bcl2L12 polypeptide can contain the sequence set forth in SEQ ID NO:1 or 2, or amino acid sequence 1 to 310, 1 to 267, or 1 to 167 of the sequence set forth in SEQ ID NO:1. The MAP kinase polypeptide can be an ERK1 polypeptide. The MAP kinase polypeptide can be an ERK2 polypeptide. The step (b) can include determining the level of phosphorylation with an anti-phosphorylated tyrosine antibody.

Another aspect of the invention features a method for identifying a compound that inhibits cell proliferation. The method includes (a) contacting cells with a test compound, wherein the cells contain an isolated nucleic acid containing a nucleic acid sequence encoding a Bcl2L12 polypeptide, and wherein the cells express the Bcl2L12 polypeptide, and (b) determining whether or not the presence of the test compound reduces proliferation of the cells to a level greater than the level of proliferation in control cells not contacted with the test compound, wherein a reduction in proliferation of the cells indicates that the test compound is the compound. The cells can be astrocytes. The cells can be Ink4a/Arf-/-astrocytes. The nucleic acid construct can contain a constitutive promoter sequence operably linked to the nucleic acid sequence encoding the Bcl2L12 polypeptide. The nucleic acid construct can contain an inducible promoter sequence operably linked to the nucleic acid sequence encoding the Bcl2L12 polypeptide. The Bcl2L12 polypeptide can be a human or mouse Bcl2L12 polypeptide. The Bcl2L12 polypeptide can lack a BH2 domain sequence. The Bcl2L12 polypeptide can contain the sequence set forth in SEQ ID NO:1 or 2, or amino acid sequence 1 to 310, 1 to 267, or 1 to 167 of the sequence set forth in SEQ ID NO:1.

Another aspect of the invention features a method for identifying a compound that reduces binding of a Bcl2L12 polypeptide to a p53 polypeptide. The method includes (a) contacting a sample with a test compound, wherein the sample contains the Bcl2L12 polypeptide and the p53 polypeptide, and (b) determining whether or not the presence of the test compound reduces binding of the Bcl2L12 polypeptide to the p53 polypeptide in the sample to a level less than the level of binding of the Bcl2L12 polypeptide to the p53 polypeptide in a control sample lacking the test compound, wherein a decrease in binding of the Bcl2L12 polypeptide to the p53 polypeptide in the sample indicates that the test compound is the compound. The sample can contain cells or a lysate of the cells. The cells can be glioma cells, astrocytes, or melanocytes. The cells can contain an isolated nucleic acid containing a nucleic acid sequence encoding the Bcl2L12 polypeptide. The isolated nucleic acid can contain a constitutive promoter sequence operably linked to the nucleic acid sequence encoding the Bcl2L12 polypeptide. The isolated nucleic acid can contain an inducible promoter sequence operably linked to the nucleic acid sequence encoding the Bcl2L12 polypeptide. The cells can contain an isolated nucleic acid containing a nucleic acid sequence encoding the p53 polypeptide. The isolated nucleic acid can contain a constitutive promoter sequence operably linked to the nucleic acid sequence encoding the p53 polypeptide. The isolated nucleic acid can contain an inducible promoter sequence operably linked to the nucleic acid sequence encoding the p53 polypeptide. The cells can contain an isolated nucleic acid containing a nucleic acid sequence encoding a detectable marker polypeptide. The detectable marker polypeptide can be a luciferase polypeptide. The isolated nucleic acid can contain a promoter sequence recognized by a p53 polypeptide operably linked to the nucleic acid sequence encoding the detectable marker polypeptide. The step (b) can include determining whether or not the presence of the test compound increases the level of the detectable marker polypeptide in the sample to a level greater than the level of detectable marker polypeptide in the control sample lacking the test compound, wherein an increase in the level of detectable marker polypeptide in the sample indicates that the test compound is the compound. The promoter sequence recognized by a p53 polypeptide can contain a sequence from the Bax promoter region. The Bcl2L12 polypeptide can be a human or mouse Bcl2L12 polypeptide. The Bcl2L12 polypeptide can lack a BH2 domain sequence. The Bcl2L12 polypeptide can contain the sequence set forth in SEQ ID NO:1 or 2, or amino acid sequence 1 to 310, 1 to 267, or 1 to 167 of the sequence set forth in SEQ ID NO:1. The step (b) can include determining whether or not the presence of the test compound reduces the level of detectable Bcl2L12 polypeptide-p53 polypeptide complexes in the sample to a level less than the level of detectable Bcl2L12 polypeptide-p53 polypeptide complexes in the control sample lacking the test compound, wherein a reduction in the level of detectable Bcl2L12 polypeptide-p53 polypeptide complexes in the sample indicates that the test compound is the compound.

Another aspect of the invention features a method for reducing Bcl2L12 polypeptide activity in a cell. The method includes administering an isolated nucleic acid to the cell, wherein the isolated nucleic acid contains a sequence that promotes RNA interference against expression of a Bcl2L12 polypeptide in the cell. The sequence can contain between about 19 and 29 nucleotides present in a nucleic acid sequence encoding the Bcl2L12 polypeptide.

Another aspect of the invention features a cell lysate from a cell, wherein the cell lysate contains a Bcl2L12 polypeptide, and wherein the cell is an Ink4a/Arf deficient astrocyte containing an isolated nucleic acid encoding the Bcl2L12 polypeptide.

In another aspect, the invention features a method for treating a mammal having cancer cells, wherein the cancer cells contain a Bcl2L12 polypeptide. The method includes administering a compound to the mammal under conditions wherein the number of the cancer cells in the mammal is reduced, wherein the compound is capable of reducing the level of Bcl2L12 polypeptide activity in the cancer cells. The mammal can be a human. The cancer cells can be glioma cells, bone cancer cells, cervical cancer cells, colon cancer cells, gastrointestinal cancer cells, ovarian cancer cells, pancreatic cancer cells, stomach cancer cells, or testicular cancer cells. The genome of each of the cancer cells can contain three or more nucleic acid sequences that encode the Bcl2L12 polypeptide. The compound can be nucleic acid. The nucleic acid can contain a sequence encoding the Bcl2L12 polypeptide. The nucleic acid can induce RNA interference against expression of the Bcl2L12 polypeptide. The cancer cells in the mammal can form a tumor, and the mass of the tumor can be reduced by at least 10 percent. The cancer cells in the mammal can form a tumor, and the mass of the tumor can be reduced by at least 20 percent. The cancer cells in the mammal can form a tumor, and the mass of the tumor can be reduced by at least 30 percent.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 3 is a sequence alignment of human and mouse Bcl2L12 amino acid sequences. The depicted human amino acid sequence is SEQ ID NO:1, while the depicted mouse amino acid sequence is SEQ ID NO:2.

Apaf-1 is a cytosolic marker. Cytochrome P450 reductase is an endoplasmatic reticulum (ER) marker. EGFR is an ER and plasma membrane marker. Histon H4 is a nuclear marker.

Figure 7:
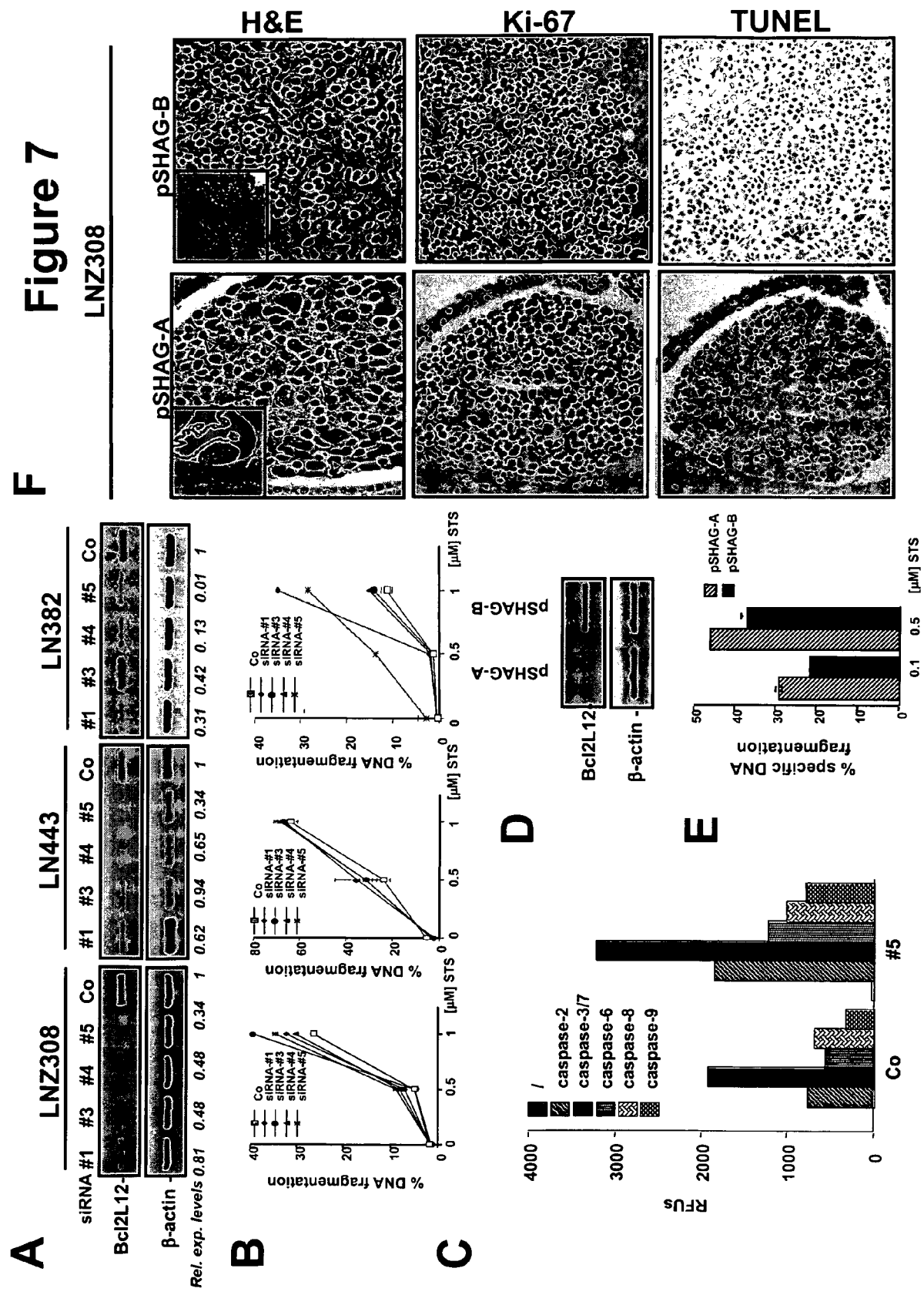

FIG. 7A contains photographs of the expression levels of Bcl2L12 and β-actin mRNA in LNZ308, LN443, and LN382 cells transfected with the indicated siRNA molecules. The relative expression levels of Bcl2L12 is provided under each treatment. FIG. 7B is three line graphs plotting the percent DNA fragmentation observed in LNZ308, LN443, and LN382 cells transfected with the indicated siRNA molecules and treated with either 0, 0.5, or 1 μM STS. FIG. 7C is a bar graph plotting the activity for the indicated caspases in RFUs for LNZ308 cells transfected with control (Co) or siRNA oligonucleotide #5. The cells also were treated with STS for 24 hours. FIG. 7D is a photograph of Bcl2L12 and β-actin mRNA levels exhibited in LNZ308 cells transfected with pSHAG-A or pSHAG-B. FIG. 7E is a bar graph plotting the percent of specific DNA fragmentation for LNZ308 cells transfected with pSHAG-A or PSHAG-B and treated with either 0.1 or 0.5 μM STS. The percent of specific DNA fragmentation is determined by subtracting the percent of DNA fragmentation observed in untreated cells. FIG. 7F contains photographs of tumors obtained from SCID mice given LNZ308 cells transfected with either pSHAG-A or pSHAG-B. The cells in the top panels were stained with an H&E stain. The cells in the middle panels were stained for a proliferation marker, Ki-67. The cells in the bottom panels were analyzed using a terminal deoxynucleotidyl transferase-mediated dUTP nick-end labeling (TUNEL) method.

FIG. 8A contains photographs of Western blot analyses of procaspase-9, -7, and -3 expression in INK4a/Arf deficient astrocytes transduced with Bcl2L12-V5 or pBabe vector and treated with STS (1 μM) for the indicated periods of time. FIG. 8B contains photographs of Western blot analyses of caspase-9, -7, and -3 expression in INK4a/Arf deficient astrocytes transduced with pBabe vector or a vector expressing Bcl2L12-V5 or EGFR* polypeptides and treated with STS (1 μM) for the indicated periods of time. The migration positions of the individual procaspases and active species are indicated. FIG. 8C contains photographs of Western blot analyses of caspase-9, -7, and -3 polypeptide expression in U87MG cells that stably expressed control shRNA or a Bcl2L12-targeting shRNA (shL12-1), and that were treated with STS (1 μM) for the indicated periods of time. The migration positions of the active enzymes are indicated. FIG. 8D is a graph plotting DEVDase activity in INK4a/Arf deficient astrocytes that ectopically expressed Bcl2L12-V5 polypeptides or contained pBabe, and that were treated with STS (1 μM) for the indicated periods of time (*p=0.038). FIG. 8E contains autoradiographs of gels monitoring processing of in vitro translated caspase-7 in lysates from astrocytes that were transduced with pBabe vector or a vector expressing Bcl2L12-V5 polypeptides and activated with dATP (1 mM) and cytochrome c (5 μM). The migration positions of the proenzyme and the cleavage products are indicated. FIG. 8F is a graph plotting DEVDase activity in lysates from astrocytes that were transduced with pBabe vector or a vector expressing Bcl2L12-V5 polypeptides and activated with dATP (1 mM) and cytochrome c (5 μM) for the indicated periods of time (*p=0.08).

Figure 9:
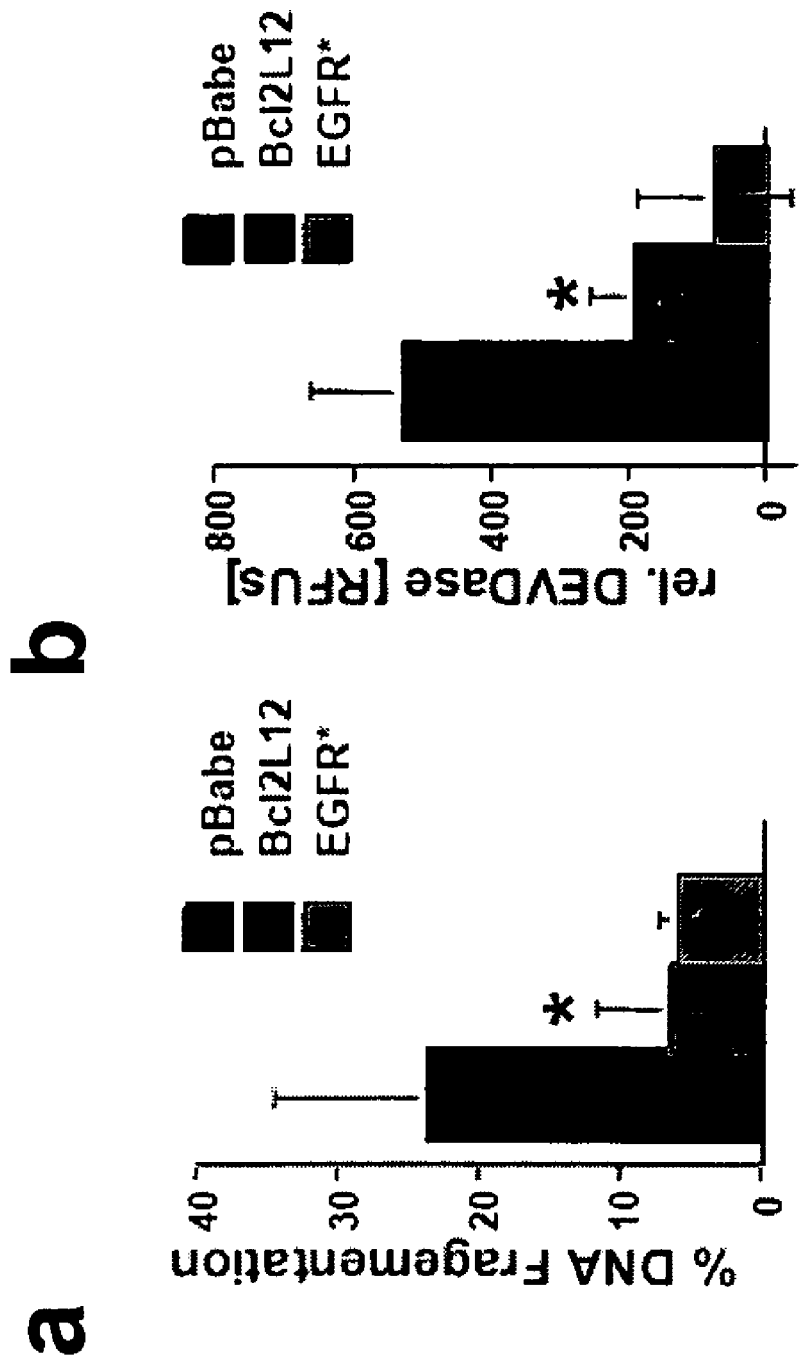

FIG. 9A is a graph plotting the percent DNA fragmentation in INK4a/Arf deficient astrocytes that were transduced with pBabe vector or a vector expressing Bcl2L12-V5 or EGFR* polypeptides and stimulated with 1 μM STS. FIG. 9B is a graph plotting DEVDase activity in INK4a/Arf deficient astrocytes that were transduced with pBabe or a vector expressing Bcl2L12-V5 or EGFR* polypeptides and stimulated with 1 μM STS.

Figure 10:
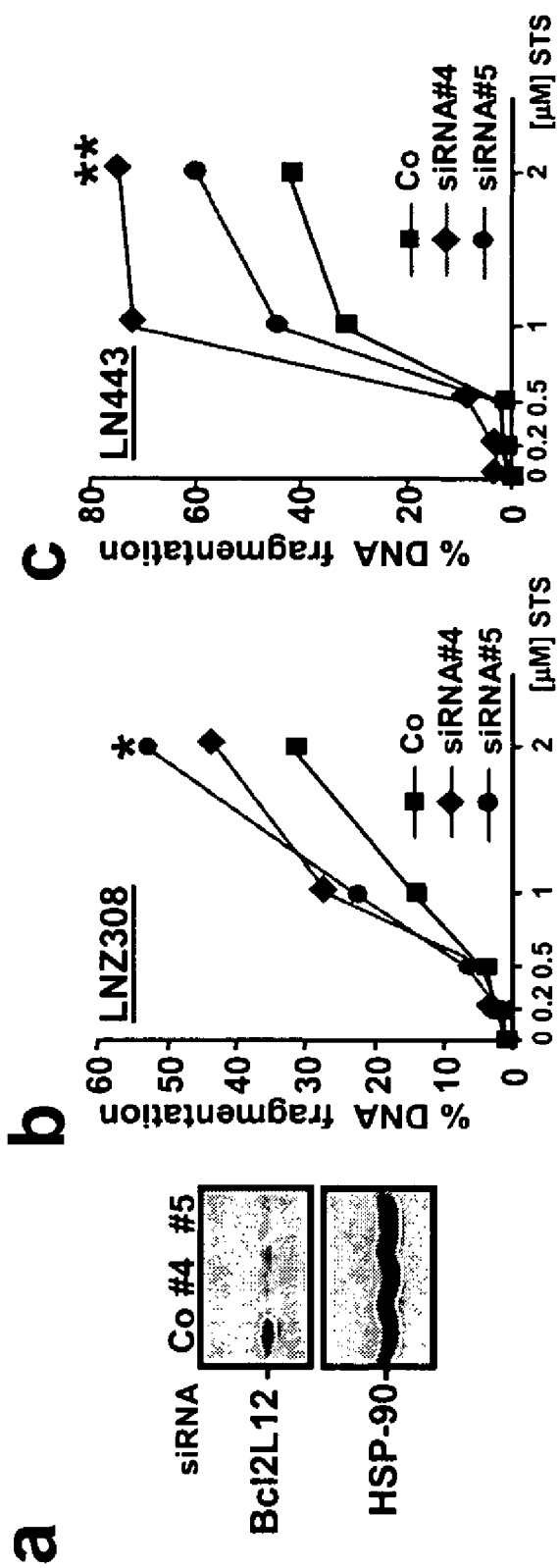

FIG. 10A is a photograph of a Western blot analysis of Bcl2L12 polypeptide expression in lysates from U87MG cells transfected with control siRNA or Bcl2L12-targeting siRNA#4 or #5. FIG. 10B is a graph plotting the percent DNA fragmentation in LNX308 cells transfected with control siRNA or Bcl2L12-targeting siRNA#4 or #5 and treated with the indicated amounts of STS. FIG. 10C is a graph plotting the percent DNA fragmentation in LN443 cells transfected with control siRNA or Bcl2L12-targeting siRNA#4 or #5 and treated with the indicated amounts of STS.

Figure 11:
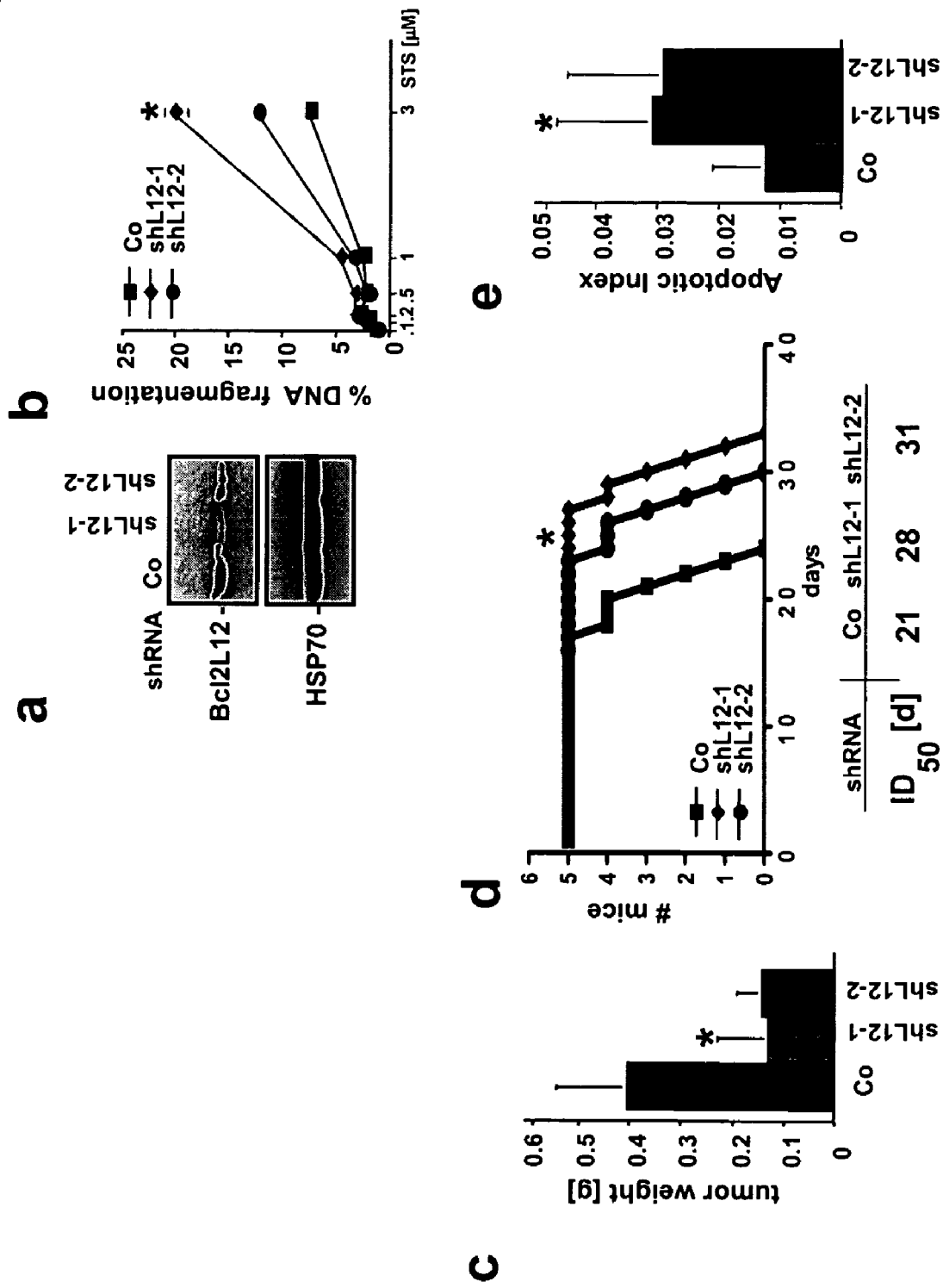

FIG. 11A is a photograph of a Western blot analysis of Bcl2L12 expression in lysates from U87MG cells stably expressing Bcl2L12-targeting shRNA (shL12-1 or shL12-2) or control shRNA. Migration positions of Bcl2L12 polypeptides and the loading control HSP70 are indicated. FIG. 11B is a graph plotting the percent DNA fragmentation in U87MG cells transduced with control shRNA or Bcl2L12-targeting shRNA (shL12-1 or shL12-2) and treated with the indicated amounts of STS. FIG. 11C is a graph plotting the average tumor weight in SCID mice injected with U87MG cells expressing control shRNA, shL12-1, or shL12-2. FIG. 11D is a graph plotting survival curves for SCID mice injected with U87MG cells expressing control shRNA, shL12-1, or shL12-2. FIG. 11E is a graph plotting the apoptotic index in cells expressing control shRNA, shL12-1, or shL12-2.

Figure 12:
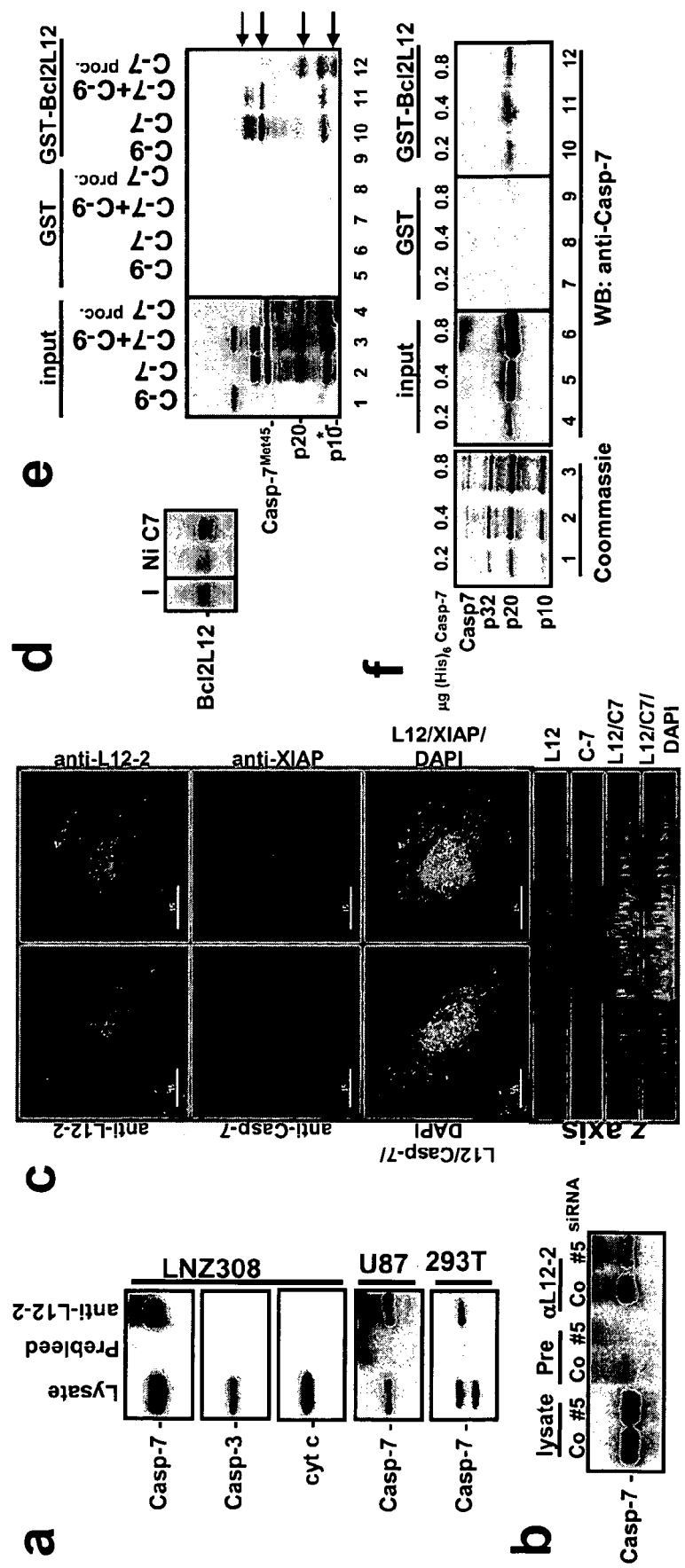

FIG. 12A is a photograph of a Western blot of anti-L12-2 immunoprecipitates from lysates of LNZ308, U87MG, and 293T cells analyzed for procaspase-7 and -3 and cytochrome c. The migration positions of the individual polypeptides are indicated. 1/40 of the lysate used for the immunoprecipitation was loaded to quantify the amount of co-immunoprecipitated caspase-7. FIG. 12B is a photograph of a Western blot of anti-L12-2 immunoprecipitates from control- and siRNA#5-treated U87MG cells analyzed for caspase-7. The migration position of the proenzyme is indicated. 1/40 of the lysate used for the immunoprecipitation was loaded to quantify the amount of co-immunoprecipitated caspase-7. FIG. 12C contains photomicrographs of LNZ308 cells subjected to deconvolution microscopy using the anti-L12-2 antiserum (upper row), a monoclonal anti-caspase-7 antibody (left panel, center row), and a monoclonal anti-XIAP antibody (right panel, center row). Green (of top row shown in grayscale) and red (of center row shown in grayscale)images were overlayed with DAPI staining (Merge/DAPI, right column). Deconvolved images for the Bcl2L12/caspase-7 staining were rotated by 90 degrees along the x-axis to analyze Bcl2L12 polypeptide and caspase-7 polypeptide distribution along the z-axis (lower panel). Bar, 15 μm. FIG. 12D contains autoradiographs of gels analyzing precipitates formed by incubating in vitro translated Bcl2L12-V5 polypeptides with $(His)_6$-caspase-7 polypeptides (C7) or Ni-NTA beads (Ni). The migration position of V5-tagged Bcl2L12 polypeptides is indicated. Input (I) represents 1/10 of the total in vitro translated product used in the precipitation experiment. FIG. 12E contains autoradiographs of gels analyzing precipitates formed by incubating in vitro-translated caspase-9 polypeptides (C-9), caspase-7 polypeptides (C-7), a mixture of caspase-9 and caspase-7 polypeptides (C-9+C-7), and processed caspase-7 polypeptides (C-7 proc.) with GST or GST-Bcl2L12 polypeptides coupled to GSH beads. The migration position of a caspase-7 species truncated due to an in-frame secondary start-site (Casp-7Met45) is indicated along with the migration positions of the active caspase-7 subunits, p20 and p10. The input was 1/10 of the in vitro translated products used in the pull down experiments. FIG. 12F contains photographs demonstrating that Bcl2L12 and caspase-7 polypeptides interact directly. GST or GST-Bcl2L12 coupled to GSH beads were incubated with increasing amounts of soluble recombinant (His)6-tagged caspase-7 polypeptides, subjected to SDS-PAGE followed by coommassie staining or by western blot analysis using an anti-caspase-7 antibody. Due to immediate autoproteolysis of procaspase-7 upon polypeptide induction in bacteria, the proenzyme was nearly completely converted into the cleavage intermediate p32 and the active subunits p20 and p10 (lanes 1-3). The migration positions of procasaspe-7 (Casp-7), the cleavage intermediate p32, and the active subunits p20 and p10 are indicated.

Figure 13:
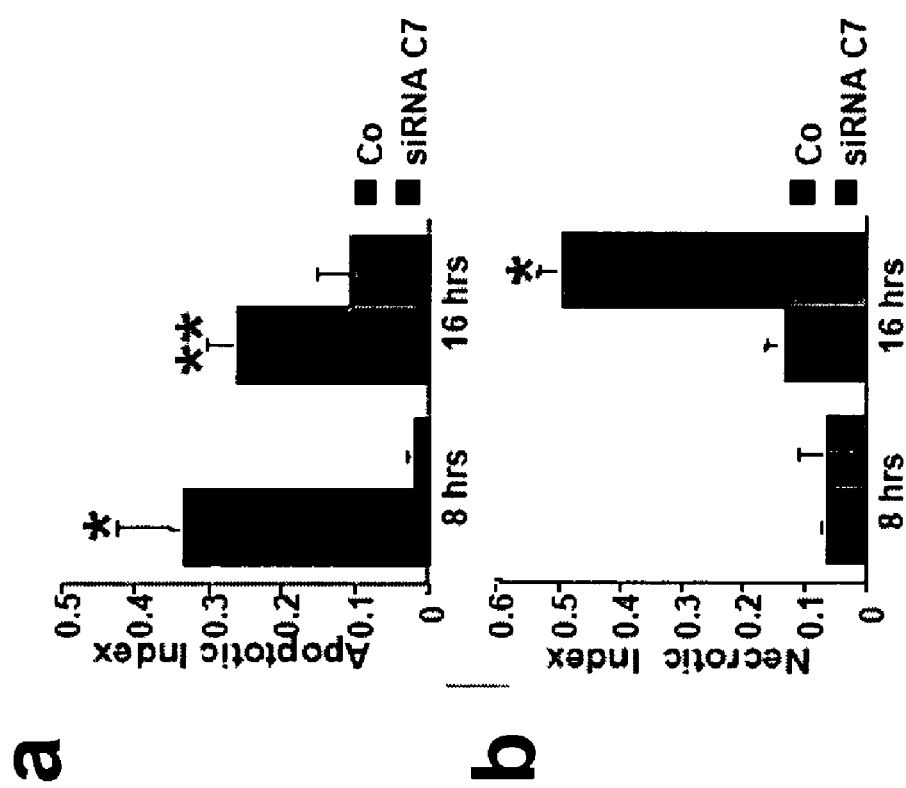

FIGS. 13A and B are bar graphs plotting results demonstrating that knockdown of caspase-7 results in a decreased apoptotic (c, *p=0.03; p=0.07) and increased necrotio index (d, *p=0.012). ~50 cells were counted per grid (total 3 grids) to assess the fraction of apoptotic (cells with chromatin condensation) and necrotic cells (cells with desintegrated plasma membrane).

DETAILED DESCRIPTION

The invention provides methods and materials related to Bcl2L12 polypeptides and the biological activities of Bcl2L12 polypeptides. For example, the invention provides methods and materials related to identifying activators and inhibitors of Bcl2L12 polypeptide activities. Bcl2L12 polypeptide activities include, without limitation, the ability to inhibit caspase activation (e.g., caspase-9 activation), block apoptosis, bind Apaf-1 polypeptides, promote necrosis, contribute to phosphorylation of MAP kinases (e.g., Erk1 and Enk2 polypeptides), promote cell growth, promote cell transformnation, bind p53 polypeptides, and inhibit p53 polypeptide driven transcription.

The invention also provides methods and materials related to treating mammals (e.g., humans) having cancer cells that express a Bcl2L12 polypeptide. For example, the invention provides methods and materials related to treating mammals having a glioma by administering a compound that reduces a Bcl2L12 polypeptide activity such as the ability to block apoptosis and promote cell growth and transformation. Such compounds can reduce a Bcl2L12 polypeptide activity by reducing the expression of Bcl2L12 mRNA or Bcl2L12 polypeptides or by binding to a Bcl2L12 polypeptide and inhibiting a function of a Bcl2L12 polypeptide.

The invention provides methods for identifying compounds that reduce the ability of Bcl2L12 polypeptides to inhibit caspase activation (e.g., caspase-3 or caspase-9 activation). Such methods typically include contacting a sample with a test compound and determining whether or not the presence of the test compound increases caspase polypeptide activation. Any type of sample and test compound can be used. Typically, the sample contains a Bcl2L12 polypeptide and a caspase polypeptide. For example, the sample can be a cell lysate prepared from cells expressing both Bcl2L12 and caspase-9 polypeptides. In this case, the sample can be used to identify compounds capable of reducing the inhibition of caspase-9 activity by Bcl2L12 polypeptides.

Any method can be used to determine whether or not a test compound increases caspase polypeptide activation. As described herein, Bcl2L12 polypeptides can inhibit caspase activation. For example, cells expressing a Bcl2L12 polypeptide can exhibit less conversion of pro-caspase-9 into caspase-9 p35 and p37 polypeptides. In addition, Bcl2L12 polypeptides can inhibit the enzymatic activity of caspases as assessed using polypeptide substrates designed to contain one or more caspase recognition sequences. Thus, in one embodiment, standard molecular and biochemical techniques (e.g., SDS-PAGE, Western blots, immunostaining, ELISA, and immunoprecipitation) can be used to measure the level of pro-caspase-9 conversion into caspase-9 p35 and p37 polypeptides. For example, anti-caspase-9 antibodies can be used to detect the amount of caspase-9 p35 and p37 polypeptides present in a sample incubated with a test compound. In this case, an increase in the level of caspase-9 p35 and p37 polypeptides as compared to a control sample not treated with the test compound can indicate that the test compound is a compound that reduces the ability of Bcl2L12 polypeptides to inhibit caspase-9 activation.

In another embodiment, standard molecular and biochemical techniques can be used to measure the level of enzymatic activity exhibited by a caspase polypeptide. For example, a polypeptide substrate containing a cleavage recognition sequence for the particular caspase polypeptide activity to be measured can be added to the sample. For example, a polypeptide containing an LEHD (SEQ ID NO:28) amino acid sequence can be used to assess caspase-9 activity. The activity of any caspase polypeptide (e.g., caspase-1, caspase-2, caspase-3, caspase-4, caspase-5, caspase-6, caspase-7, caspase-8, and caspase-9) can be determined using polypeptides containing a cleavage recognition sequence for the particular caspase polypeptide activity to be assessed. Examples of recognition sequences that can be used to measure the activity of particular caspase polypeptides can be found elsewhere (Thornberry et al., *J. Biol. Chem.*, 272:17907-17911 (1997)).

Typically, the polypeptide substrate contains a label (e.g., fluorometric or colorometric label) that allows for the detection of resulting cleavage products. For example, Ac-LEHD-AFC or Ac-LEHD-AMC (obtained from Bachem AG) can be used to assess caspase-9 activity since cleavage of Ac-LEHD-AFC or Ac-LEHD-AMC can result in an increased signal detectable using a fluorometric or colorometric reader. In this case, an increase in the level of substrate cleavage in a sample containing a test compound as compared to the level obtained using a control sample not treated with the test compound can indicate that that test compound is a compound that reduces the ability of Bcl2L12 polypeptides to inhibit caspase-9 activation.

These methods can be used to identify compounds exhibiting any level of reduction. For example, compounds exhibiting a 5, 10, 15, 20, 25, 30, 40, 50, 60, 70, 80, 90, or more percent reduction in the inhibition of caspase-9 activity by Bcl2L12 polypeptides can be identified.

The invention also provides methods for identifying compounds that reduce binding of a Bcl2L12 polypeptide to an Apaf-1 polypeptide. Such methods typically include contacting a sample with a test compound and determining whether or not the presence of the test compound reduces binding of a Bcl2L12 polypeptide to an Apaf-1 polypeptide. Any type of sample and test compound can be used. Typically, the sample contains a Bcl2L12 polypeptide and an Apfa-1 polypeptide. For example, the sample can be a cell lysate prepared from cells expressing both Bcl2L12 and Apaf-1 polypeptides.

Any method can be used to determine whether or not a test compound reduces binding of a Bcl2L12 polypeptide to an Apaf-1 polypeptide. Standard molecular and biochemical techniques (e.g., SDS-PAGE, Western blots, immunostaining, ELISA, and immunoprecipitation) can be used to measure the level of Bcl2L12 polypeptide binding to an Apaf-1 polypeptide. For example, anti-Apaf-1 or anti-Bcl2L12 antibodies can be used in conjunction with gel electrophoresis to detect the amount of Apaf-1-Bcl2L12 polypeptide complexes present within a sample. Alternatively, anti-Apaf-1 or anti-Bcl2L12 antibodies can be used in standard immunoprecipitation assays to assess the binding of between Bcl2L12 and Apaf-1 polypeptides. In some cases, antibodies against epitope tags (e.g., anti-V5 or anti-HA antibodies) can be used when the Bcl2L12 and/or Apaf-1 polypeptides are engineered to contain such tags. Likewise, Bcl2L12 and/or Apaf-1 polypeptides can be made as fusion proteins with, for example, GST such that an immunoprecipitation assay can be performed using, for example, glutathione-coated beads. In each case, a decrease in the level of binding between Bcl2L12 and Apaf-1 polypeptides observed in a sample containing a test compound as compared to the level observed in a control sample not treated with the test compound can indicate that the test compound is a compound that reduces the ability of Bcl2L12 polypeptides to bind Apaf-1 polypeptides. These methods can be used to identify compounds exhibiting any level of reduction. For example, compounds exhibiting a 5, 10, 15, 20, 25, 30, 40, 50, 60, 70, 80, 90, or more percent reduction in binding between Bcl2L12 and Apaf-1 polypeptides can be identified.

In addition, the invention provides methods for identifying compounds that reduce the anti-apoptotic activity of a Bcl2L12 polypeptide. Such methods typically include contacting a sample with a test compound, treating the sample with an apoptotic stimulus, and determining whether or not the presence of the test compound reduces the anti-apoptotic activity of a Bcl2L12 polypeptide. An apoptotic stimulus is any stimulus that triggers apoptosis in cells. Examples of apoptotic stimuli include, without limitation, treatments with radiation (e.g., γ-irradiation) or chemicals (e.g., STS). Any type of sample and test compound can be used. Typically, the sample contains whole cells expressing a Bcl2L12 polypeptide. For example, the sample can be Ink4a/Arf deficient astrocytes transfected with a vector that over-expresses a Bcl2L12 polypeptide. Other cells that can be used include, without limitation, glioma cells (e.g., human gliomas) and melanocytes.

Any method can be used to determine whether or not a test compound reduces the anti-apoptotic activity of a Bcl2L12 polypeptide. For example, standard cell biology techniques can be used to monitor the level of apoptosis in cells. Such techniques include, without limitation, annexin V binding assays and DNA fragmentation assays. For example, annexin V can be used to measure the degree of apoptosis in a population of cells. Likewise, the degree of DNA fragmentation can be measured to determine the degree of apoptosis. In addition, apoptosis can be monitored using flourometric caspase activity assays. For example, a caspase-3 activity assay can be performed using DEVD-AFC peptides. In each case, an increase in the level of apoptosis in a sample containing the test compound as compared to the level obtained using a control sample not treated with the test compound can indicate that the test compound is a compound that reduces the anti-apoptotic activity of a Bcl2L12 polypeptide. These methods can be used to identify compounds exhibiting any level of reduction. For example, compounds exhibiting a 5, 10, 15, 20, 25, 30, 40, 50, 60, 70, 80, 90, or more percent reduction in the anti-apoptotic activity of a Bcl2L12 polypeptide can be identified.

In addition, the invention provides methods for identifying compounds that reduce the pro-necrosis activity of a Bcl2L12 polypeptide. Such methods typically include contacting a sample with a test compound, treating the sample with an apoptotic stimulus, and determining whether or not the presence of the test compound reduces the pro-necrosis activity of a Bcl2L12 polypeptide. Any type of sample and test compound can be used. Typically, the sample contains whole cells expressing a Bcl2L12 polypeptide. For example, the sample can be Ink4a/Arf deficient astrocytes transfected with a vector that over-expresses a Bcl2L12 polypeptide. Other cells that can be used include, without limitation, glioma cells (e.g., human gliomas) and melanocytes.

Any method can be used to determine whether or not a test compound reduces the pro-necrosis activity of a Bcl2L12 polypeptide. For example, standard cell biology techniques can be used to monitor the level of necrosis in cells by measuring nuclear swelling, plasma membrane integrity, and/or mitochondrial membrane potentials. Nuclear swelling can be measured using propidium iodide to determine that percent of cells having nuclei with an increased forward scatter (i.e., increased size). Plasma membrane integrity can be measured using a combination of Hoechst (a DNA intercalating dye that enters living as well as apoptotic or necrotic cells) and SYTOX Green (a green fluorescent dye that only enters cells with a disintegrated plasma membrane). Mitochondrial membrane potential ($\Delta\Psi_M$) can be measured using JC-1, which is a green-fluorescent probe that exists as a monomer at low concentrations or at low membrane potential. At higher concentrations or higher potentials, JC-1 forms red-fluorescent "J-aggregates" that exhibit a broad excitation spectrum and an emission maximum at ~590 nm. Thus, the emission of this cyanine dye can be used as a sensitive measure of mitochondrial membrane potential.

In each case, a decrease in the level of necrosis in a sample containing the test compound as compared to the level obtained using a control sample not treated with the test compound can indicate that the test compound is a compound that reduces the pro-necrosis activity of a Bcl2L12 polypeptide. These methods can be used to identify compounds exhibiting any level of reduction. For example, compounds exhibiting a 5, 10, 15, 20, 25, 30, 40, 50, 60, 70, 80, 90, or more percent reduction in the pro-necrosis activity of a Bcl2L12 polypeptide can be identified.

The invention also provides methods for identifying compounds that reduce Bcl2L12 polypeptide-induced phosphorylation of a MAP kinase polypeptide. Such methods typically include contacting a sample with a test compound and determining whether or not the presence of the test compound reduces the level of phosphorylation of a MAP kinase polypeptide. Any type of sample and test compound can be used. Typically, the sample contains a Bcl2L12 polypeptide and a MAP kinase polypeptide. For example, the sample can be a cell lysate prepared from cells expressing both Bcl2L12 and MAP kinase polypeptides.

Any method can be used to determine whether or not a test compound reduces the level of phosphorylation of a MAP kinase polypeptide. Standard molecular and biochemical techniques (e.g., SDS-PAGE, Western blots, immunostaining, ELISA, and immunoprecipitation) can be used to measure the level of phosphorylation of a MAP kinase polypeptide. For example, anti-phosphotyrosine antibodies can be used to measure the level of phosphorylation of a MAP kinase polypeptide. Alternatively, $^{32}$P labeling assays can be used to assess the level of phosphorylation of a MAP kinase polypeptide. In each case, a decrease in the level of phosphorylation of a MAP kinase polypeptide observed in a sample containing a test compound as compared to the level observed in a control sample not treated with the test compound can indicate that the test compound is a compound that reduces the ability of Bcl2L12 polypeptides to induce phosphorylation of a MAP kinase polypeptide. These methods can be used to identify compounds exhibiting any level of reduction. For example, compounds exhibiting a 5, 10, 15, 20, 25, 30, 40, 50, 60, 70, 80, 90, or more percent reduction in the ability of Bcl2L12 polypeptides to induce phosphorylation of a MAP kinase polypeptide can be identified.

The invention also provides methods for identifying compounds that inhibit cell proliferation and/or cell transformation. Such methods typically include contacting a sample with a test compound and determining whether or not the presence of the test compound reduces cell proliferation and/or cell transformation. Any type of sample and test compound can be used. Typically, the sample contains whole cells expressing a Bcl2L12 polypeptide. For example, the sample can be cells containing an isolated nucleic acid encoding a Bcl2L12 polypeptide.

Any method can be used to determine whether or not a test compound reduces cell proliferation and/or cell transformation. For example, standard cell biology techniques can be used to monitor the growth characteristics of cells. Such techniques include, without limitation, counting cells, measuring foci formation, and assessing growth rates. In each case, a decrease in the level of cell proliferation and/or cell transformation in a sample containing the test compound as compared to the level obtained using a control sample not treated with the test compound can indicate that the test compound is a compound that reduces cell proliferation and/or cell transformation. These methods can be used to identify compounds exhibiting any level of reduction. For example, compounds exhibiting a 5, 10, 15, 20, 25, 30, 40, 50, 60, 70, 80, 90, or more percent reduction in cell proliferation and/or cell transformation can be identified.

The invention also provides methods for identifying compounds that reduce binding of a Bcl2L12 polypeptide to a p53 polypeptide. Such methods typically include contacting a sample with a test compound and determining whether or not the presence of the test compound reduces binding of a Bcl2L12 polypeptide to a p53 polypeptide. Any type of sample and test compound can be used. Typically, the sample contains a Bcl2L12 polypeptide and a p53 polypeptide. For example, the sample can be a cell lysate prepared from cells expressing both Bcl2L12 and p53 polypeptides.

Any method can be used to determine whether or not a test compound reduces binding of a Bcl2L12 polypeptide to a p53 polypeptide. Standard molecular and biochemical techniques (e.g., SDS-PAGE, Western blots, immunostaining, ELISA, and immunoprecipitation) can be used to measure the level of Bcl2L12 polypeptide binding to a p53 polypeptide. For example, anti-p53 or anti-Bcl2L12 antibodies can be used in conjunction with gel electrophoresis to detect the amount of p53-Bcl2L12 polypeptide complexes present within a sample. Alternatively, anti-p53 or anti-Bcl2L12 antibodies can be used in standard immunoprecipitation assays to assess the binding of between Bcl2L12 and p53 polypeptides. In some cases, antibodies against epitope tags (e.g., anti-V5 or anti-HA antibodies) can be used when the Bcl2L12 and/or p53 polypeptides are engineered to contain such tags. Likewise, Bcl2L12 and/or p53 polypeptides can be made as fusion proteins with, for example, GST such that an immunoprecipitation assay can be performed using, for example, glutathione-coated beads. In each case, a decrease in the level of binding between Bcl2L12 and p53 polypeptides observed in a sample containing a test compound as compared to the level observed in a control sample not treated with the test compound can indicate that the test compound is a compound that reduces the ability of Bcl2L12 polypeptides to bind p53 polypeptides. These methods can be used to identify compounds exhibiting any level of reduction. For example, compounds exhibiting a 5, 10, 15, 20, 25, 30, 40, 50, 60, 70, 80, 90, or more percent reduction in the ability of Bcl2L12 polypeptides to bind p53 polypeptides can be identified.

The invention also provides methods for identifying compounds that reduce the ability of a Bcl2L12 polypeptide to inhibit p53 polypeptide driven transcription. Such methods typically include contacting a sample with a test compound and determining whether or not the presence of the test compound reduces the ability of a Bcl2L12 polypeptide to inhibit p53 polypeptide driven transcription. Any type of sample and test compound can be used. Typically, the sample contains a Bcl2L12 polypeptide and a p53 polypeptide. For example, the sample can be a cell lysate prepared from cells expressing both Bcl2L12 and p53 polypeptides.

Any method can be used to determine whether or not a test compound reduces the ability of a Bcl2L12 polypeptide to inhibit p53 polypeptide driven transcription. Standard molecular and biochemical techniques (e.g., SDS-PAGE, Western blots, immunostaining, ELISA, and immunoprecipitation) can be used to measure the level of transcription of a sequence regulated by a p53 polypeptide. For example, a sample can be designed to contain an isolated nucleic acid encoding a detectable marker polypeptide (e.g., a luciferase polypeptide) under the control of a promoter sequence recognized by p53 (e.g., a Bax promoter or a dimerized p53 binding domain such as PG13) as described elsewhere (see, e.g., Kong et al., *J. Biol. Chem.*, 276:32990-33000 (2001)). In this case, an increase in the level of the detectable marker polypeptide can indicate that a p53 polypeptide is available to drive transcription. Thus, an increase in the level of a detectable marker polypeptide observed in a sample containing a test compound as compared to the level observed in a control sample not treated with the test compound can indicate that the test compound is a compound that reduces the ability of a Bcl2L12 polypeptide to inhibit p53 polypeptide driven transcription. These methods can be used to identify compounds exhibiting any level of reduction. For example, compounds exhibiting a 5, 10, 15, 20, 25, 30, 40, 50, 60, 76, 80, 90, or more percent reduction in the ability of a Bcl2L12 polypeptide to inhibit p53 polypeptide driven transcription can be identified.

The methods provided herein describing the identification of inhibitors can be modified to identify activators. Likewise, the methods provided herein describing the identification of activators can be modified to identify inhibitors.

The test compounds used in the methods provided herein can be any type of molecule having any chemical structure. For example, a test compound can be a polypeptide (e.g., an antibody), carbohydrate, small molecule compound, lipid, amino acid, ester, alcohol, carboxylic acid, nucleic acid, fatty acid, or steroid. In addition, test compounds can be lipophilic, hydrophilic, hydrophobic, plasma membrane permeable, or plasma membrane impermeable. Typically, a test compound is an organic molecule (e.g., small organic molecule) such as those typically contained in large organic molecule libraries provided by, for example, Abbott Laboratories or Harvard's Institute of Chemistry and Cell Biology—Initiative for Chemical Genetics (ICCB-ICG).

Any method can be used to contact a sample with a test compound. For example, the sample and test compound can be combined to form a sample-test compound mixture that is in the form a liquid or solid. Typically, a test compound is used in an amount large enough to test its effectiveness. Such amounts can be between about 1 ng/mL to about 10 g/mL. For example, about 10 ng, 50 ng, 100 ng, 250 ng, 500 ng, 750 ng, 1 µg, 10 µg, 50 µg, 100 µg, 250 µg, 500 µg, 750 µg, 1 mg, 10 mg, 50 mg, 100 mg, 250 mg, 500 mg, 750 mg, or 1 g per mL of test compound can be used. In some embodiments, multiple test compounds can be contacted with a single sample. For example, 12 different test compounds can be incubated with a sample in one well of a 96-well plate. In this case, if a positive result is obtained, a separate analysis can be performed using each of the 12 test compounds separately to identify the test compound exhibiting the desired result.

The samples described herein can contain any component. For example, a sample to be contacted with a test compound can contain, without limitation, Bcl2L12 polypeptides (e.g., full-length Bcl2L12 or Bcl2L12-ΔBH2 polypeptides with or without tags such as V5, HA, GFP, or GST), caspase polypeptides (e.g., caspase-1, caspase-2, caspase-3, caspase-4, caspase-5, caspase-6, caspase-7, caspase-8, and/or caspase-9 polypeptides), Apaf-1 polypeptides, cytochrome c polypeptides, p53 polypeptides, MAP kinase polypeptides (e.g., Erk1 and/or Erk2 polypeptides), polypeptide substrates for caspase polypeptides, and dATP.

A Bcl2L12 polypeptide is any polypeptide that exhibits one or more of the Bcl2L12 activities described herein and either (1) contains an amino acid sequence having a length of about 50, 60, 70, 80, 90, 100, 110, 120, 130, 140, 150, 160, 170, 180, 190, 200, 210, 220, 230, 240, 250, 260, 270, 280, 290, 300, 310, 320, 330, or more amino acid residues with at least about 50, 55, 60, 65, 70, 75, 80, 85, 90, 95, or more percent identity over that length to the amino acid sequence set forth in SEQ ID NO:1 or 2, or (2) contains about 50, 60, 70, 80, 90, 100, 110, 120, 130, 140, 150, 160, 170, 180, 190, 200, 210, 220, 230, 240, 250, 260, 270, 280, 290, 300, 310, 320, 330, or more consecutive amino acid residues encoded by a nucleic acid sequence that hybridizes, under hybridization conditions (see below), to the sense or antisense strand of a nucleic acid encoding the sequence set forth in SEQ ID NO:1 or 2.

The length and percent identity over that length for any amino acid sequence is determined as follows. First, an amino acid sequence is compared to the identified amino acid sequence (e.g., SEQ ID NO:1) using the BLAST 2 Sequences (Bl2seq) program from the stand-alone version of BLASTZ containing BLASTN version 2.0.14 and BLASTP version 2.0.14. This stand-alone version of BLASTZ can be obtained from Fish & Richardson P.C.'s web site ("fr" dot "com/blast/" on the World Wide Web) or the U.S. government's National Center for Biotechnology Information web site ("ncbi" dot "nlm" dot "nih" dot "gov" on the World Wide Web). Instructions explaining how to use the Bl2seq program can be found in the readme file accompanying BLASTZ. Bl2seq performs a comparison between two sequences using either the BLASTN or BLASTP algorithm. BLASTN is used to compare nucleic acid sequences, while BLASTP is used to compare amino acid sequences. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq -i c:\seq1.txt -j c:\seq2.txt -p blastp -o c:\output.txt. If the target sequence shares homology with any portion of the identified sequence, then the designated output file will present those regions of homology as aligned sequences. If the target sequence does not share homology with any portion of the identified sequence, then the designated output file will not present aligned sequences. Once aligned, a length is determined by counting the number of consecutive amino acid residues from the target sequence presented in alignment with sequence from the identified sequence (e.g., SEQ ID NO:1) starting with any matched position and ending with any other matched position. A matched position is any position where an identical amino acid residue is presented in both the target and identified sequence. Gaps presented in the target sequence are not counted since gaps are not amino acid residues. Likewise, gaps presented in the identified sequence are not counted since target sequence amino acid residues are counted, not amino acid residues from the identified sequence.

The percent identity over a determined length is determined by counting the number of matched positions over that length and dividing that number by the length followed by multiplying the resulting value by 100. For example, if (1) a 500 amino acid target sequence is compared to the sequence set forth in SEQ ID NO:1, (2) the Bl2seq program presents 200 amino acid residues from the target sequence aligned with a region of the sequence set forth in SEQ ID NO:1 where the first and last amino acid residues of that 200 amino acid region are matches, and (3) the number of matches over those 200 aligned amino acids is 180, then the 500 amino acid target sequence contains a length of 200 and a percent identity over that length of 90 (i.e., 180÷200*100=90).

It will be appreciated that a single amino acid target sequence that aligns with the sequence set forth in SEQ ID NO:1 can have many different lengths with each length having its own percent identity. It is noted that the percent identity value is rounded to the nearest tenth. For example, 78.11, 78.12, 78.13, and 78.14 is rounded down to 78.1, while 78.15, 78.16, 78.17, 78.18, and 78.19 is rounded up to 78.2. It is also noted that the length value will always be an integer.

The hybridization conditions can be moderately or highly stringent hybridization conditions. For the purpose of this invention, moderately stringent hybridization conditions mean the hybridization is performed at about 42° C. in a hybridization solution containing 25 mM $KPO_4$ (pH 7.4), 5×SSC, 5× Denhart's solution, 50 μg/mL denatured, sonicated salmon sperm DNA, 50% formamide, 10% Dextran sulfate, and 1-15 ng/mL probe (about $5 \times 10^7$ cpm/μg), while the washes are performed at about 50° C. with a wash solution containing 2×SSC and 0.1% sodium dodecyl sulfate.

Highly stringent hybridization conditions mean the hybridization is performed at about 42° C. in a hybridization solution containing 25 mM $KPO_4$ (pH 7.4), 5×SSC, 5× Denhart's solution, 50 μg/mL denatured, sonicated salmon sperm DNA, 50% formamide, 10% Dextran sulfate, and 1-15 ng/mL probe (about $5 \times 10^7$ cpm/μg), while the washes are performed at about 65° C. with a wash solution containing 0.2×SSC and 0.1% sodium dodecyl sulfate.

Caspase polypeptides (e.g., caspase-1, caspase-2, caspase-3, caspase-4, caspase-5, caspase-6, caspase-7, caspase-8, and/or caspase-9 polypeptides), Apaf-1 polypeptides, cytochrome c polypeptides, p53 polypeptides, and MAP kinase polypeptides (e.g., Erk1 and/or Erk2 polypeptides) can be obtained using any method and can have an amino acid sequence as set forth in the appropriate GenBank® accession number. For example, an Apaf-1 polypeptide can have the amino acid sequence set forth in GenBank® accession number O14727.

In some cases, the sample can be a cell lysate prepared from cells expressing, for example, Bcl2L12, caspase-9, Apaf-1, and/or cytochrome c polypeptides. Such cells can express one or more polypeptide endogenously or can contain isolated nucleic acid that encodes one or more polypeptide. Examples of cells endogenously expressing Bcl2L12 and caspase-9 polypeptides include, without limitation, human glioma cells (e.g., U87MG cells) and melanocytes.

Any cell can be given isolated nucleic acid encoding, for example, Bcl2L12, caspase, Apaf-1, cytochrome c, p53, and/or MAP kinases polypeptides. Typically, the isolated nucleic acid is designed to contain a promoter sequence that drives expression of the one or more encoded polypeptides. An isolated nucleic acid can contain any polypeptide-encoding sequence operably linked to any promoter sequence. For example, an isolated nucleic acid can be designed to encode a Bcl2L12 polypeptide under the control of an inducible promoter system such as the tetracycline-regulated promoter system described elsewhere (See, e.g., PCT/US02/09710). In this case, administering an inducing agent (e.g., tetracycline or doxycycline) to a cell containing the isolated nucleic acid can result in expression of a Bcl2L12 polypeptide. The promoter sequence can be a constitutive promoter sequence (e.g., the cytomegalovirus (CMV) promoter sequence) or a tissue-specific promoter sequence (e.g., a tyrosinase promoter sequence to express a polypeptide in a melanoma cell; a TRP2 promoter sequence to express a polypeptide in a melanocytes; an MMTV or WAP promoter sequence to express a polypeptide in breast cells and/or cancers; a Villin or FABP promoter sequence to express a polypeptide in intestinal cells and/or cancers; a RIP promoter sequence to express a polypeptide in pancreatic beta cells; a Keratin promoter sequence to express a polypeptide in keratinocytes; a Probasin promoter sequence to express a polypeptide in prostatic epithelium; a nestin or GFAP promoter sequence to express a polypeptide in CNS cells and/or cancers; a tyrosine hydroxylase sequence or S100 promoter to express a polypeptide in neurons; and an Alpha myosin promoter sequence to express a polypeptide in cardiac cells).

The term "nucleic acid" as used herein encompasses both RNA and DNA, including cDNA, genomic DNA, and synthetic (e.g., chemically synthesized) DNA. The nucleic acid can be double-stranded or single-stranded. Where single-stranded, the nucleic acid can be the sense strand or the antisense strand. In addition, nucleic acid can be circular or linear.

The term "isolated" as used herein with reference to nucleic acid refers to a naturally-occurring nucleic acid that is not immediately contiguous with both of the sequences with which it is immediately contiguous (one on the 5' end and one on the 3' end) in the naturally-occurring genome of the organism from which it is derived. For example, an isolated nucleic acid can be, without limitation, a recombinant DNA molecule of any length, provided one of the nucleic acid sequences normally found immediately flanking that recombinant DNA molecule in a naturally-occurring genome is removed or absent. Thus, an isolated nucleic acid includes, without limitation, a recombinant DNA that exists as a separate molecule (e.g., a cDNA or a genomic DNA fragment produced by PCR or restriction endonuclease treatment) independent of other sequences as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated nucleic acid can include a recombinant DNA molecule that is part of a hybrid or fusion nucleic acid sequence.

The term "isolated" as used herein with reference to nucleic acid also includes any non-naturally-occurring nucleic acid since non-naturally-occurring nucleic acid sequences are not found in nature and do not have immediately contiguous sequences in a naturally-occurring genome. For example, non-naturally-occurring nucleic acid such as an engineered nucleic acid is considered to be isolated nucleic acid. Engineered nucleic acid can be made using common molecular cloning or chemical nucleic acid synthesis techniques. Isolated non-naturally-occurring nucleic acid can be independent of other sequences, or incorporated into a vector, an autonomously replicating plasmid, a virus (e.g., a retrovirus, adenovirus, or herpes virus), or the genomic DNA of a prokaryote or eukaryote. In addition, a non-naturally-occurring nucleic acid can include a nucleic acid molecule that is part of a hybrid or fusion nucleic acid sequence.

It will be apparent to those of skill in the art that a nucleic acid existing among hundreds to millions of other nucleic acid molecules within, for example, cDNA or genomic libraries, or gel slices containing a genomic DNA restriction digest is not to be considered an isolated nucleic acid.

An isolated nucleic acid can be obtained using any method including, without limitation, common molecular cloning and chemical nucleic acid synthesis techniques. For example, PCR can be used to obtain an isolated nucleic acid encoding a Bcl2L12 polypeptide, an Apaf-1, a caspase polypeptide (e.g., caspase-9 polypeptide), a cytochrome c polypeptide, a p53 polypeptide, or a MAP kinase polypeptide (e.g., Erk1 and/or Enk2 polypeptides). PCR includes procedures in which target nucleic acid is amplified in a manner similar to that described in U.S. Pat. No. 4,683,195. Typically, sequence information from the ends of the region of interest or beyond are used to design oligonucleotide primers that are identical or similar in sequence to opposite strands of a potential template to be amplified. Using PCR, a nucleic acid sequence can be amplified from RNA or DNA. For example, a nucleic acid sequence can be isolated by PCR amplification from total cellular RNA, total genomic DNA, and cDNA as well as from bacteriophage sequences, plasmid sequences, viral sequences, and the like. When using RNA as a source of template, reverse transcriptase can be used to synthesize complimentary DNA strands.

Any method can be used to introduce isolated nucleic acid into a cell. For example, calcium phosphate precipitation, electroporation, heat shock, lipofection, microinjection, and viral-mediated nucleic acid transfer can be used introduce isolated nucleic acid into cells. In addition, naked DNA can be delivered directly to cells in vivo as describe elsewhere (U.S. Pat. Nos. 5,580,859 and 5,589,466). Further, isolated nucleic acid can be introduced into cells by generating transgenic non-human animals (e.g., transgenic mice, rats, pigs, sheep, rabbits, and non-human primates such as baboons, monkeys, and chimpanzees).

In addition, the samples described herein can contain whole cells (e.g., cell cultures or tissue sections), cell lysates, or purified polypeptides. For example, a sample can contain whole cells or lysates of cells that are of the same type (e.g., a clonal population). Alternatively, a sample can contain whole cells or lysates of cells that are a mixture of different cell types. In some cases, a sample can contain one or more purified polypeptides. For example, a sample can contain several different purified polypeptides (e.g., Apaf-1, cytochrome c, and caspase-9 polypeptides) that have been combined to reconstitute a particular activity (e.g., caspase-9 activation).

The methods and materials provided herein can be used to perform high-throughput screens of chemical libraries such as those available at Abbott Laboratories or Harvard's ICCB-ICG. For example, chemical libraries, robotic compound transfer systems, liquid handling equipment, plate readers, and screening microscopes can be used to perform the methods described herein in a high-throughput screen format. In some cases, the screens can be performed using 384-well plates. Typically, chemical libraries contain a collection of thousands of small molecules (e.g., over 200,000 small molecules). A high-throughput screen can be performed in any manner such as described elsewhere (Jiang et al., *Science*, 299:223-226 (2003), including the Supplementary Information).

In one embodiment, a high-throughput screen can be used to identify small organic compounds that release Bcl2L12 polypeptide's block of caspase-9 activation. This high-throughput screen assay can monitor the activation of caspase-9 upon cytochrome c/dATP activation of Apaf-1 using a colorimetric caspase-9-specific polypeptide substrate, Ac-LEHD-pNA. Briefly, lysates from Ink4a/Arf$^{-/-}$ astrocytes stably over-expressing a Bcl2L12 polypeptide (e.g., full-length Bcl2L12 or Bcl2L12-ΔBH2 polypeptide) can be prepared. Typically, adding cytochrome c and dATP induces caspase-9 activation. As described herein, however, the presence of a Bcl2L12 polypeptide can block caspase-9 activation. Test compounds can be added to the lysates to determine whether or not the test compound released Bcl2L12 polypeptide's block of caspase-9 activation. Typically, lysates are added to plates that contain 12 small organic compounds per well. The screening plates can be read, and the change of absorbency can be scaled to a positive control (e.g., lysates from Ink4a/Arf$^{-/-}$ astrocytes lacking Bcl2L12 polypeptide expression and lacking the test compound) and/or a negative control (e.g., lysates from Ink4a/Arf$^{-/-}$ astrocytes over-expressing the Bcl2L12 polypeptide but lacking the test compound). The test compounds in wells exhibiting an increase in signal (e.g., a 5, 10, 15, 20, 30, 40, 50, 60, 70, 80, 90, 100, 150, 200, or more percent increase in signal) as compared to a negative control can be retested separately. Screening results can be analyzed using an Oracle database, allowing structure sub-searching of assay data and comparison of assay results.

In another embodiment, a high-throughput screen can be used to identify small molecules that specifically inhibit the ability of Bcl2L12 polypeptides to inhibit p53-dependent transcription. Briefly, total cellular lysates from astrocytes over-expressing a Bcl2L12 polypeptide and containing an isolated nucleic acid encoding a luciferase polypeptide under the control of a promoter sequence recognized by p53 (e.g., a Bax promoter or a dimerized p53 binding domain such as PG13) can be obtained. These lysates can be added to plates that contain 12 small organic compounds per well. After a incubation period (e.g., about 6, 12, 24, 48, 72 hours or more), the screening plates can be read for luciferase activity. The obtained signals can be scaled to a positive control (e.g., lysates from astrocytes lacking Bcl2L12 polypeptide expression and lacking the test compounds) and/or a negative control (e.g., lysates from astrocytes over-expressing the Bcl2L12 polypeptide but lacking the test compound). The test compounds in wells exhibiting an increase in signal (e.g., a 5, 10, 15, 20, 30, 40, 50, 60, 70, 80, 90, 100, 150, 200, or more percent increase in signal) as compared to a negative control can be retested separately. Screening results can be analyzed using an Oracle database, allowing structure sub-searching of assay data and comparison of assay results.

Compounds identified using any of the methods or materials provided herein can be tested for an anti-cancer effect using any method. For example, identified compounds can be administered to cancer cells or an animal (e.g., mouse, rat, rabbit, monkey, or human) containing cancer cells. Any route of administration can be used. For example, an identified compound can be administered systemically, intravenously, intraperitoneally, intramuscularly, subcutaneously, intracranially, intrathecally, intradermally, or orally. In addition, any amount of the identified compound can be administered. In the case of animals, an identified compound is typically administered in an amount large enough to ensure significant delivery of the identified compound to the tumor cells without causing significant adverse side effects to the animal. Standard pharmacological studies can be performed to assess the amount of identified compound being delivered to the tumor cells for a given amount administered. Based on these studies, the amount administered can be increased or decrease.

Any method can be used to determine whether or not the administered identified compound induces an anti-cancer effect (e.g., reduction in the number of tumor cells within the animal). When using tumor cells in culture, the cells can be assessed for growth characteristics, apoptosis, and/or necrosis. For solid tumors in vivo, the diameter of the tumor can be measured before and after administration. Such measurements can be made using a caliper when the tumor has a dermal location. When the tumor occurs in a visceral cavity (e.g., liver or lung) or intracranially (e.g., within the brain), imaging techniques such as contrast enhanced computed tomography (CT) or magnetic resonance imaging (MRI) can be used to measure the size of tumors. Reductions in other types of tumor cells in vivo can be assessed using histological, biochemical, immunological, or clinical techniques. For example, histological techniques can be used to determine whether or not tumor cells remain in a particular tissue. Likewise, clinical techniques can be used determine the health of an animal thereby assessing the stage of cancer progression. If cancer progression stops or is reversed, then the number of tumor cells within the animal was, most likely, reduced. Additional studies can be used to confirm an anti-caner effect such as flow assisted cell sorting (FACS) or in vivo fluorescent imaging from cells genetically altered to express, for example, luciferase activity.

The invention also provides methods for treating a mammal having cancer cells that express a Bcl2L12 polypeptide. Such methods can involve administering a compound to the mammal under conditions wherein the compound results in a reduced Bcl2L12 polypeptide activity. A reduction in a Bcl2L12 polypeptide activity can result in reduced cancer cell growth, reduced tumorigenicity, or reduced tumor maintenance. For example, a compound capable of reducing a Bcl2L12 polypeptide activity can be used to reduce the number of cancer cells in a mammal by, for example, at least 10, 20, 30, 40, 50, 60, 70, 80, 90, or more percent (e.g., between 10 and 90 percent; between 10 and 75 percent; between 10 and 50 percent; between 50 and 95 percent; between 60 and 95 percent; or between 75 and 95 percent). In some embodiments, a compound capable of reducing a Bcl2L12 polypeptide activity can be used to reduce the number of cancer cells in a mammal by 100 percent. Any method can be used to determine the percent reduction in cancer cells within a mammal. For example, imaging techniques such as contrast enhanced CT or MRI can be used to assess reduction in cancer cells. In some cases, reductions in cancer cells can be assessed using histological, biochemical, immunological, or clinical techniques. For example, histological techniques can be used to determine whether or not tumor cells remain in a particular tissue.

In some embodiments, a compound capable of reducing a Bcl2L12 polypeptide activity can be used to reduce the mass of a tumor in a mammal by, for example, at least 10, 20, 30, 40, 50, 60, 70, 80, 90, 95, or more percent (e.g., between 10 and 90 percent; between 10 and 75 percent; between 10 and 50 percent; between 50 and 95 percent; between 60 and 95 percent; between 75 and 95 percent; or between 90 and 100 percent). Any method can be used to determine a reduction in the mass of a tumor within a mammal. For example, imaging techniques such as contrast enhanced CT or MRI can be used to assess a reduction in a tumor.

Any type of cancer cell that exhibits the anti-apoptotic activity of a Bcl2L12 polypeptide can be treated with a compound that results in a reduced Bcl2L12 polypeptide activity such that cancer cell growth, tumorigenicity, or tumor maintenance is reduced. Such cancer cells can be gliomas, bone cancer cells, cervical cancer cells, colon cancer cells, gastrointestinal cancer cells, ovarian cancer cells, pancreatic cancer cells, stomach cancer cells, and testicular cancer cells. In addition, any mammal having such a cancer cell can be treated including, without limitation, humans, rodents (e.g., rats and mice), goats, pigs, horses, sheep, dogs, cats, cows, and monkeys.

Any compound having the ability to reduce a Bcl2L12 polypeptide activity can be used to treat a mammal having cancer cells. For example, antisense oligonucleotides, siRNA molecules, RNAi constructs, and PNA oligomers can be designed and used to reduce the level of Bcl2L12 polypeptides expressed in cells (e.g., cancer cells). In addition, molecules (e.g., small molecule inhibitors or fragments of an Apaf-1 polypeptide) that bind to a Bcl2L12 polypeptide and inhibit a Bcl2L12 polypeptide activity can be used to treat a mammal having cancer cells. Molecules such as fragments of a Bcl2L12 polypeptide that compete against a full-length Bcl2L12 polypeptide for binding to a binding partner of a Bcl2L12 polypeptide (e.g., Apaf-1) can be used to treat a mammal having cancer cells. Such molecules can be identified using any of the methods and materials provided herein. For example, an organic small molecule capable of inhibiting a Bcl2L12 polypeptide activity can be identified by screening a small molecule library for molecules having the ability to reduce the anti-apoptotic activity of a Bcl2L12 polypeptide.

Any method can be used to deliver a nucleic acid molecule such as a Bcl2L12 antisense oligonucleotide or Bcl2L12 RNAi construct to a cell. For example, liposomes or lipids can be loaded or complexed with nucleic acid to form nucleic acid-liposome or nucleic acid-lipid complexes. The liposome can be composed of cationic and neutral lipids commonly used to transfect cells in vitro. Cationic lipids can complex (e.g., charge-associate) with negatively charged nucleic acids to form liposomes. Examples of cationic liposomes include lipofectin, lipofectamine, lipofectace, and DOTAP. Procedures for forming liposomes are well known in the art. Liposome compositions can be formed, for example, from phosphatidylcholine, dimyristoyl phosphatidylcholine, dipalmitoyl phosphatidylcholine, dimyristoyl phosphatidylglycerol, or dioleoyl phosphatidylethanolamine. Numerous lipophilic agents are commercially available, including Lipofectin® (Invitrogen/Life Technologies, Carlsbad, Calif.) and Effectene™ (Qiagen, Valencia, Calif.).

In some embodiments, systemic delivery is optimized using commercially available cationic lipids such as DDAB or DOTAP, each of which can be mixed with a neutral lipid such as DOPE or cholesterol. In some cases, liposomes such as those described by Templeton et al. (*Nature Biotechnology*, 15:647-652 (1997)) can be used. In other embodiments, polycations such as polyethyleneimine can be used to achieve delivery in vivo and ex vivo (Boletta et al., *J. Am Soc. Nephrol.* 7: 1728 (1996)).

The mode of delivery can vary with the targeted cell or tissue. For example, nucleic acids can be delivered to lung and liver via the intravenous injection of liposomes since both lung and liver tissue take up liposomes in vivo. In addition, when treating a localized tumor, catheterization in an artery upstream of the affected organ can be used to deliver liposomes containing nucleic acid. This catheterization can avoid clearance of the liposomes from the blood by the lungs and/or liver. For lesions such as skin cancer, topical delivery of liposomes can be used.

Liposomes containing the nucleic acid provided herein can be administered parenterally, intravenously, intramuscularly, intraperitoneally, transdermally, excorporeally, or topically. The dosage can vary depending on the species, age, weight, condition of the subject, and the particular compound delivered.

In other embodiments, viral vectors can be used to deliver nucleic acid to a desired target cell. Standard molecular biology techniques can be used to introduce a nucleic acid provided herein into one of the many different viral vectors previously developed to deliver nucleic acid to particular cells. These resulting viral vectors can be used to deliver nucleic acid to the targeted cells by, for example, infection.

A compound having the ability to reduce a Bcl2L12 polypeptide activity (e.g., an siRNA molecule, an RNAi nucleic acid construct, or a small molecule Bcl2L12 inhibitor) can be administered in amounts and for periods of time that will vary depending upon the nature of the particular cancer cells, the cancer severity, and the mammal's overall condition. Compounds designed to reduce Bcl2L12 polypeptide expression (e.g., siRNA molecules) can be administered in an amount that effectively reduces production of the targeted Bcl2L12 polypeptide. The ability of a compound to effectively reduce production of a Bcl2L12 polypeptide can be assessed, for example, by measuring mRNA or polypeptide levels in a mammal before and after treatment. Any method can be used to measure mRNA and polypeptide levels in tissues or biological samples such as Northern blots, RT-PCR, immunostaining, ELISAs, and radioimmunoassays. Compounds designed to inhibit a Bcl2L12 polypeptide activity by interacting with either a Bcl2L12 polypeptide or a binding partner of a Bcl2L12 polypeptide can be administered in an amount that effectively inhibits a Bcl2L12 polypeptide activity. The ability of a compound to effectively inhibit a Bcl2L12 polypeptide activity can be assessed, for example, by using any of the activity assays provided herein (e.g., a caspase activity assay).

Dosing is generally dependent on the severity and responsiveness of the cancer to be treated, with the course of treatment lasting from several days to several months, or until a cure is effected or a diminution of the cancer state is achieved. Routine methods can be used to determine optimum dosages, dosing methodologies, and repetition rates. Optimum dosages can vary depending on the relative potency of individual compounds, and can generally be estimated based on $EC_{50}$ values found to be effective in in vitro and/or in vivo animal models. Typically, dosage is from about 0.01 μg to about 100 g per kg of body weight, and can be given once or more daily, weekly, or even less often. Following successful treatment, it may be desirable to have the mammal undergo maintenance therapy to prevent the recurrence of the cancer.

Any method can be used to formulate and subsequently administer a composition containing one or more compounds having the ability to reduce a Bcl2L12 polypeptide activity (e.g., an siRNA molecule or a small molecule Bcl2L12 inhibitor). For example, compositions containing one or more compounds provided herein can be admixed, encapsulated, conjugated, or otherwise associated with other molecules such as, for example, liposomes, receptor targeted molecules, oral formulations, rectal formulations, or topical formulations for assisting in uptake, distribution, and/or absorption.

Compositions containing one or more compounds provided herein can contain one or more pharmaceutically acceptable carriers. A "pharmaceutically acceptable carrier"

is a pharmaceutically acceptable solvent, suspending agent, or any other pharmacologically inert vehicle. Pharmaceutically acceptable carriers can be liquid or solid, and can be selected with the planned manner of administration in mind so as to provide for the desired bulk, consistency, and other pertinent transport and chemical properties. Typical pharmaceutically acceptable carriers include, without limitation, water; saline solution; binding agents (e.g., polyvinylpyrrolidone or hydroxypropyl methylcellulose); fillers (e.g., lactose and other sugars, gelatin, or calcium sulfate); lubricants (e.g., starch, polyethylene glycol, or sodium acetate); disintegrates (e.g., starch or sodium starch glycolate); and wetting agents (e.g., sodium lauryl sulfate).

The compositions can be administered by a number of methods depending upon whether local or systemic treatment is desired and upon the area to be treated. Administration can be, for example, topical (e.g., transdermal, ophthalmic, or intranasal); pulmonary (e.g., by inhalation or insufflation of powders or aerosols); oral; or parenteral (e.g., by subcutaneous, intrathecal, intraventricular, intramuscular, or intraperitoneal injection, or by intravenous drip). Administration can be rapid (e.g., by injection) or can occur over a period of time (e.g., by slow infusion or administration of slow release formulations). For treating tissues in the central nervous system, the composition can be administered by injection or infusion into the cerebrospinal fluid, preferably with one or more agents capable of promoting penetration across the blood-brain barrier.

Compositions for topical administration include, for example, sterile and non-sterile aqueous solutions, non-aqueous solutions in common solvents such as alcohols, or solutions in liquid or solid oil bases. Such solutions also can contain buffers, diluents, and other suitable additives. Compositions for topical administration can be formulated in the form of transdermal patches, ointments, lotions, creams, gels, drops, suppositories, sprays, liquids, and powders. Conventional pharmaceutical carriers, aqueous, powder or oily bases, thickeners, and the like can be added.

Compositions for oral administration include, for example, powders or granules, suspensions or solutions in water or non-aqueous media, capsules, sachets, or tablets. Such compositions also can incorporate thickeners, flavoring agents, diluents, emulsifiers, dispersing aids, or binders. Compositions for parenteral, intrathecal, or intraventricular administration can include, for example, sterile aqueous solutions, which also can contain buffers, diluents, and other suitable additives (e.g., penetration enhancers, carrier compounds, and other pharmaceutically acceptable carriers).

The invention will be further described in the following examples, which do not limit the scope of the invention described in the claims.

EXAMPLES

Example 1

Identifying Bcl2L12 Polypeptide as a Gliomagenic Oncogene Product

The recurrent gains/losses (termed chromosomal numerical aberrations, CNAs) present in the GBM genome were identified using a platform of genome scanning methods. The platform included array-based CGH (array-CGH), scanning sequence-tagged site-PCR (scanning STS-PCR), quantitative RT-PCR, expression, and bioinformatics and was used to obtain a high-resolution genome-wide view of CNAs present in a panel of human GBMs. In particular, combined array-based CGH and STS-PCR were used to identify a 19q13.3-q13.4 gain in GBM. Briefly, a collection of independent human GBM tumor samples (n=14) were subjected to genome-wide array-CGH using a 1094 BAC collection (Spectral Genomics) that provides approximately 3 MB interval coverage of the genome. This analysis identified an 19q13.3-q13.4 amplicon. The relative genomic DNA copy numbers of the predicted and annotated genes within the 19q13.3-q13.4 amplicon were determined using STS-PCR and were normalized with the amplification levels of reference genomic DNA (normal human placental DNA). STS-PCR identified a minimal region (about 0.25 Mb) of the 19q13.3-q13.4 amplicon containing predicted and annotated genes (e.g., Q9NWS0, FLT3LG, FCGRT, Q96D15, Q9Y314, PRRG2, Q9ULL5, R-Ras, IRF3, and Bcl2L12) with an increase in relative copy number for human GBM samples (n=8).

A significant number of the GBM tumor samples were of sufficient quantity to permit semi-quantitative RT-PCR analysis of the predicted and annotated genes residing within the minimal region of the 19q13.3 amplicon. Since the adult brain is composed largely of mature astrocytes (i.e., about eight astrocytes to each neuron), the reference control was total RNA derived from normal adult brain tissue. Briefly, the mRNA expression levels were determined by semi-quantitative RT-PCR using the identical STS primer sets used for STS-PCR and first-strand cDNA that was reverse-transcribed from human GBM total RNAs. RT-PCR products were transferred to Hybond+membrane and visualized by hybridizing the membranes with $P^{32}$-labeled with their corresponding PCR product probes.

Among the nine candidates examined (Q9NWS0, FCGRT, Q96D15, Q9Y314, PRRG2, Q9ULL5, R-Ras, IRF3, and Bcl2L12), all except Q9NWS0 was found to be expressed in human GBM and normal brain tissues. Q9ULL5 was consistently down-regulated in GBM samples when compared to the levels observed in the normal control. Of the remaining seven candidate genes, Bcl2L12 exhibited a dramatic and frequent up-regulation in a majority of GBM samples examined, including GBM samples that did not exhibit an increased Bcl2L12 copy number by STS-PCR assay. This pattern indicates that Bcl2L12 dysregulation can occur via mechanisms other than gene amplification. In contrast, other candidates within this locus did not exhibit consistent overexpression in samples with and without increased copy number. These expression profiles indicated that Bcl2L12 is the target of amplification at 19q13.3-q13.4.

Additional studies of Bcl2L12 were performed to determine whether up-regulated Bcl2L12 mRNA expression is tumor grade-specific. To this end, low-grade astrocytomas were assayed for Bcl2L12 gene copy number and mRNA levels by PCR based methods as described above. Three of the three low-grade astrocytomas examined exhibited a lack of elevated gene dosage and mRNA levels when compared to those levels observed in normal human placental DNA and normal brain RNA. These findings indicate that Bcl2L12 dysregulation can occur at the transition from low- to high-grade disease and may contribute to the biological features of advanced gliomas such as rapid growth and/or intense resistance to apoptotic stimuli, which are characteristics of high grade gliomas.

Example 2

Bcl2L12 Polypeptide Exhibits Pro-proliferative and Pro-survival Activities

The Bcl2L12-V5, R-RAS, and IRF3 nucleic acid sequences were cloned into expression vectors. Controls included expression vectors containing EGFR or Bcl2 nucleic acid sequences. The encoded polypeptides were expressed in primary astrocytes and tested for cell growth, transformation, and apoptosis activities. Primary astrocytes deficient for Ink4a/Arf (e.g., Ink4a$^{-/-}$/Arf$^{-/-}$ astrocytes) were used given the prominence of this tumor suppressor lesion in advanced human gliomas. The following was performed to assess growth characteristics under normal growth conditions. Mouse Ink4a$^{-/-}$/Arf$^{-/-}$ astrocytes were retro-virally transduced with pBabe vector alone; Bcl2L12-V5 nucleic acid; R-RAS nucleic acid; IRF3 nucleic acid; EGFR* nucleic acid; or Bcl2 nucleic acid. After retro-viral infection, transduced mouse Ink4a$^{-/-}$/Arf$^{-/-}$ astrocytes were subjected to puromycin (2 μg/mL) selection for four days and plated at a density of $1 \times 10^5$ cells/10 cm dish using 10% FBS-DMEM medium. All transduced Ink4a$^{-/-}$/Arf$^{-/-}$ astrocytes were counted each day for five days to determine cell numbers (mean±S.D.; three independent experiments with each being performed in triplicate).

The following was performed to assess growth characteristics under low-serum growth conditions. Retro-virally transduced mouse Ink4a$^{-/-}$/Arf$^{-/-}$ astrocytes ($1 \times 10^6$ cells/10 cm dish) were allowed to attach onto plates in 10% FBS-DMEM medium for five hours. After five hours, the medium was changed to 0.1% FBS-DMEM, and the cells were allowed to grow for three days. After three days in 0.1% FBS, the cells were counted to determine cell numbers (mean±S.D.; three independent experiments with each being performed in triplicate). The number of Ink4a$^{-/-}$/Arf$^{-/-}$ astrocytes infected with pBabe-vector was set to 1.0.

Under normal growth conditions, Bcl2L12-V5 polypeptide over-expression resulted in a significant increase in growth when compared to cells transfected with vector only. This increased growth approached the levels observed with cells over-expressing activated EGFR polypeptides (EGFR* polypeptides). In addition, both Bcl2L12-V5- and EGFR*-transduced Ink4a$^{-/-}$/Arf$^{-/-}$ astrocytes were significantly resistant to growth inhibition by the low serum culture (p<0.01; Student t-test) as compared to pBabe-transduced cells.

Over-expression of R-RAS polypeptides resulted in a moderate increase in proliferation when compared to the levels observed in cells transfected with vector only. This increase was observed under normal serum conditions, but not low serum conditions. Cells transfected with the Bcl2 or IRF3 containing vectors or empty vector failed to exhibit a pro-proliferative response.

The following experiments were performed to determine whether the Bcl2L12 polypeptide influenced cell survival or apoptosis. Ink4a$^{-/-}$/Arf$^{-/-}$ astrocytes retro-virally infected with vector alone (pBabe) or vector containing Bcl2 nucleic acid, Bcl2L12-V5 nucleic acid, R-RAS nucleic acid, or IRF3 nucleic acid were seeded at $1 \times 10^6$ cells/10 cm dish and grown in 10% FBS-DMEM containing 100 nM staurosporine for one day. After this one day incubation, the cells were stained with annexin V (Roche). Annexin V-positive cells were determined by FACScan analysis (mean±S.D.; three independent experiments with each being performed in triplicate). Annexin V staining as assessed using FACS analysis revealed a marked increase in survival of Ink4a/Arf–/– astrocyte cultures transduced with Bcl2L12-V5 (about 6-7 percent annexin-V positive cells) or Bcl2 (about 2-3 percent annexin-V positive cells), while R-RAS (about 10-20 percent annexin-V positive cells), IRF3 (about 14-16 percent annexin-V positive cells), and control cultures (about 17-22 percent annexin-V positive cells) remained sensitive. In fact, both Bcl2- and Bcl2L12-V5-transduced Ink4a$^{-/-}$/Arf$^{-/-}$ astrocytes were significantly resistant to staurosporine-induced apoptosis (p<0.01; Student t-test).

The oncogenic potential of these genes was determined directly through their capacity to cooperate with activated H-RAS to effect the malignant transformation of primary Ink4a$^{-/-}$/Arf$^{-/-}$ cells. Briefly, Ink4a$^{-/-}$/Arf$^{-/-}$ mouse embryo fibroblasts (MEFs) were seeded at $8 \times 10^5$ cells/10 cm dish and grown in 10% FBS-DMEM for one day and then cotransfected with 1.5 μg of activated H-Ras$^{G12V}$ and 1.5 μg of either pBabe, Bcl2, Bcl2L12-V5, R-RAS, or IRF3 nucleic acid using Lipopectamine-plus reagent (Invitrogen). One day after cotransfection, each Ink4a$^{-/-}$/ARF$^{-/-}$ MEF was splitted 1:3 ratio and refed with 10% FBS-DMEM every 3-4 day for ten days. After staining cells with crystal violet solution, foci were counted to determine transformation efficiency (mean±S.D.; three independent experiments with each being done in duplicate). The numbers of foci from cells cotransfected with H-Ras$^{G12V}$ and pBabe vector were set to 100%.

Both H-Ras$^{G12V}$+Bcl2 and H-Ras$^{G12V}$+Bcl2L12-V5 exhibited increased foci formation efficiency when compared to the level observed with H-Ras$^{G12V}$+pBabe (p<0.05; Student t-test). In addition, the results with Bcl2L12-V5 and Bcl2 were similar, increasing RAS-induced focus formation by greater than about 1.5 to about 2-fold. In contrast, R-RAS and IRF3 did not exhibit any cooperative activity with H-Ras$^{G12V}$. Taken together, these results indicate that Bcl2L12 is a strong candidate for the 19q13.3 amplification and possesses cancer-relevant pro-proliferative and pro-survival activities.

Expression of Bcl2L12 mRNA in the human GBM cell lines (A1207; LN229; U178; LNZ308; U87) was determined by Northern blot analysis. The human GBM cell lines A1207, LN229, U178, LNZ308, and U87 exhibited Bcl2L12 mRNA expression, while normal tissue did not.

Figure 1:
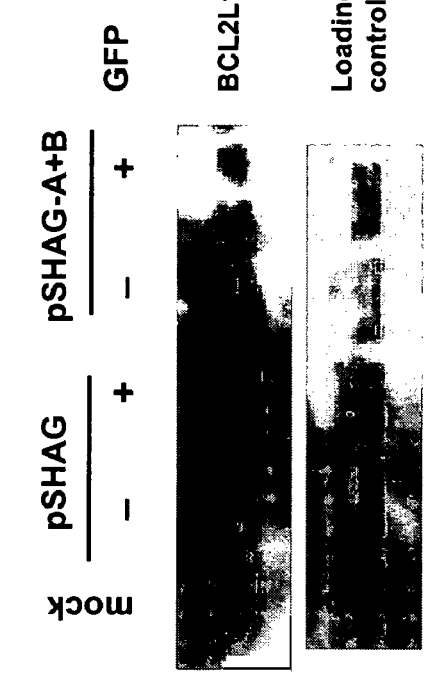
FIG. 1A contains a picture of a Western blot demonstrating reduced expression of Bcl2L12-V5 polypeptide in NIH3T3 cells transfected with pSHAG-Bcl2L12-A or pSHAG-Bcl2L12-B. The numbers indicate the amount of DNA in µg used to transfect the cells.
FIG. 1B contains a picture of a Western blot demonstrating reduced expression of Bcl2L12 polypeptide in U87MG cells enriched for GFP expression and transfected with pSHAG-Bcl2L12-A+-B (pB12-A+B).

NIH3T3 cells were cotransfected with pBabe-Bcl2L12-V5 and either pSHAG-Control, pSHAG-Bcl2L12-A (pSHAG-A), or pSHAG-Bcl2L12-B (pSHAG-B). The pSHAG vectors can be used to induce RNA interference and are similar to those described elsewhere (Paddison et al., *Genes Dev.*, 16:948-958 (2002)). The pSHAG-A construct contained the following Bcl2L12 sequence: 5'-GTTTGTACGAGTTCAG-TGGAGGAGACCGCAA-3' (SEQ ID NO:12), while the pSHAG-B construct contained the following Bcl2L12 sequence: 5'-GTTGAGTGGAGGAGGCGGCG-GTGGGGCC-CCG-3' (SEQ ID NO:13). The pBabe-Bcl2L12-V5 vector expresses a Bcl2L12 polypeptide having the V5 epitope tag that allows the polypeptide to be detected using anti-V5 antibodies. RNA interference induced by the pSHAG-Bcl2L12-A and pSHAG-Bcl2L12-B vectors resulted in the specific down-regulation of the expression of Bcl2L12-V5 polypeptide in the NIH3T3 cells (FIG. 1A). A similar result was observed using Ink4a$^{-/-}$/Arf$^{-/-}$ astrocytes virally infected with nucleic acid encoding Bcl2L12-V5. In addition, Ink4a$^{-/-}$/Arf$^{-/-}$ astrocytes virally infected with nucleic acid encoding Bcl2L1 2-V5 and transfected with pSHAG-Bcl2L12-A+-B (mixture of two vectors: pSHAG-Bcl2L12-A and pSHAG-Bcl2L12-B) exhibited specific down-regulation of the expression of Bcl2L12-V5 polypeptide via Western blot analysis using an anti-V5 monoclonal antibody.

Down-regulation of Bcl2L12 polypeptide expression via RNA interference was assessed in U87MG cells. Briefly, U87MG cells were co-transfected (1:10 ratio) with 0.5 μg of vector encoding GFP and 5 μg of either pSHAG-Control, pSHAG-Bcl2L12-A, pSHAG-Bcl2L12-B, or pSHAG-Bcl2L12-A+-B. Once transfected, the cells expressing GFP were sorted out by FACS analysis. About 3-7 percent of the cells exhibited GFP expression. The FACS-sorted cells were assessed for Bcl2L12 polypeptide expression. An efficient knock-down of endogenous Bcl2L12 polypeptide expression was observed in human U87MG glioma cells transfected with pSHAG-Bcl2L12-A+-B as compared to the levels of Bcl2L12 polypeptide expression observed in U87MG cells transfected with pSHAG (FIG. 1B). The FACS-sorted cells also were seeded in 24-well plates at a density of $1 \times 10^5$ cells, grown in 10% FBS-DMEM, and counted every day for three days. The cells enriched for GFP activity and co-transfected with either pSHAG-Bcl2L12-A, pSHAG-Bcl2L12-B, or pSHAG-Bcl2L12-A+-B exhibited significant inhibition of growth when compared to the growth of cells enriched for GFP activity and cotransfected with the empty pSHAG-Control vector.

To assess apoptosis sensitivity, the FACS-sorted U87MG cells were seeded in 6-well plates at a density of $1 \times 10^6$ cells and grown in 10% FBS-DMEM containing 100 nM staurosporine (STS) for one day. After this one day incubation, the viable cells were determined by a standard trypan blue exclusion assay. U87MG cells transfected with pSHAG-Bcl2L12-A ($p<0.05$), pSHAG-Bcl2L12-B ($p<0.01$), or pSHAG-Bcl2L12-A+-B ($p<0.01$) were significantly (Student t-test) sensitive to staurosporine-induced apoptosis as compared to cells transfected with pSHAG-Control. Cells transfected with pSHAG-Control exhibited about 50-55 percent viability. Cells transfected with pSHAG-Bcl2L12-A, pSHAG-Bcl2L12-B, or pSHAG-Bcl2L12-A+-B exhibited about 34-36, 20-25, or 28-30 percent viability, respectively.

In addition, Ink4a/Arf deficient embryonic fibroblasts were transfected with vector only or a vector encoding a Bcl2L12 polypeptide or Bcl2 polypeptide. Once the cells were transfected, the number of colonies formed in cultures (about 300 cells per 6 well plate) was determined. Expression of Bcl2L12 polypeptide promoted growth of Ink4a/Arf deficient embryonic fibroblasts. Cells expressing Bcl2L12 polypeptide resulted in about 26 colonies, while cells expressing Bcl2 resulted in about 10 colonies, and cells containing the vector only resulted in about 13 colonies. In a similar experiment, Ink4a/Arf deficient embryonic fibroblasts were co-transfected with a vector encoding H-RasV12 and either a vector only, vector encoding Bcl2L12 polypeptide, or a vector encoding Bcl2 polypeptide. Once the cells were transfected, the number of foci formed per transfection was determined. Expression of Bcl2L12 polypeptide or Bcl2 polypeptide in combination with H-RasV12 expression promoted growth of Ink4a/Arf deficient embryonic fibroblasts (about 1.5 to 2 fold more foci per transfection for cells expressing Bcl2L12 polypeptide or Bcl2 polypeptide compared to control pBabe cells).

These efforts led to the identification a new GBM oncogene, Bcl2L12. Bcl2L12 exhibits frequent copy number gain (e.g., up to 55%) and up-regulated expression (e.g., up to 90%) in GBM, but not in low-grade disease. The Bcl2L12 polypeptide also contributes to the intense proliferative and survival potential when over-expressed in primary non-transformed astrocytes (mouse) and human GBM cells. In addition, RNAi vectors' stably expressing two different Bcl2L12-specific RNAi molecules were constructed that, upon introduction into cells, resulted in an efficient knock-down of Bcl2L12 polypeptide expression. This knock-down in Bcl2L12 polypeptide expression resulted in diminished viability of U87MG cells upon exposure to staurosporin, indicating that Bcl2L12 participates in the growth and survival of established glioma cells.

Example 3

Figure 2:
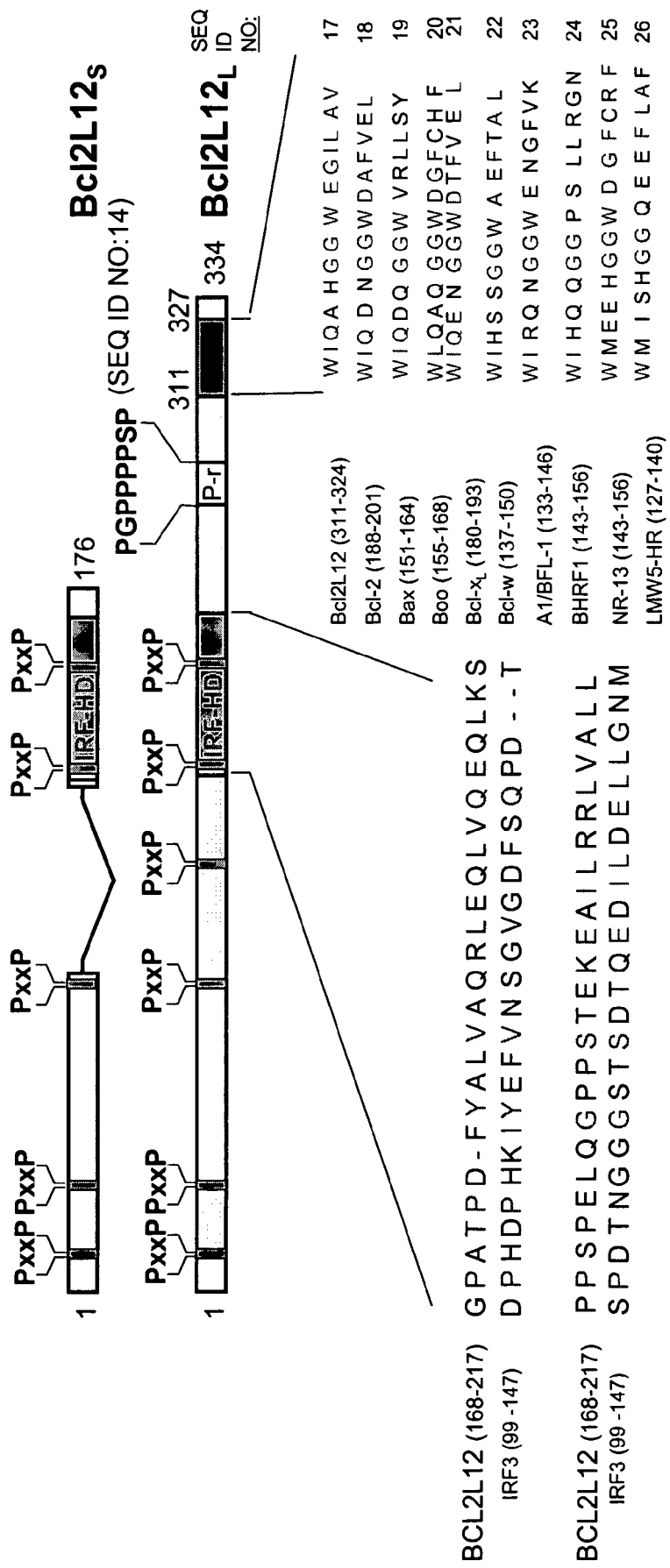
FIG. 2 is a diagram of the domain structure of Bcl2L12 polypeptides.

Bcl2L12 Polypeptides are Anti-apoptotic Oncogene Products Over-Expressed in High Grade Astrocytomas The domain structure of Bcl2L12 polypeptide is as depicted in FIG. 2. Briefly, Bcl2L12 polypeptide is a Bcl-2 like proline-rich polypeptide. The open reading frame is predicted to be 1005 bp, encoding a deduced 334 amino acid polypeptide with a molecular mass of 36.8 kD. The Bcl2L12 polypeptide contains a C-terminal 14 amino acid sequence region with significant homology to those sequences found in the BH2 domain of several members of the Bcl2 protein family. Motifs homologous to BH1, BH3, or BH4 domains do not appear in the Bcl2L12 polypeptide sequence. In addition, Bcl2L12 contains a stretch of 50 amino acids in the center of the molecule with significant homology to IRF3 and proline-rich modules that are characterized by the presence of the consensus PXXP tetrapeptide found in proline-rich proteins. Six PXXP motifs and one PPPP motif identical to the proline-rich motifs identified in the oncogene products of the RRAS and TC21 oncogenes are present in the Bcl2L12 polypeptide.

The human and mouse Bcl2L12 polypeptides have similar amino acid sequences (FIG. 3). In fact, the similarity index at the amino acid level for the human and mouse sequences is 82.4 percent, while the similarity index at the nucleic acid level for the human and mouse sequences is 75.8 percent.

Semi-quantitative RT-PCR was used to measure the levels of Bcl2L12 mRNA in GBM cell lines, primary GBM cell lines, and low grade astrocytomas. High levels of Bcl2L12 mRNA were detected in GBM cell lines (A1207, 4.5 fold increase; LN229, 4.5 fold increase; U178, 8 fold increase; LNZ308, 14 fold increase; and U87, 14 fold increase) and primary GBM cell lines (Gli14, 1 fold; Gli13, 3 fold increase; Gli36, 12 fold increase; and Gli5, 11 fold increase), but not the tested low grade astrocytomas (xT96, 2 fold increase; xT2859, 1 fold; and xT3247, 1 fold).

To test whether the Bcl2L12 polypeptide exhibits anti- or pro-apoptotic activity, Ink4a/Arf deficient astrocytes ectopically expressing Bcl2L12-V5 polypeptide or containing an empty vector as control were treated with 500 nM STS. After STS treatment, the cells were analyzed for apoptosis by assessing annexin V binding and DNA fragmentation using a FACS based analysis. Expression of Bcl2L12-V5 polypeptides significantly blocked apoptosis induced by STS. For annexin V binding, cells transfected with pBabe resulted in about 20 percent annexin $V^+/PI^-$ cells, while cells expressing Bcl2L12 polypeptide resulted in about 6 percent annexin $V^+/PI^-$ cells. For DNA fragmentation, cells transfected with pBabe resulted in about 22 percent DNA fragmentation, while cells expressing Bcl2L12 polypeptide resulted in about 2 percent DNA fragmentation. These results indicate that Bcl2L12 may target the mitochondrial branch of the apoptosis signaling pathway at a mitochondrial level or at a post-mitochondrial level.

Elevated $BCl-x_L$ polypeptide levels can confer resistance towards cis-platin induced apoptosis in EGFR* transduced glioma cell lines. The protective effect of the Bcl2L12-V5 polypeptide, however, is independent of Bcl-$x_L$ since BCl-$x_L$ polypeptide expression levels were similar in the Bcl2L12-V5 and vector only transfectants.

The anti-apoptotic activity of the Bcl2L12 polypeptide was independent of the C-terminal BH2 domain, since Ink4a/Arf deficient astrocytes overexpressing a Bcl2L12-V5 mutant lacking this BH2 domain still protected against STS-mediated apoptosis. Cells expressing a Bcl2L12-V5-ΔBH2 polypeptide resulted in about 7 percent DNA fragmentation. The Bcl2L12-V5-ΔBH2 polypeptide lacks amino acid residues 311-334 present in the human Bcl2L12 polypeptide. Expression of the Bcl2L12-V5 polypeptide in Ink4a/Arf deficient astrocytes also conferred complete resistance to anti-Fas, TRAIL, etoposide, and carboplatin mediated apoptosis.

The ability of Bcl2L12 polypeptide to promote colony formation was assessed. Briefly, 1000 cells were seeded in a 10 cm dish and γ-irradiated (5 Gy). After culturing the irradiated cells for ten days, the cells were stained with crystal violet, and the number of colonies was counted. Bcl2L12-V5 polypeptide expression promoted colony formation in Ink4a/Arf deficient astrocytes upon γ-irradiation (about 27 colonies for cells expressing Bcl2L12-V5 polypeptides compared to about 17 colonies for control vector only cells; 1000 cells/10 cm dish).

Figure 5:
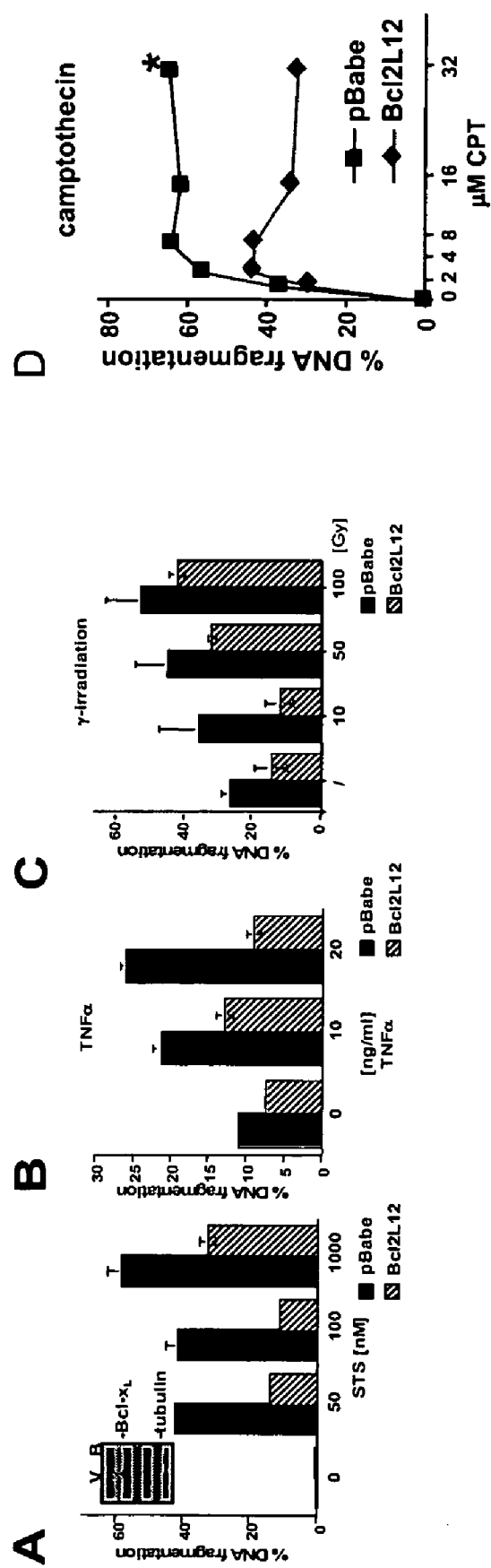
FIG. 5A is a bar graph plotting the percent DNA fragmentation exhibited in INK4a/Arf deficient astrocytes transfected with vector only (pBabe) or a vector driving Bcl2L12-V5 polypeptide expression (Bcl2L12), and treated with the indicated amounts of STS. The inset gel photograph depicts the amount of Bcl-xL polypeptide and tubulin expressed in the cells transfected with the vector only (V) or the vector driving Bcl2L12-V5 polypeptide expression (B).
FIG. 5B is a bar graph plotting the percent DNA fragmentation exhibited in INK4a/Arf deficient astrocytes transfected with vector only (pBabe) or a vector driving Bcl2L12-V5 polypeptide expression (Bcl2L12), and treated with the indicated amounts of TNFα plus 1 µg/mL cycloheximide.
FIG. 5C is a bar graph plotting the percent DNA fragmentation exhibited in INK4a/Arf deficient astrocytes transfected with vector only (pBabe) or a vector driving Bcl2L12-V5 polypeptide expression (Bcl2L12), and treated with the indicated amounts of γ-irradiation.
FIG. 5D is a graph plotting the percent DNA fragmentation exhibited in INK4a/Arf deficient astrocytes transduced with vector only (pBabe) or a vector driving Bcl2L12-V5 polypeptide expression (Bcl2L12), and treated with the indicated amounts of camptothecin.

In a separate experiment, Ink4a/Arf deficient astrocytes ectopically expressing Bcl2L12-V5 polypeptide or containing an empty vector as control were treated with 0, 50, 100, or 1000 nM of STS. After a 24 hour-incubation, DNA fragmentation was measured using FACS-based quantification of sub-G1 DNA content. Ectopic expression of a Bcl2L12 polypeptide protected astrocytes from STS-induced apoptosis at low, medium, and high drug doses (FIG. 5A).

In another experiment, Ink4a/Arf deficient astrocytes ectopically expressing Bcl2L12-V5 polypeptide or containing an empty vector as control were treated with 0, 2, 4, 8, 16, or 32 μM camptothecin (CPT) for 20 hours. After the 20 hour incubation, DNA fragmentation was determined by FACS-based quantification of sub-G1 peaks. Expression of the Bcl2L12 polypeptide conferred resistance to CPT-stimulated apoptosis. The percent DNA fragmentation after treatment with 32 μM CPT was significantly ($p=0.012$) lower in cells expressing the Bcl2L12 polypeptide than in control cells containing the empty pBabe vector (FIG. 5D). The maximum percent DNA fragmentation observed in CPT-treated cells expressing the Bcl2L12 polypeptide was about 35 to 45 percent, whereas CPT-treated cells containing pBabe had a maximum percent DNA fragmentation of greater than 60 percent (FIG. 5D).

Ink4a/Arf deficient astrocytes ectopically expressing Bcl2L12-V5 polypeptide or containing an empty vector as control were treated with TNFα in the presence of 1 μg/mL cycloheximide for 24 hours. After the 24 hour incubation, DNA fragmentation was measured using FACS-based quantification of sub-G1 DNA content. The Bcl2L12 polypeptide expression conferred significant protection of INK4a/ARF deficient astrocytes from TNFα-mediated apoptosis (FIG. 5B).

Ink4a/Arf deficient astrocytes ectopically expressing Bcl2L12-V5 polypeptide or containing an empty vector as control were treated with 0, 10, 50, and 100 Gray (Gy) of γ radiation. After 24 hours, DNA fragmentation was measured. Ectopic expression of a Bcl2L12 polypeptide protects INK4a/Arf deficient astrocytes from γ-irradiation-induced apoptosis (FIG. 5C).

Example 4

Bcl2L12 Polypeptides are Located in the Cytoplasm and the Nucleus

Anti-apoptotic members of the Bcl-2 family are integral membrane proteins found in the mitochondria, endoplasmatic reticulum (ER), or nuclear membranes. In contrast, pro-apoptotic members localize to cytosol or cytoskeleton prior to a death signal. Upon apoptosis induction, the pro-apoptotic members have been shown to undergo a conformational change enabling them to translocate and integrate into intracellular membranes, most notably the mitochondrial outer membrane. One model explaining the anti-apoptotic activity of certain Bcl-2 family members holds that they "guard the mitochondrial gate" from pro-apoptotic Bcl-2 like proteins that "gain access" following a death signal.

The subcellular localization of ectopically expressed Bcl2L12 in Ink4a/Arf deficient astrocytes and in U87MG cells was determined. Ink4a/Arf deficient astrocytes stably expressing V5 tagged Bcl2L12 polypeptides and U87MG cells transiently expressing V5 tagged Bcl2L12 polypeptides were subjected to immunofluorescence microscopy using an anti-V5 monoclonal antibody and a FITC labeled secondary anti-mouse antibody. The cells also were stained with DAPI to visualize the nuclei. In addition, the DAPI stainings were overlaid with the FITC stainings. Specificity of the anti-V5 immunostaining was established using a control anti-IgG2a antibody that only showed background staining. The Bcl2L12-V5 polypeptide exhibited cytoplasmic and nucleoplasmic localization, but no mitochondrial localization, when expressed in Ink4a/Arf deficient astrocytes and in U87MG cells.

To further confirm the localization pattern of Bcl2L12 polypeptides, a GFP-Bcl2L12 fusion polypeptide was generated. The vector encoding this fusion polypeptide was transiently transfected into Ink4a/Arf deficient astrocytes, and the transfected cells were examined as above. The GFP-Bcl2L12 fusion polypeptide exhibited the same distribution pattern as that exhibited with the V5-tagged Bcl2L12 polypeptide.

In addition, nuclear, cytosolic, and heavy membrane fractions from Ink4a/Arf deficient astrocytes overexpressing Bcl2L12-V5 polypeptides or a mutant Bcl2L12-V5 polypeptide lacking the BH2 domain (Bcl2L12-V5-ΔBH2) were prepared using differential centrifugation. These fraction were then assessed for Bcl2L12 immunoreactivity using anti-Bcl2L12 antibodies. The wild type Bcl2L12-V5 polypeptides as well as the Bcl2L12-V5-ΔBH2 mutant polypeptides were detected in the nuclear and cytoplasmic fractions, but not in the heavy membrane fraction. These results are consistent with the immunofluorescence data provided above. Translocation of Bcl2L12 polypeptides during apoptosis was not detected when assessed by immuno-fluorescence and subcellular fractionation using Ink4a/Arf deficient astrocytes stably over-expressing Bcl2L12-V5 polypeptides.

The nuclear and cytoplasmic localization of ectopically expressed Bcl2L12-V5 in human embryonic kidney cells (293T cells) was assessed using subcellular fractionation. Lamin B1 was used as a marker for nuclear localization, while caspase-9 and Apaf-1 were used as markers for cytoplasmic localization. A Triton X-100 lysate of 293T cells transfected with either vector only or the vector encoding a Bcl2L12-V5 polypeptide were used as a specificity control for the anti-V5 immunoblot. As shown for primary astrocytes and U87MG cells, Bcl2L12-V5 polypeptides exhibited a nuclear and cytoplasmic distribution in 293T cells, suggesting that Bcl2L12-V5 polypeptides over-expressed in 293T cells are localized in a manner similar to that observed in glial cells.

These results demonstrate that Bcl2L12 polypeptides do not localize to intracellular organelles like the mitochondria, ER, or nuclear envelope. This is in contrast to other anti-apoptotic members of the Bcl2 family.

Figure 6:
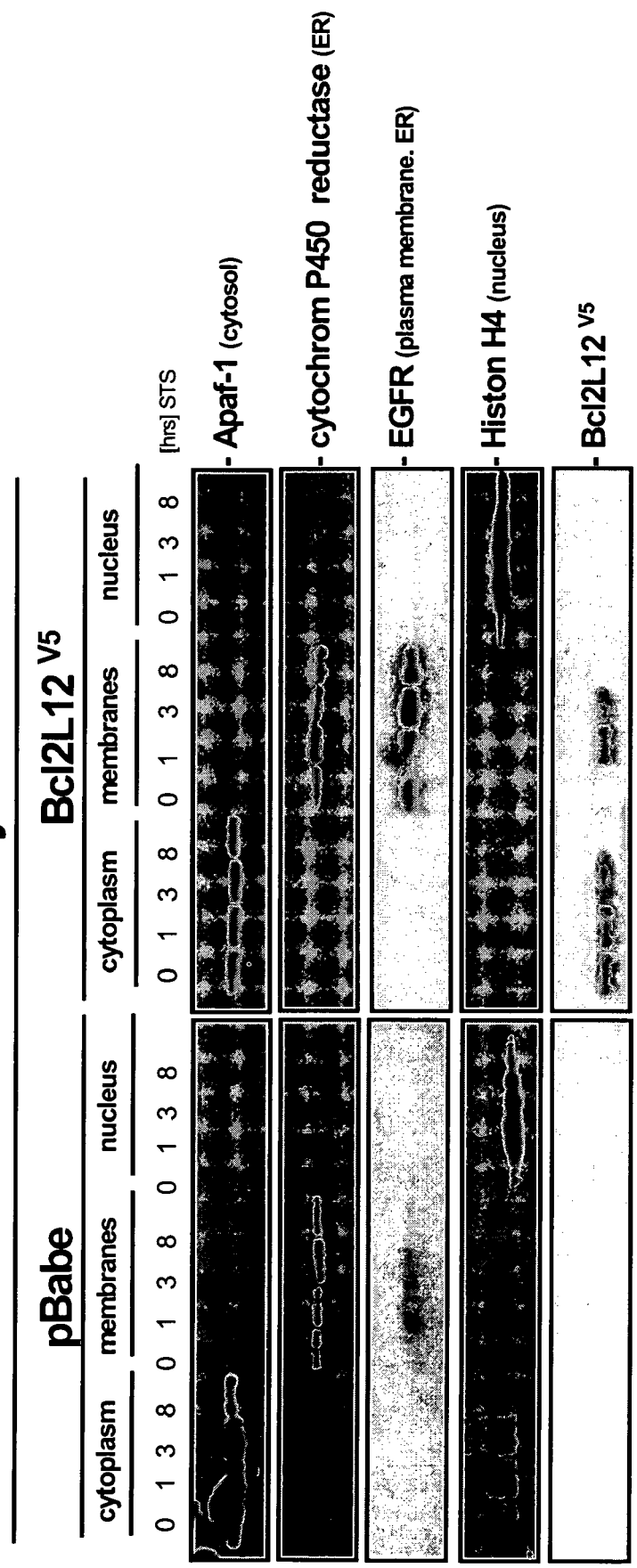
FIG. 6 contains photographs of Western blots of subcellular fractions from astrocytes transfected with pBabe or a vector designed to express a Bcl2L12-V5 polypeptide.

In a separate experiment, subcellular fractions were separated based on differential protein solubilization rather than differential centrifugation to allow for a more efficient separation of subcellular contents. Briefly, the astrocyte cultures were subjected to subcellular fractionation after treatment with STS for 0, 1, 3, or 8 hours using the ProteoExtract Kit (Calbiochem) according to the manufacturer's instructions. Bcl2L12 polypeptide was detected in the membrane fractions for cells treated with STS for 1 and 3 hours (FIG. 6). These results indicate that Bcl2L12 polypeptides reside in the cytoplasm and translocate to the membrane fraction upon apoptosis induction in INK4a/Arf deficient astrocytes.

Example 5

Bcl2L12 Polypeptides Block Apaf-1 Mediated Caspase-9 Activation

Direct mitochondrial control of the apoptotic process has been demonstrated. In general, soon after the induction of apoptosis, a loss of mitochondrial transmembrane potential ($\Delta\Psi_M$) occurs concurrent with the formation of permeability transition (PT) pores. At the same time, cytochrome c is inactivated and subsequently released into the cytoplasm.

To determine whether Bcl2L12 polypeptides inhibit the apoptogenic activity of mitochondria, cytochrome c release in STS-treated astrocytes over-expressing Bcl2L12-V5 polypeptides was assessed and compared to astrocytes transfected with a LacZ control vector. An anti-tubulin immunoblot was performed as a loading control. Suboptimal concentrations of digitonin were used to allow for selective permeabilization of the plasma membrane, but not of the intracellular membranes. Bcl2L12-V5 did not block cytochrome c release. This result indicates that, unlike other Bcl-2 family members, Bcl2L12 polypeptides exert their anti-apoptotic activity downstream of mitochondria. This is consistent with the inability of Bcl2L12-V5 polypeptides to localize to mitochondria. Ink4a/Arf deficient astrocytes over-expressing Bcl2L12-V5-ΔBH2 polypeptides also exhibited cytochrome c release.

Like the receptor-adapter-procaspase complex at the plasma membrane, the so-called apoptosome can be regarded as a signaling complex that promotes caspase activation downstream of the mitochondria. This high-molecular weight complex consists of Apaf-1, caspase-9, deoxyadenosine triphosphate (dATP), and cytochrome c. Apaf-1 binds caspase-9 and promotes its processing. Cytochrome c and dATP are cofactors that may be involved in the conformational changes of Apaf-1 that initiate caspase-9 activation.

The following experiment was performed to determine whether Bcl2L12 inhibits caspase activation. Briefly, a caspase activation profile was generated using fluorochrome-labeled peptides resembling the ideal cleavage sites for caspases-2 (VDVAF; SEQ ID NO:29), caspases-3/7 (DEVD; SEQ ID NO:27), caspase-6 (VEID; SEQ ID NO:31), caspase-8 (IETD; SEQ ID NO:30), and caspase-9 (LEHD; SEQ ID NO:28). Two confluent 15 cm dishes of astrocytes (pBabe or Bcl2L12-V5 transfected) were left untreated or treated with STS (500 nm) for 24 hours and lysed in a lysis buffer containing 1% Triton X-100. The lysed cells were then spun for 15 minutes at 14,000 rpm at 4° C. to obtain a post-nuclear supernatant. The supernatants (standardized to 20 mg of protein) were incubated with 40 µM of AFC labeled peptide substrate for 1 hour at 37° C. The samples were read in a fluorescence plate reader, and the specific RFUs were calculated. In the presence of active caspases, the fluorogenic group AFC is released from the peptide, and its fluorescence can be quantified using a plate reader.

Each tested caspase activity (caspase-2; caspase-3/7; caspase-6; caspase-8; and caspase-9) was significantly impaired in astrocytes transfected with a vector encoding a Bcl2L12-V5 polypeptide. In addition, an even more pronounced inhibition of each tested caspase activity (caspase-2; caspase-3/7; caspase-6; caspase-8; and caspase-9) was observed in astrocytes ectopically expressing the Bcl2L12-V5-ΔBH2 mutant polypeptide. These results indicate that Bcl2L12 exerts its anti-apoptotic function at the level of caspase activation downstream of mitochondria and independently of the BH2 domain. Since each tested caspase activity was significantly blocked, Bcl2L12 polypeptides function by inhibiting the most upstream caspase within the mitochondrial branch of the apoptosis signaling pathway, caspase-9. To confirm this, caspase-9 activation was assessed using in vitro and in vivo apoptosome assays, and the association of Apaf-1 with Bcl2L12 was assessed.

To determine if Bcl2L12 polypeptides could-regulate-the activity of caspase-9, a cell-free system was used in which exogenously added dATP and cytochrome c induced the activation of [$^{35}$S] labeled in vitro translated caspase-9. Processing of caspase-9 into p37 and p35 has been shown to be strictly dependent on Apaf-1, dATP, and cytochrome c. Recombinant GST-Bcl2L12 polypeptides inhibited the maturation of caspase-9 significantly when compared to a cytosolic extract of 293T cells incubated with GST. To confirm the inhibitory effect of Bcl2L12 polypeptides on caspase-9 maturation, 293T cells ectopically expressing Bcl2L12-V5 polypeptides where either subjected to an in vitro cleavage assay or to an activity assay using the caspase-9 specific fluorogenic peptide LEHD. Using the in vitro cleavage assay, 293T cells transfected with a vector encoding a Bcl2L12-V5 polypeptide exhibited reduced processing of caspase-9 into the p37 and p35 cleavage intermediates when compared to the processing observed in cells transfected with vector only. In the activity assay, LEHDase activity was significantly reduced in 293T cells expressing a Bcl2L12-V5 polypeptide (about 260 RFUs; relative fluorescence units) when compared to the LEHDase activity observed in 293T cells transfected with control vector (about 800 RFUs).

Figure 4:
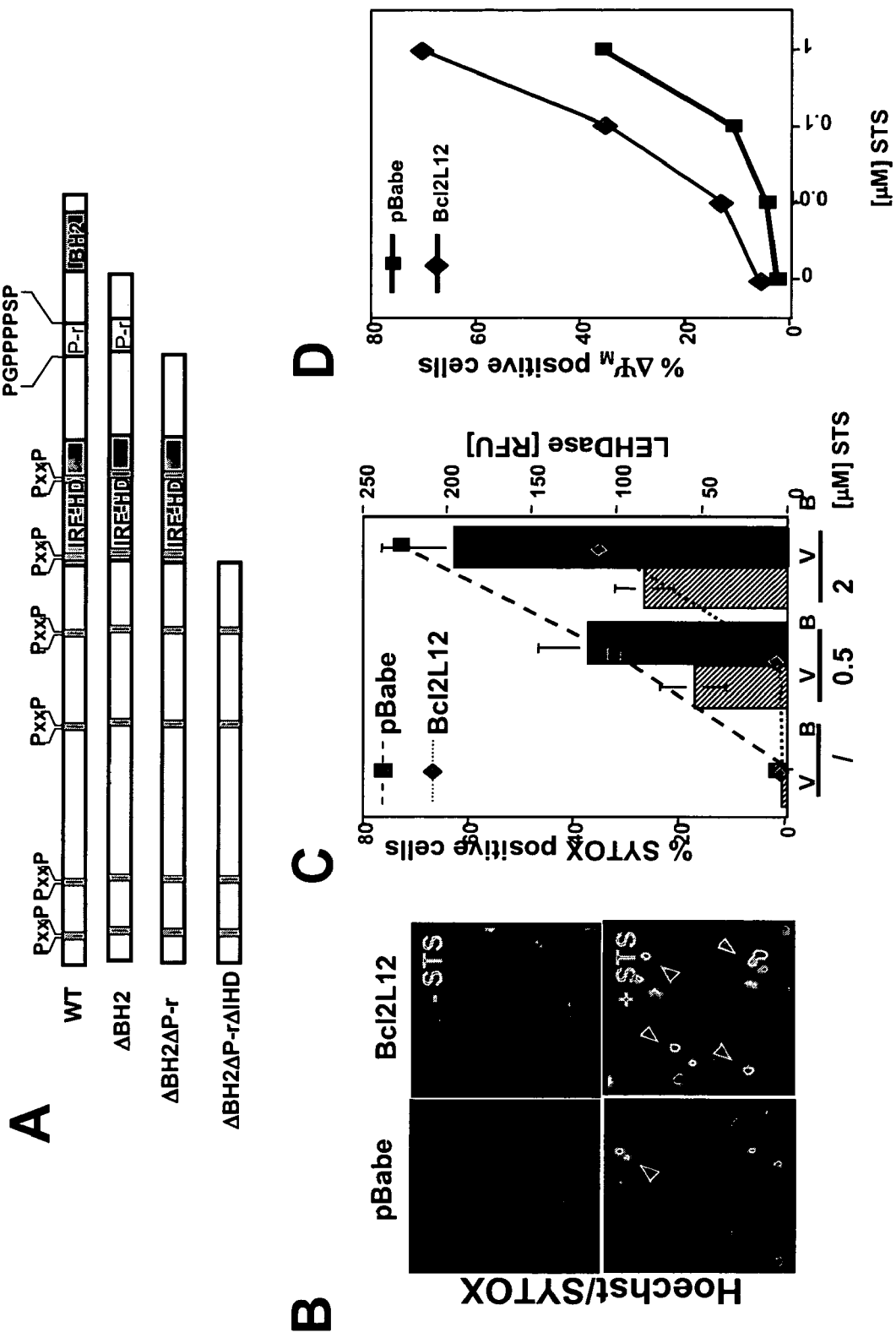
FIG. 4A is a schematic of a wild-type human Bcl2L12 polypeptide (WT; human amino acid sequence 1-334), a human Bcl2L12-ΔBH2 polypeptide (ΔBH2; human amino acid sequence 1-310), a human Bcl2L12-ΔBH2ΔP-r polypeptide (ΔBH2ΔP-r; human amino acid sequence 1-267), and a human Bcl2L12-ΔBH2ΔP-rΔIHD polypeptide (ΔBH2ΔP-rΔIHD; human amino acid sequence 1-167).
FIG. 4B is a photograph of the indicated astrocytes stained with Hoechst and SYTOX.
FIG. 4C is a graph plotting the percent SYTOX positive cells as well as the amount of LEHDase activity in the indicated samples. The V represents samples from cells transfected with vector only, while the B represents samples from cells transfected with a vector encoding a Bcl2L12-V5 polypeptide.
FIG. 4D is a line graph plotting the percent $\Delta\Psi_M$ positive cells for the indicated STS treatment using cells transfected with vector only (pBabe) or with a vector encoding a Bcl2L12-V5 polypeptide.

In addition, vectors encoding V5 tagged wild-type human Bcl2L12 polypeptide (WT; human amino acid sequence 1-334) and three V5 tagged truncation mutants of human Bcl2L12 (Bcl2L12-ΔBH2 polypeptide, human amino acid sequence 1-310; Bcl2L12-ΔBH2ΔP-r polypeptide, human amino acid sequence 1-267; and Bcl2L12-ΔBH2ΔP-rΔIHD polypeptide, human amino acid sequence 1-167) were made (FIG. 4A). These vectors expressed the appropriately sized polypeptides when translated in vitro or when expressed in 293T cells. In addition, each truncation mutant exhibited the ability to inhibit caspase-9 activity to a level similar to that observed with the full-length Bcl2L12 polypeptide (cells with vector only, about 420 RFUs; cells with WT, about 145 RFUs; cells with Bcl2L12-ΔBH2, about 160 RFUs; cells with Bcl2L12-ΔBH2ΔP-r, about 130 RFUs; and cells with Bcl2L12-ΔBH2ΔP-rΔIHD, about 160 RFUs).

In another experiment, Ink4a/Arf deficient astrocytic cell cultures ectopically expressing the Bcl2L12-V5 polypeptide or containing pBabe were treated with STS (1 µM) for 0, 2, 4, 8, or 16 hours. Cell lysates were analyzed by Western blotting using anti-caspase-9 antibodies (1:1000; Cell Signaling), anti-caspase-7 antibodies (0.5 µg/ml; BD Pharmingen), anti-caspase-3 antibodies (0.25 µg/ml; BD Transduction Laboratories), anti-cleaved caspase-9 antibodies (1:1000; Cell Signaling), anti-cleaved capase-7 antibodies (1:1000; Calbiochem), and anti-cleaved caspase-3 antibodies (1:1000; Calbiochem). This analysis of procaspase maturation during STS-mediated apoptosis in the setting of ectopic Bcl2L12 polypeptide expression revealed significant reduction of the maturation of effector caspases 3 and 7, but not of caspase-9 autoprocessing (FIG. 8A).

To place the above profile of Bcl2L12 polypeptide activity in the context of a classical pro-survival glioma oncogene, the impact of Bcl2L12 polypeptide was compared with that of activated epidermal growth factor receptor (EGFR*) on cytochrome c release and processing along the caspase cascade. Using antibodies specific for the active caspase species, Western blot analyses revealed profound Bcl2L12-mediated inhibition of caspases 3 and 7 processing similar to that of EGFR* over-expression (FIG. 8B). These results corresponded well to the observed reduction of DNA fragmentation in STS-stimulated (1 µM) Ink4a/Arf deficient astrocytic cell cultures expressing Bcl2L12 or EGFR* polypeptides compared to that in STS-stimulated control cultures containing pBabe (FIG. 9A).

Figure 8:
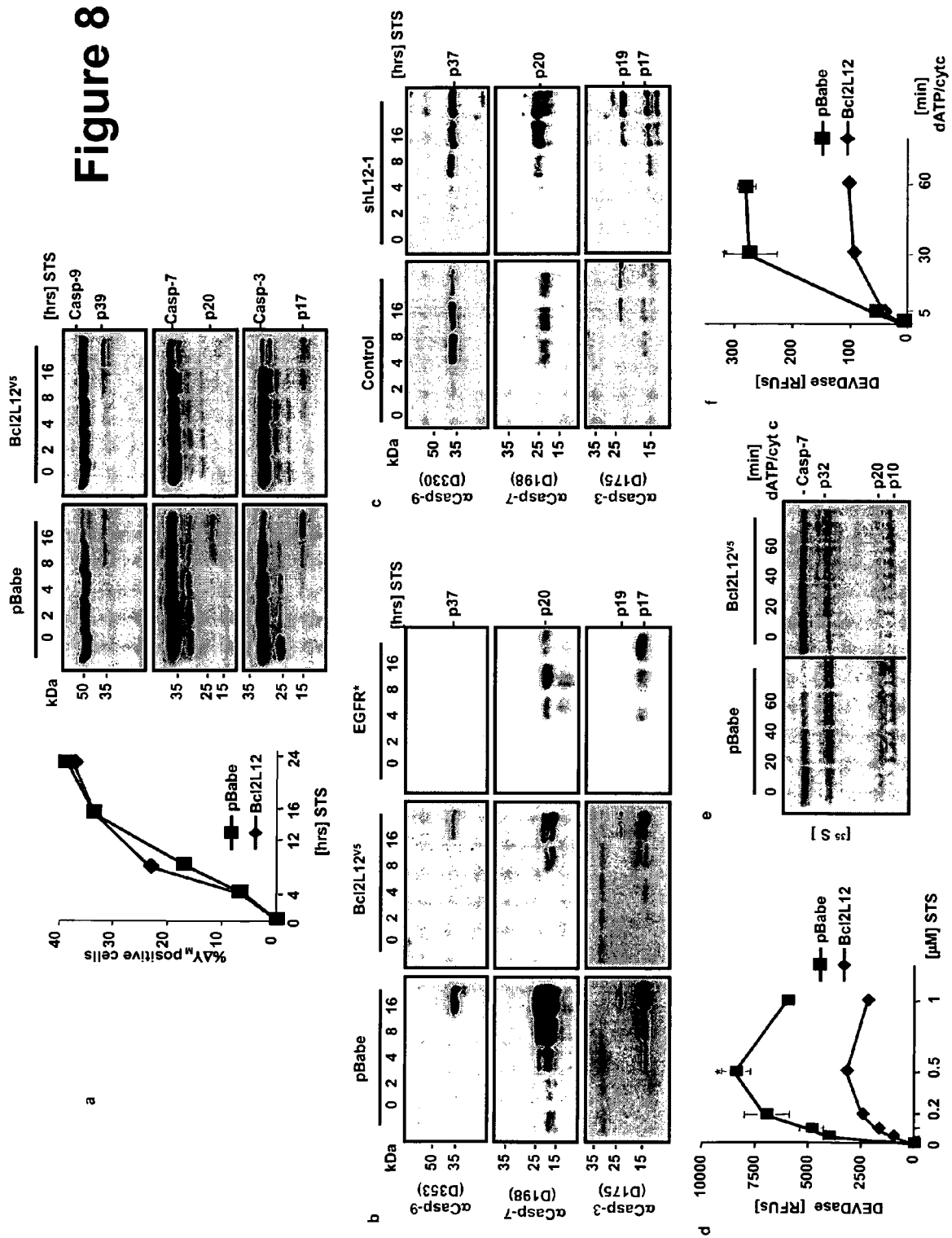

The mechanism of action of EGFR*, in contrast to Bcl2L12, stems from the activation of upstream survival pathways that converge to inhibit cytochrome c redistribution and subsequent caspase-9 processing (FIG. 8B), as reported previously (Nagane et al., *Proc Natl Acad Sci USA* 95:5724-9(1998)). In addition, the ability of Bcl2L12 polypeptide to inhibit effector caspase function is reflected in decreased levels of the caspase-9 p37 as a result of caspase-3-mediated cleavage intermediate (FIG. 8A, 16 hours; Fujita et al., *Cell Death Differ.* 8:335-44 (2001)). Conversely, RNAi-mediated knockdown of endogenous Bcl2L12 polypeptide expression in U87MG cells resulted in enhanced activation of caspases 3 and 7, but did not affect early caspase-9 maturation (FIG. 8C, 0 to 8 hours). As a consequence of a caspase-3-mediated feedback mechanism (Fujita et al., *Cell Death Differ.* 8:335-44 (2001); Slee et al., *J Cell Biol.* 144, 281-92 (1999)), caspase-9 processing in later phases of apoptosis progression was enhanced (FIG. 8C, 16 hours). The lack of an impact on early stage apoptosis signaling events (i.e., mitochondrial membrane desintegration, caspase-9 activation, and normal apoptosome assembly and activity) coupled with inhibition of effector caspase maturation translated into significant blockage of caspase-3-like (DEVDase) activity by Bcl2L12 polypeptide (FIG. 8D) comparable to inhibition of caspase-3-like caspases by EGFR* (FIG. 9B). To determine whether Bcl2L12 polypeptides block caspase-3-like activity, Ink4a/Arf deficient astrocytic cell cultures ectopically expressing Bcl2L12-V5 or containing pBabe were treated with 0, 0.2, 0.5, or 1 µM STS and lysed with lysis buffer C (150 mM NaCl; 30 mM Tris-HCl, pH 7.5; 10% glycerol (v/v); 1% triton X-100 (v/v); and protease inhibitor cocktail (Roche)). The cell lysates were incubated with 40 µM amino trifluoromethyl coumarin (AFC)-labeled caspase-specific peptides zDEVD-AFC for caspases 3 and 7 and Ac-LEHD-AFC for caspase 9 (Bachem) in assay buffer for 0.5-1 hour at 37° C. Caspase activities were determined fluorometrically using a fluorescence plate reader. Values obtained with unstimulated cells were taken as background and subtracted from those obtained with stimulated cells. Following stimulation with 0.5 µM STS, lysates from cells containing pBabe produced a fluorescent signal of about 8500 RFUs in the DEVDase activity assay, whereas the signal obtained with lysates from cells expressing Bcl2L12 polypeptide was about 3500 (p=0.038).

The caspase activation profiles in murine astrocytes and human glioma cells were further confirmed in a cell-free in vitro system, in which dATP (1 mM)/cyt c (5 µM) stimulated cell extracts derived from Bcl2L12-overexpressing astrocytes exhibited blockage of caspase-7 maturation (FIG. 8E) and DEVDase activity (FIG. 8F) compared to pBabe control cells.

To test whether Bcl2L12 polypeptides bind Apaf-1 polypeptides, [$^{35}$S] labeled in vitro translated Apaf-1 was incubated with GST-Bcl2L12 polypeptides, and binding was assessed. Briefly, *E. coli* were transfected with an expression vector encoding the GST-Bcl2L12 polypeptide. After culturing, the *E. coli* were harvested and sonicated. The disrupted cells were spun, and the resulting supernatant was incubated with glutathione-coated beads for one hour at room temperature. After washing the beads with PBS, they were incubated with the labeled Apaf-1 polypeptides at 4° C. for 24 hours. The beads were washed three times and treated with sample buffer containing SDS, which was then analyzed by SDS-PAGE. BCl-$x_L$ and Bcl-2 GST fusion proteins were used as controls. In contrast to Bcl-$x_L$ and Bcl-2 GST fusion proteins, GST-Bcl2L12 polypeptides bound the labeled Apaf-1 polypeptides significantly.

To confirm this interaction, 293T cells were used to test the physical interaction between Apaf-1 and Bcl2L12 polypeptides in vivo. When ectopically expressed in 293T cells, Bcl2L12-V5 polypeptides exhibited the same intracellular distribution pattern observed to glial cells, indicating that the higher expression levels of Bcl2L12 in 293T cells do not interfere with its localization and that 293T cells behave similarly to cells of glial origin. To test the association between Apaf-1 and Bcl2L12 polypeptides in vivo, Bcl2L12-V5 polypeptides were expressed in 293T cells and immunoprecipitated with an anti-V5 antibody. The amount of co-immunoprecipitated endogenous Apaf-1 polypeptide then was determined by Western blot analysis. Apaf-1 polypeptides were found to be associated with Bcl2L12-V5 polypeptides, but absent in an immunoprecipate using a control mAb IgG2a demonstrating the specificity of the pulldown assay.

To assess whether the BH2 domain is necessary for Apaf-1 binding, Bcl2L12-V5-ΔBH2 polypeptides were immunoprecipitated from 293T cells, and co-immunoprecipitated Apaf-1 was quantified as described. Despite the reduced expression levels when compared to the wild-type Bcl2L12 polypeptide levels, the Bcl2L12-V5-ΔBH2 mutant polypeptide bound comparable levels of Apaf-1 polypeptide. This result indicates that the BH2 domain is dispensable for Apaf-1 binding.

In a separate set of experiments, caspase-9 polypeptide tagged with a FLAG tag exhibited binding to Apaf-1 polypeptides. The binding of caspase-9 to Apaf-1 occurred in the presence and absence of Bcl2L12-V5 polypeptides.

Example 6

Bcl2L12 Polypeptides Promote Necrogenesis

Necrogenesis is not simply due to reduced blood and consequently oxygen supply, but rather reflects the molecular consequence of dysregulated signaling pathways. Bcl2L12 polypeptides may enhance necrosis, since they block the activation of the most upstream caspase, caspase-9, through modulation of Apaf-1 function thereby disabling the activation of a post-mitochondrial caspase cascade. To test whether Bcl2L12 polypeptides have a pro-necrotic activity, necrosis was determined by measuring nuclear swelling, plasma membrane integrity, and dissipation of the mitochondrial membrane potential $\Delta\Psi_M$.

To quantify nuclear swelling in Ink4a/Arf deficient astrocytic cell cultures, cells transfected with vector only or a vector encoding a Bcl2L12-V5 polypeptide were treated with or without STS (500 nM) for 24 hours, lysed, and stained with Propidium Iodide (Nicoletti method). Nuclei with increased forward scatter (i.e., increased size) were defined as swollen, and the number of those nuclei relatively to the total number of nuclei was expressed as the percent swelling. Astrocytes expressing the Bcl2L12-V5 polypeptide exhibited an increase in the percent swelling when compared to the percent swelling results from cells transfected with vector only. Cells expressing the Bcl2L12-V5 polypeptide and treated with STS exhibited about 67 percent swelling, while cells transfected with vector only and treated with STS exhibited about 42 percent swelling.

To assess and quantify plasma membrane integrity, vector or Bcl2L12-V5 transfected astrocytes were treated with or without STS (500 nM) for 24 hours and stained with a combination of Hoechst (a DNA intercalating dye that enters living as well as apoptotic or necrotic cells) and SYTOX Green (a green fluorescent dye that only enters cells with a disintegrated plasma membrane). FIG. 4B is a picture of STS treated and untreated cells transfected with either a control vector (pBabe) of a vector encoding a Bcl2L12-V5 polypeptide.

In addition, the green cells were counted over a range of different STS concentration (FIG. 4C; bars), and caspase-9 activity was determined by quantifying LEHDase activity in the corresponding cell lysates (FIG. 4C; histogram). Whereas SYTOX Green positivity was significantly increased in the Bcl2L12-V5 transfectant, caspase-9 activity was dramatically reduced (FIG. 4C). SYTOX green positive cells were also quantified using a FACS based analysis assessing the increase in green fluorescence. The results from that analysis were similar to the results provided in FIG. 4C.

Like nuclear swelling and plasma membrane integration, a loss of the mitochondrial membrane potential is a hallmark of necrosis. To determine the dissipation of $\Delta\Psi_M$, STS treated astrocytes transfected with either vector only (pBabe) or a vector encoding a Bcl2L12-V5 polypeptide were stained with JC-1, and cells with an increase in fluorescence (FL-1) were quantified using FACS analysis. JC-1 (5,5',6,6'-tetrachloro-1, 1',3,3'-tetraethylbenzimidazolylcarbocyanine iodide) is a green-fluorescent probe that exists as a monomer at low concentrations or at low membrane potential. At higher concentrations or higher potentials, JC-1 forms red-fluorescent "J-aggregates" that exhibit a broad excitation spectrum and an emission maximum at ~590 nm. Thus, the emission of this cyanine dye can be used as a sensitive measure of mitochondrial membrane potential.

Astrocytes ectopically expressing Bcl2L12-V5 polypeptide exhibited a marked increase in the dissipated membrane potential (FIG. 4D). This result confirms that Bcl2L12 polypeptides promote necrosis.

Electron microscopy also confirmed that Bcl2L12 polypeptides promote necrosis. Briefly, INK4/Arf deficient astrocytes transfected with pBabe or a vector that ectopically expresses a Bcl2L12-V5 polypeptide were treated with STS (1 mM) for 16 hours or left untreated. After the incubation, the cellular morphology and mitochondrial fine structure of the cells were assessed using standard transmission electron microscopy as described elsewhere (St-Pierre et al., *J. Biol. Chem.*, 278(29):26597-603 (2003)). The pBabe control transfectants exhibited a typical apoptotic morphology with condensed cytoplasm and condensed chromatin being visible at the periphery of the nuclear envelope. The mitochondria were reduced in size while having preserved crystae structures. In contrast, astrocytes ectopically expressing Bcl2L12-V5 polypeptide exhibited no significant cytoplasmic condensation. In addition, the cells as well as their mitochondria appeared swollen, and nuclei were only partially fragmented without signs of chromatin condensation.

Example 7

Bcl2L12 Polypeptides are Pro-apoptotic in Lymphoid Cells

The role of Bcl2L12 polypeptides in lymphoid cells also was examined. First, the levels of Bcl2L12 polypeptide were measured in lymphoma cell lines. Lymphoma cell lines appeared to exhibit Bcl2L12 polypeptide expression. The levels of Bcl2L12 polypeptide expression, however, were lower than the levels observed in gliomas.

In addition, BJAB and SKW6.4 cells were co-transfected (1:3 ratio) with a vector encoding GFP and either an empty vector control or a vector encoding Bcl2L12-V5. After 24 hours, the transfected cells were stimulated with anti-CD95 or STS for 24 hours at different concentrations. The cells were analyzed by FACS. A gate was set only on GFP positive cells. Apoptosis was defined as an increase in sideward scatter and a decrease in forward scatter. SKW6.4 cells are type I B cells, while BJAB cells are type II B cells. Bcl2L12-V5 expression promoted apoptosis in both BJAB and SKW6.4 cells. These results suggest that Bcl2L12 polypeptides have pro-apoptotic activity in T or B lymphoid cells.

Example 8

Bcl2L12 Polypeptides bind p53 Polypeptides in vitro and in vivo

Caspase activation in general and Apaf-1 mediated caspase-9 activation in particular are signaling events that take place in the cytosol. In addition to its cytosolic localization, Bcl2L12-V5 polypeptides exhibited a nucleoplasm localization. In addition, immunofluorescence analysis revealed that Bcl2L12-V5 polypeptides colocalize with p53 polypeptides. To test whether p53 and Bcl2L12 polypeptides interact directly in vitro, GST fusion proteins were tested for binding to [$^{35}$S] labeled in vitro translated p53. GST-Bcl-x$_L$ associated weekly with p53, while a GST-Bcl2L12 polypeptide exhibited strong binding to p53 polypeptides as indicated by a nearly quantitative pulldown of radiolabeled p53. ¹⁄₁₀ of the in vitro translated material used for the pulldown was loaded as input.

To assess the specificity of this in vitro binding assay, mutant p53 polypeptides were tested for binding to a GST-Bcl2L12 polypeptide. These p53 mutants have single amino acid substitutions within the DNA binding domain and therefore do not bind DNA due to an altered tertiary structure. Their inability to bind DNA was verified by a luciferase assay using the dimerized DNA binding domain of p53 as a reporter. Both the V143R and V143P mutants exhibited reduced transcriptional activity when compared to wild type p53. In addition, both mutant p53 polypeptides exhibited significantly impaired binding to a GST-Bcl2L12 polypeptide. These results indicate that Bcl2L12 polypeptide specifically binds wild type p53, but does not exhibit association with p53 polypeptides containing point mutants that disrupt p53 ability to bind DNA.

To confirm the p53-Bcl2L12 polypeptide interaction in vivo, U87MG cells ectopically expressing HA-tagged p53 and V5-tagged Bcl2L12 polypeptides treated or untreated with STS (500 nM) for 8 hours were lysed in a 0.2% NP-40 containing lysis buffer, sonified, and subjected to an anti-HA immunoprecipitation and an anti-V5 immunoblot. The Bcl2L12-V5 polypeptide exhibited a weak association with p53 in non-apoptotic cells, but exhibited a more pronounced association with p53 in STS-treated cells. In a similar experiment, Ink4a/Arf deficient astrocytes ectopically expressing Bcl2L12-V5 were left untreated or γ-irradiated for 1 hour (10 Gy) and lysed as described above. The p53 polypeptide was immunoprecipitated from the lysates, and precipitates were analyzed using an anti-V5 immunoblot. In untreated and γ-irradiated cells, significant amounts of Bcl2L12-V5 polypeptide were associated with p53.

Example 9

Bcl2L12 Polypeptides Stabilize an Inactive p53 Species

Activation of the p53 transcription factor in response to a variety of cellular stresses, including DNA damage and oncogene activation, initiates a program of gene expression that blocks the proliferative expansion of damaged cells. To asses the effect of Bcl2L12 polypeptides on p53 mediated transcription, Ink4a/Arf deficient astrocytes ectopically expressing a Bcl2L12-V5 polypeptide were transfected with increasing amounts of nucleic acid encoding a p53 polypeptide and a luciferase construct bearing a dimerized p53 binding site in its promoter (PG13). Quantification of reporter activity (normalized to βGal activity) of transfectants expressing the Bcl2L12-V5 polypeptide revealed a marked decrease of transcriptional activity when compared to results using cells with the vector control. Using a mutant reporter construct containing a promoter sequence no longer recognized by p53 (M613) demonstrated the strict p53 dependence of this luciferase assay. XIAP, a caspase-9 inhibitor, had no effect on the transcriptional activity of p53.

To confirm the p53 modulatory activity of Bcl2L12 polypeptides, Ink4a/Arf deficient astrocytes stably expressing a Bcl2L12-V5 polypeptide were γ-irradiated (5 Gy or 10 Gy) for 0, 0.5, 1, 2, 3, 4, 5, 6, or 8 hours, lysed, and subjected to an anti-p53 immunoblot analysis. P53 was strongly induced in cells expressing the Bcl2L12-V5 polypeptide. The p53 expression was absent in control cells treated with 5 Gy of γ-irradiation and diminished in control cells treated with 10 Gy of γ-irradiation. The levels of Bax and Apaf-1, two p53 targets within the apoptosis signaling pathways, did not change.

To test whether p53 is transcriptionally active, p21 induction was followed in irradiated cells. Despite 50 fold higher expression levels, p21 expression was induced to similar amounts in cells expressing a Bcl2L12-V5 polypeptide when compared to the levels observed in cells receiving the control vector. These results indicate that Bcl2L12 polypeptides stabilize a transcriptionally inactive form of p53.

A northern blot for p53 in γ-irradiated Ink4a/Arf deficient astrocytic cultures expressing a Bcl2L12-V5 polypeptide was performed to test whether up-regulation of p53 in the presence of Bcl2L12-V5 is transcriptionally regulated. Astrocytes ectopically expressing a Bcl2L12-V5 polypeptide exhibited elevated mRNA levels for p53. These results indicate that Bcl2L12 regulates p53 expression (in part) on a transcriptional level.

The following experiment was performed to determine whether Bcl2L12 binds DNA. DNA cellulose was incubated with [$^{35}$S] labeled in vitro translated Bcl2L12, p53 (positive control), and caspase-9 (negative control). The amount of precipitated in vitro translated material was assessed by SDS-PAGE and autoradiography. Bcl2L12 polypeptide significantly bound DNA, indicating that it may function as a transcriptional activator.

Besides its unique domain structure, the Bcl2L12 polypeptide exhibits an atypical ability to block apoptosis at a post-mitochondrial level and to promote necrotic activity. In addition, Bcl2L12 may serve as a direct transcriptional activator of p53. Up-regulation of p53 can be followed by binding to Bcl2L12, thereby inhibiting p53's transcriptional activity. By keeping p53 in an inactive state, wild type p53 may behave like a mutant p53 sequestering into inactive tetramers. It has been demonstrated that p53's major function in glial cells is cell cycle arrest rather than apoptosis induction. Thus, Bcl2L12 may specifically target p53's growth arrest activity by repressing its transcriptional activity.

Example 10

Bcl2L12 Polypeptides Activate MAP Kinases

Ink4a/Arf deficient astrocytes transfected with a vector encoding either LacZ, Bcl2L12-V5, or EGFR* polypeptides were cultured for six days. Each day, the number of cells in each culture was determined. In addition, stably transfected cells were harvested and assessed for the phosphorylation of Erk1/2 (p44/p42). Astrocytes expressing Bcl2L12-V5 or EGFR* polypeptides exhibited more cell growth (about 3.8× $10^6$ and 5.0×$10^6$ cells on day 6, respectively) than astrocytes expressing LacZ (about 1.5×$10^6$ cells on day 6). In addition, the levels of Erk1 and Erk2 phosphorylation were higher in astrocytes expressing a Bcl2L12-V5 polypeptide when compared to the levels of Erk1 and Erk2 phosphorylation exhibited in control cells expressing LacZ. A similar result was observed in U87MG cells for Erk1 and Erk2 phosphorylation.

Example 11

Reducing Bcl2L12 Polypeptide Expression

Human glioma cell lines LNZ308, LN443, and LN382, which exhibit high, moderate, and low levels of Bcl2L12 mRNA as assessed by northern blot analysis respectively, were transfected with either control oligonucleotides or one of four siRNA oligonucleotides (50 µM each) using lipofectamine (Invitrogen). The sequence of the control oligonucleotide was as follows: 5'-CGAGAGUCCGACGAA-GACA-3' (SEQ ID NO:3). The four siRNA oligonucleotides were designated #1 (5'-AACUCCAC-CUAGAAGCCCU-3'; SEQ ID NO:4), #3 (5'-AAGAGCCAACAGACUUCCU-3'; SEQ ID NO:5), #4 (5'-AAGCUGGUCCGCCUGUCCU-3'; SEQ ID NO:6), and #5 (5'-UGGUGGAGCUGUUCU-GUAG-3'; SEQ ID NO:7). After 36 hours, Bcl2L12 mRNA expression was analyzed by semi-quantitative as well as quantitative real time PCR. The primers used to detect Bcl2L12 mRNA generated a 556 bp product and had the following sequence: Forward: 5'-GGAGACCGCAAGT-TGAGTGG-3' (SEQ ID NO:8) and Reverse: 5'-GTCATC-CCGGCTACAGAACA-3' (SEQ ID NO:9). The primers used to detect control mRNA (actin) generated a 838 bp product and had the following sequence: Forward: 5'-ATCTCGCAC-CACACCTTCTA-3' (SEQ ID NO:10) and Reverse: 5'-CGT-CATACTCCTGCTTGCTG-3' (SEQ ID NO:11).

Transfection of Bcl2L12-targeting siRNA, but not of control oligonucleotides, resulted in significant reduction of Bcl2L12 mRNA levels (FIG. 7A). In addition, the relative expression levels as quantified by real time PCR revealed a significant reduction in Bcl2L12 mRNA levels for cells transfected with the siRNA oligonucleotides.

Human glioma cell lines (LNZ308, LN443, and LN382) transfected with siRNA oligonucleotides were treated with different amounts of STS for 24 hours, and the percentage of DNA fragmentation was assessed. In all cell lines, siRNA-mediated knock down of Bcl2L12 mRNA resulted in a small, but significant sensitization of cells towards STS-induced apoptosis (FIG. 7B).

In another experiment, total cellular lysates of U87MG cells transfected with control siRNA, Bcl2L12-targeting siRNA #4, or Bcl2L12-targeting siRNA #5 were harvested 48 hours post transfection and subjected to western blot analysis using the anti-L12-1 antibody (1 µg/mL). Transfection of Bcl2L12-targeting siRNA, but not of control siRNA, resulted in a significant reduction in Bcl2L12 polypeptide levels (FIG. 10A).

LNZ308 and LN443 glioma cell lines transfected with control siRNA, Bcl2L12-targeting siRNA #4, or Bcl2L12-targeting siRNA #5 were treated with 0, 0.2, 0.5, 1.0, or 2.0 µM STS. DNA-fragmentation was assessed by quantifying sub-G1 peaks using FACS analysis. siRNA-mediated knockdown of Bcl2L12 polypeptide sensitized the glioma cell lines to STS-induced apoptosis. The percent DNA fragmentation in LNZ308 cells transfected with siRNA #4 and treated with 2.0 µM STS was significantly ($p=0.03$) greater than the percent DNA fragmentation in STS-treated (2.0 µM) cells expressing control siRNA (FIG. 10B). The maximum percent DNA fragmentation was about 30 percent, 45 percent, and 55 percent in LNZ308 cells transfected with control siRNA, siRNA #4, or siRNA #5, respectively, and treated with 2.0 µM STS (FIG. 10B). The percent DNA fragmentation in LN443 cells transfected with siRNA #4 and treated with 2.0 µM STS also was significantly ($p=0.003$) higher than the percent DNA fragmentation in STS-treated (2.0 µM) cells expressing control siRNA (FIG. 10C). The maximum percent DNA fragmentation was about 40 percent, 60 percent, and 75 percent in LN443 cells transfected with control siRNA, siRNA #4, or siRNA #5, respectively, and treated with 2.0 µM STS (FIG. 10C).

LNZ308 cells were transfected with control or siRNA oligonucleotide #5, and treated with STS for 24 hours. Subsequently, caspase activity was profiled using caspase-specific fluorogenic peptide substrates assessing the activity status of caspases 2, 3/7, 6, 8, and 9. Knockdown of Bcl2L12 expression resulted in enhanced caspase activity (FIG. 7C), reflecting the increase in DNA fragmentation observed in FIG. 7B.

LNZ308 cells were transfected with pcDNA3-GFP plus either pSHAG-A or pSHAG-B. After 24 hours, GFP positive cells were enriched using FACS-based sorting. The sorted cells were subjected to semi-quantitative RT-PCR for Bcl2L12 and actin mRNA. The level of Bcl2L12 mRNA was reduced in LNZ308 cells receiving pSHAG-A, but not in LNZ308 cells receiving pSHAG-B transfected cells (FIG. 7D). These results demonstrate that RNAi constructs can be designed to target Bcl2L12 such that cells transfected with the designed construct exhibit significant Bcl2L12 mRNA knockdown.

LNZ308 cells co-transfected with pcDNA3-GFP and either pSHAG-A or pSHAG-B were treated with 0.1 or 0.5 µM of STS for 24 hours, and DNA fragmentation was assessed. Again, RNAi-mediated knockdown of Bcl2L12 mRNA resulted in sensitization of LNZ308 cells towards STS-induced apoptosis (FIG. 7E).

Example 12

Reduction of Bcl2L12 Polypeptide Expression in Cancer Cells Diminishes Tumor Growth LNZ308 cells were transfected with pcDNA3-GFP and either pSHAG-A or pSHAG-B (control). Once transfected, the cells were sorted and the GFP-positive cells were injected intracranially into SCID mice to assess the effect of Bcl2L12 expression on tumor growth and tumor morphology in vivo. Substantial tumorigenicity of LNZ308 cells injected intracranially into immunocompromised SCID mice was described elsewhere (Ishii et al., *Brain Pathology*, 9:469-479 (1999)). Tumors developed after 8 weeks. Mice were sacrificed, and tumor morphology was assessed by histological analysis using H&E, Ki67, and TUNEL staining.

The tumor derived from pSHAG-A transfected cells was significantly smaller than the tumor established from pSHAG-B transfected cells (FIG. 7F, top panels). In addition, H&E (arrow heads) and TUNEL staining revealed an increased number of apoptotic cells in the tumor arising from pSHAG-A-transfected cells (FIG. 7F, top and bottom panels). The tumor established from pSHAG-A transfected cells exhibited about 44 TUNEL positive cells per high power field, while the tumor established from pSHAG-B transfected cells exhibited about 15 TUNEL positive cells per high power field. These results are consistent with the increased levels of apoptosis observed in vitro (FIG. 7E). The tumor derived from pSHAG-A transfected cells exhibited less Ki67 positive cells per high power field (about 108) than the number exhibited in the tumor established from pSHAG-B transfected cells (about 210), indicating that the tumor derived from pSHAG-A transfected cells exhibited a reduced level of proliferation (FIG. 7F, middle panels). Taken together, the results provided herein demonstrate that RNAi-mediated knockdown of Bcl2L12 expression can sensitize glioma cell lines to drug-induced apoptosis through increased caspase activation and can diminish tumor growth in vivo. In addition, these results establish that Bcl2L12 is a potent anti-apoptotic and pro-proliferative oncogene important for tumor growth in vivo.

Example 13

Generation of Polyclonal Anti-Bcl2L12 Antiserum

Polypeptides corresponding to amino acids 65 to 79 (CWRRPQVEWRRRRWGP) and 254 to 268 (CSRDDSS-RPSRAAPG) of Bcl2L12 were used to immunize rabbits (Zymed Laboratories/Invitrogen, Carlsbad, Calif.). Cys266 was substituted by Ala to prevent disulfide bridging. The first Cys residue was used to form a single point, site-directed conjugation to KLH. The polypeptide corresponding to amino acids 65 to 79 was used to produce anti-L12-1 antiserum, while the polypeptide corresponding to amino acids 255 to 268 was used to produce anti-L12-2 antiserum. Rabbits were immunized four times. The presence in the sera of antibodies having the ability to bind to the synthetic Bcl2L12 polypeptides was tested by ELISA. The anti-L12-1 antiserum was affinity purified.

The following experiments were performed to characterize the anti-Bcl2L12 polypeptide antibodies. U87MG cells stably expressing control or Bcl2L12-targeting shRNA (shL12-1) were subjected to deconvolution immunofluorescence microscopy using the anti-L12-2 antiserum. Cells were counterstained with DAPI. Deconvolved images were rotated along the z-axis to further document nuclear and cytosolic staining of Bcl2L12 polypeptides. Bcl2L12 polypeptide staining was nearly completely abolished in U87MG-shL12-1 cells, which exhibited a dramatic reduction in Bcl2L12 polypeptide level as assessed by western blot analysis.

Total cellular lysates of untreated and STS-treated (1 µM) U87MG cells were subjected to western blot analysis using the affinity-purified anti-L12-1 polyclonal antibody (1 µg/mL) and the anti-L12-2 antiserum (1:6000 dilution). Both the anti-L12-1 antibody and the anti-L12-2 antiserum detected one prominent 36 kDa band.

Recombinant GST-Bcl2L12 and lysates from control-, siRNA#4-, and siRNA#5-treated U87MG cells were subjected to western blot analysis using purified anti-L12-1 antibody (1 µg/mL). The anti-L12-1 antibody exhibited immunoreactivity with recombinant GST-Bcl2L12 polypeptides and with Bcl2L12 polypeptides in lysates of control siRNA-transfected U87MG cells, but not with lysates of cells expressing Bcl2L12-targeted siRNAs.

Recombinant GST-Bcl2L12 polypeptides; total cellular lysates of Ink4a/Arf deficient astrocytes ectopically expressing Bcl2L12-V5 polypeptides or containing pBabe; lysates of the glioma cell lines LNZ308, LN443, and LN382; and pre-bleed and anti-L12-2 immunoprecipitates of LNZ308 cells were subjected to western blot analysis using the polyclonal anti-L12-2 serum (1:6000 dilution). Tim23 served as a loading control. In parallel to cellular lysate preparation, total RNA was isolated from LNZ308, LN443, and LN382 cells, and Bcl2L12 mRNA levels were assessed by semiquantitative RT-PCR. Expression of β-actin was used as a control. Like the anti-L12-1 antibodies, the anti-L12-2 serum detected recombinant GST-Bcl2L12 polypeptides, ectopically expressed Bcl2L12-V5 polypeptides, and endogenous Bcl2L12 polypeptide in cellular lysates and immunoprecipitates of human glioma cell lines. The levels of Bcl2L12 polypeptide were observed to correspond to the levels of Bcl2L12 mRNA.

Example 14

Bcl2L12 Polypeptides Promote Cellular Transformation

The potential anti-oncogenic impact of Bcl2L12 polypeptide knockdown was assessed in the U87MG human glioma model system. For generation of U87MG cells stably expressing Bcl2L12-targeting shRNA, subconfluent Phoenix cells were transfected with pMD2.G containing VSV-G and shRNA (control, shL12-1, or shL12-2; Cat. Nos. RHS1764-9192649 and RHS1764-921071, Open Biosystems, Huntsville, Ala.) in pMSCV-puro-IRES-GFP (MSCV-PIG) mated with pMS2 (Open Biosystems). Nine µg of shRNA construct and 1 µg of pMD2.G-VSV-G were used. The cell culture medium was changed 16 hours post transfection. Supernants were harvested 24 hours later, sterile filtered, and added to U87MG with polybrene (5 µg/ml) for 48 hours. Cells were selected in puromycin (8 µg/ml) for 4 days. Bcl2L12 polypeptide expression was analyzed by western blotting using the anti-L12-1 antibody. Polypeptides were separated by 4-12% SDS-PAGE, transferred to Hybond PVDF membranes (Amersham Biosciences, Piscataway, N.J.), blocked for 1 hour with 5% milk in phosphate-buffered saline with 0.05% Tween 20 (PBS/Tween), washed with PBS/Tween, and incubated with the anti-L12-1 antiserum (1 µg/mL) in PBS/Tween with 5% milk. The blots were washed with PBS/Tween and developed with goat anti-rabbit IgG antibodies (1:10,000; Pierce Biotechnology, Rockford, Ill.) in PBS/Tween with 5% milk. After washing with PBS/Tween, the blots were developed with the Lumigen PS3 kit (Amersham) according to the manufacturer's protocol. U87MG cells stably expressing shL12-1 or shL12-2 exhibited significantly decreased Bcl2L12 polypeptide levels compared to U87MG cells expressing control shRNA (FIG. 11A).

U87MG cells expressing control or Bcl2L12-targeting hairpin RNAs were treated with 0.1, 0.2, 0.5, 1.0, or 3.0 µM STS (Sigma-Aldrich, Saint Louis, Mo.), and DNA fragmentation was assessed using FACS. Briefly, glioma cells were harvested, washed once with PBS, resuspended, and incubated for at least two hours at 4° C. in Nicoletti-buffer (0.1% (w/v) sodium citrate, 0.1% (v/v) triton X-100, 50 µg/ml propidium idodide). The percent DNA fragmentation was assessed by quantifying sub G1 peaks using FACS analysis. shRNA-mediated knockdown of Bcl2L12 polypeptide expression was observed to sensitize U87MG cells to STS-mediated apoptosis. U87MG cells expressing shL12-1 that were treated with 3.0 µM STS had a significantly (p=0.007) higher percent DNA fragmentation than STS-treated (3.0 µM) U87MG cells expressing control hairpin RNAs (FIG. 11B). The maximum percent DNA fragmentation was about 7.5 percent, 12 percent, and 20 percent in STS-treated (3.0 µM) cells expressing control hairpin RNAs, shL12-2, or shL12-1, respectively (FIG. 11B).

The potential anti-oncogenic impact of Bcl2L12 polypeptide knockdown was also assessed in vivo by performing xenotransplant tumor studies. U87MG cells ($2 \times 10^6$) were injected either subcutaneously (n=8 for each U87MG transfectant) or intracranially ($10^6$) into SCID mice (n=10 for each transfectant). Subcutaneously injected animals were watched closely for tumor development. Tumors were isolated 5-6 weeks post injection and weighed to determine tumor mass. For intracranial injections, cells were suspended in Hanks Buffered Salt Solution (10,000 cells/µL) and placed on ice. Six week old SCID mice were anesthetized with ketamine (60 mg/kg) and xylazine (7.5 mg/kg) and placed in the stereotactic frame using ear bars. A hole was bored in the skull 0.5 mm anterior and 3.0 mm lateral to the Bregma. Two mL of the cell suspension was injected into the right caudate nucleus 3-5 mm below the surface of the brain using a 26 gauge needle. The scalp was closed with 5.0 silk suture. Animals were followed daily for development of neurological deficits. Five animals per transfectant were used to generate survival curves to calculate $ID_{50}$ values. For pathological analyses (n=5), brains were fixed in 10% formaldehyde for 12 hours and processed for hematoxylin and eosin (H&E) by standard techniques. The entire brain was sectioned in 1-2 mm coronal blocks and submitted in one cassette for paraffin embedding to facilitate analysis of the whole brain. For immunohistochemical analysis, sections were prepared for BrdU, TUNEL, and active caspase-3/active caspase-7 staining (Calbiochem) according to standard protocols. The apoptotic index was determined by counting 700 nuclei per tumor section and calculating the fraction of nuclei that were TUNEL positive. Survival and histology were assessed in two independent cohorts.

Bcl2L12 polypeptide knockdown reduced subcutaneous tumor growth (FIG. 11C). The average weight of tumors derived from U87MG cells stably expressing control shRNA was about 0.45 gram, whereas tumors derived from U87MG cells stably expressing shL12-1 or shL12-2 had an average weight of about 0.15 gram (FIG. 11C).

Bcl2L12 polypeptide knockdown also extended survival following intracerebral injection. The $ID_{50}$ for mice injected with cells expressing shL12-1, shL12-2, or control shRNA was 28, 31, and 21 days, respectively (FIG. 11D). The difference in survival between the control cohort and the cohorts injected with cells expressing shL12-1 or shL12-2 was statistically significant ($p<0.05$).

Consistent with the decreased tumorigenic potential, Bcl2L12 polypeptide knockdown was associated with a modest decrease in proliferation and marked increase in apoptosis. The apoptotic index was approximately 0.012 for the control cohort, compared to approximately 0.03 for the shL12-1 cohort and approximately 0.028 for the shL12-2 cohort (FIG. 11E).

The tumors exhibited only slight enhancement in active caspase-3 staining and a dramatic increase in active caspase-7 staining. These results suggested that the tumor-promoting properties of Bcl2L12 polypeptides related, at least in part, to the ability of Bcl2L12 polypeptides to enhance tumor cell survival.

The combination of biological properties of Bcl2L12 polypeptides, namely cellular transformation, enhanced proliferation, subcloning efficiency, apoptosis resistance, and impact on xenograft tumor formation in vivo, indicated that Bcl2L12 polypeptide is an oncogene that sustains the viability and full malignant potential of established GBM cell lines.

Example 15

Interactions of Bcl2L12 Polypeptides with Post-mitochondrial Apoptosis Signaling Molecules To define further the molecular actions of Bcl2L12 polypeptides, the physical interactions with key post-mitochondrial apoptosis signaling molecules were assessed. Anti-L12-2 immunoprecipitates from lysates of LNZ308, U87MG, and 293T cells were subjected to western blot analysis for procaspases 7 and 3 and cytochrome c. Briefly, cells were lysed in IP buffer. Cleared supernatants were incubated with prebleed serum (8 µl) coupled to Protein A-sepharose 4B beads (Sigma) for 1 hour and subsequently with anti-L12-2 antiserum (8 µl) for 1 to 2 hours. For western blot analyses, polypeptides were separated by 4-12% SDS-PAGE, transferred to Hybond PVDF membranes (Amersham), blocked with 5% milk in phosphate-buffered saline with 0.05% Tween 20 (PBS/Tween) for 1 hour, washed with PBS/Tween and incubated with anti-cytochrome c antibodies (0.5 µg/ml; BD Pharmingen), anti-caspase-7 antibodies (0.5 µg/ml, BD Pharmingen), or anti-caspase-3 anitbodies (0.25 µg/ml, BD Transduction Laboratories) in PBS/Tween 20 with 5% milk. The blots were washed with PBS/Tween and developed with goat anti-rabbit IgG (1:10,000) or with goat anti-mouse antibodies (1:10,000) (Pierce) in 5% milk PBS/Tween. After washing with PBS/Tween, the blots were developed with the Lumigen PS3 kit (Amersham) following the manufacturer's protocol. 1/40 of the lysate used for the immunoprecipitation was loaded to quantify the amount of co-immunoprecipitated caspase-7. The immunoprecipitates revealed the presence of significant amounts of endogenous procaspase-7, but not procaspase-3 or the apoptosome component cytochrome c (FIG. 12A). Anti-L12-2 immunoprecipitates from control- and siRNA#5-treated U87MG cells were also subjected to western blot analysis for caspase-7. Bcl2L12 polypeptide knockdown resulted in a significant decrease in co-immunoprecipated pro-caspase-7, confirming the specificity profile of the anti-Bcl2L12 antisera (FIG. 12B).

To investigate the subcellular localization of Bcl2L12 polypeptide, caspase-7, and the potent caspase-7 inhibitor XIAP, LNZ308 cells were subjected to deconvolution microscopy using the anti-L12-2 antiserum, a monoclonal anti-caspase-7 antibody, and a monoclonal anti-XIAP antibody. Cells were grown on poly-D-lysine coated slides (Biocat, Becton Dickinson) and fixed with 2% paraformaldehyde for 20 min at room temperature. After fixation, the slides were washed three times with 50 nM $NH_4Cl$ in PBS for 3 min, permeabilized in ice-cold PBS with 0.3% Triton X-100 for 1 min, washed with PBS-Mg (PBS+1 mM $MgCl_2$), and incubated for 10 min in blocking solution (PBS, 5% BSA). The slides were incubated for 2 hours at room temperature or with the anti-L12-2 antiserum (1:600), anti-caspase-7 antibodies (1 µg/mL, BD Pharmingen), or anti-XIAP antibodies (1 µg/ml, BD Pharmingen). After washing with PBS-Mg, slides were incubated with secondary antibodies (10 µg/ml; Alexa Fluor 488 or 594, Molecular Probes) and DAPI (2 µg/ml) for 1 hour at room temperature, washed, and dehydrated in 100% ethanol. Slides were analyzed with an Olympus IX70 inverted fluorescence microscope at room temperature. Pictures were acquired using a CM350 CCD camera (Applied Precision) and 60X oil (Olympus PLAN-APO 1.40NA, 0.10 mm WD) or 100X oil (PLAN-APO 1.40NA, 0.10 mm WD) objectives. Forty cross-sections were taken and images were deconvolved using 10 cycles with the Ratio method as supplied with the DeltaVision software. The contrast was enhanced for some pictures using the same software. Green and red images were overlayed with DAPI staining. Deconvolved images for the Bcl2L12/caspase-7 staining were rotated by 90 degrees along the x-axis to analyze Bcl2L12 and caspase-7 distribution along the z-axis. In agreement with the demonstration of a physical association of Bcl2L12 polypeptides and caspase-7 polypeptides, Bcl2L12 polypeptides were observed to co-localize with caspase-7 polypeptides (FIG. 12C, left panel), as well as XIAP polypeptides (FIG. 12C, right panel), in nuclear and granular cytosolic structures.

To further investigate the interaction between Bcl2L12 polypeptides and caspase-7 polypeptides, recombinant GST-Bcl2L12 polypeptides and $(His)_6$-caspase-7 polypeptides were isolated by inducing BL21 bacteria with 1 µM IPTG (Sigma) for 6 hours (GST-Bcl2L12), or with 0.2 µM IPTG for 10 min (($His)_6$-caspase-7). Cells were lysed in Bac-Buffer (20 mM Tris-HCl, pH 8.0; 500 mM NaCl; 10% glycerol; 1% triton X-100; protease inhibitor cocktail (Roche)) and subsequently sonified for 1 min. Lysates were cleared by centrifugation (5,000×g) and incubated with GSH-sepharose 4B (Amersham) or Ni-NTA agarose (Qiagen) for 2 hrs at 4° C. $(His)_6$-caspase-7 polypeptides were eluted by incubating beads with 500 mM imidazol in 20 mM phosphate buffer/0.5 M NaCl (Amersham).

In vitro translated Bcl2L12-V5 polypeptides were incubated with $(His)_6$-caspase-7 or Ni-NTA beads (Qiagen), and precipitates were analyzed by autoradiography. 1/10 of the total in vitro translated product was used in the precipitation experiment. Recombinant caspase 7 polypeptides and Bcl2L12 polypeptides formed a complex (FIG. 12D), further validating the endogenous interaction. In vitro pull down assays using GST or GST-Bcl2L12 confirmed substantial association with the p20 subunit of caspase-7 polypeptide, but not with caspase-9 polypeptide (FIG. 12E), through direct polypeptide-polypeptide interaction (FIG. 12F). To perform these experiments, caspase-7 and caspase-9 polypeptides were in vitro-translated in the presence of $[^{35}S]$methionine using a TNT-coupled reticulocyte lysate system (Promega).

In vitro-translated caspase-9 polypeptides (C-9), caspase-7 polypeptides (C-7), a mixture of caspase-9 polypeptides and caspase-7 polypeptides (C-9+C-7), and in vitro processed caspase-7 polypeptides (see below) were incubated for two hours at 4° C. in IP buffer with 1 μg of GST or GST-Bcl2L12 polypeptides coupled to GSH beads. The beads were then washed three times with IP buffer and associated polypeptides were analyzed by 4-12% SDS-PAGE followed by autoradiography. For in vitro processing of caspase-7 polypeptides, 2.8 mM of recombinant active caspase-3 polypeptides (Pharmingen) were added to [$^{35}$S]-radiolabeled caspase-7 polypeptides for two hours at 37° C. in assay buffer (20 mM HEPES-KOH, 100 mM NaCl, 0.1% CHAPS, 10% sucrose, 10 mM DTT). To demonstrate that Bcl2L12 polypeptides and caspase-7 polypeptides interact directly, GST or GST-Bcl2L12 polypeptides coupled to GSH beads was incubated with increasing amounts of soluble recombinant (His)$_6$-tagged caspase-7 polypeptides and subjected to SDS-PAGE followed by Coommassie staining or western blotting using an anti-caspase-7 antibody. Due to immediate autoproteolysis of procaspase-7 polypeptides upon protein induction in bacteria, the proenzyme was nearly completely converted into the cleavage intermediate p32 and the active subunits p20 and p10 (FIG. 12F, lanes 1-3).

The observed Bcl2L12 polypeptide-caspase-7 polypeptide interaction prompted a more direct analysis of the role of caspase-7 polypeptide in governing apoptosis/necrosis processes in astrocytes. Ink4a/Arf deficient astrocytes were transfected with control siRNA or caspase-7-targeted siRNA (siRNA C7; Catalog No. M-057362-00, Dharmacon, Lafayette, Colo.) at a concentration of 100 nM using Oligofectamine (Invitrogen). Thirty-six hours post-transfection, cells were stimulated with STS (1 μM) for 0, 8, or 16 hours, and analyzed by transmission electron microscopy. The astrocyte cultures were fixed for 1 hour in a mixture of 2.5% glutaraldehyde, 1.25% paraformaldehyde, and 0.03% picric acid in 0.1 M sodium cacodylate buffer (pH 7.4), washed in 0.1 M cacodylate buffer, postfixed with 1% osmiumtetroxide/1.5% potassium ferrocyanide for 1 hour, washed in water, and stained in 1% aqueous uranyl acetate for 30 min followed by dehydration in grades of alcohol (5 min at 70%, 5 min at 90%, and 2×5 min at 100%). The samples were then infiltrated and embedded in TAAB Epon (Marivac Canada Inc.). Ultrathin sections (about 60 nm) were cut on a Reichert Ultracut-S microtome, picked up onto copper grids stained with uranylacetate and lead citrate, and examined in a JEOL 1200EX microscope.

Control cells stimulated with STS for 16 hours exhibited chromatin condensation and preserved plasma membrane integrity, whereas siRNA C7-transfected cultures exhibited profound plasma membrane desintegration and were characterized by the absence of chromatin condensation and swollen subcellular organelles. These results indicated that knockdown of caspase-7 polypeptide provoked a pronecrotic response in the context of apoptosis stimulation.

Quantification of apoptotic and necrotic cells using chromatin condensation and plasma membrane integrity as the two major hallmarks of these forms of cell death revealed a lower apoptotic index and an increased necrotic index in siRNA C7-transfected astrocytes compared to control siRNA-transfected cells (FIGS. 13A and 13B), recapitulating the cellular phenotype caused by ectopic expression of Bcl2L12 polypeptide. Approximately 50 cells per grid were counted on a total of 3 grids to assess the fraction of apoptotic (cells with chromatin condensation) and necrotic cells (cells with disintegrated plasma membrane). In contrast to Bcl2L12 polypeptide, knockdown of caspase-7 polypeptide did not affect caspase-3 polypeptide processing.

Example 16

Methods for Identifying Agents that Inhibit the Tumorigenic Activity of Bcl2L12 Polypeptides A high-throughput screen (HTS) was developed to identify agents (e.g., small organic compounds) that inhibit the tumorigenic activity of Bcl2L12 polypeptides. The HTS assay monitored the activation of caspase-7 polypeptides upon compound and stauropsorine (STS)-induced apoptosis using a highly sensitive fluorogenic substrate, (Z-DEVD)$_2$-Rh110, whose signal was monitored at excitation/emission 496 nm/520 nm (EnzoLyte™ Rh110 Caspase-7 Assay Kit (Anapsec)). Screening of chemical libraries was carried out. More than 100,000 compounds were screened. Briefly, Ink4a/Arf deficient astrocytes stably overexpressing Bcl2L12 polypeptide or control transfectants were plated into 384 well plates containing small molecules at a concentration of 5 μM. In parallel, the pan-specific kinase inhibitor staurosproine (STS) was added at a concentration of 1 μM as a positive control. The screening plates were read and the change of absorbency was scaled to non-activated cells and expressed as a fold change. Compounds sensitizing Bcl2L12 polypeptide expressing, but not pBabe control containing, astrocytes were used for a second round of validation using the same experimental setting. A class of agents was identified as candidate inhibitors.

OTHER EMBODIMENTS

It is to be understood that while the invention has been described in conjunction with the detailed description thereof, the foregoing description is intended to illustrate and not limit the scope of the invention, which is defined by the scope of the claims. Other aspects, advantages, and modifications are within the scope of the claims.

What is claimed is:

1. A method for identifying a compound that reduces Bcl2L12 polypeptide-induced inhibition of caspase-7 polypeptide activation, said method comprising:
   (a) contacting a sample with a test compound, wherein said sample comprises a caspase-7 polypeptide and a Bcl2L12 polypeptide, wherein said Bcl2L12 polypeptide comprises an amino acid sequence having a length of 150 or more amino acid residues with at least about 85 percent identity over said length to the amino acid sequence set forth in SEQ ID NO:1 or 2, and
   (b) determining whether or not the presence of said test compound increases caspase-7 polypeptide activation in said sample to a level greater than the level of caspase-7 polypeptide activation in a control sample lacking said test compound, wherein an increase in caspase-7 polypeptide activation in said sample indicates that said test compound is said compound that reduces Bcl2L12 polypeptide-induced inhibition of caspase-7 polypeptide activation.

2. The method of claim 1, wherein said sample comprises cells or a cell lysate.

3. The method of claim 2, wherein said cells are glioma cells, astrocytes, or melanocytes, and said cell lysate is a glioma cell lysate, an astrocyte cell lysate, or a melanocyte cell lysate.

4. The method of claim 2, wherein said cells comprise an isolated nucleic acid comprising a nucleic acid sequence encoding said Bcl2L12 polypeptide.

5. The method of claim 4, wherein said isolated nucleic acid comprises a constitutive promoter sequence or an inducible promoter sequence operably linked to said nucleic acid sequence encoding said Bcl2L12 polypeptide.

6. The method of claim 2, wherein said cells comprise an isolated nucleic acid comprising a nucleic acid sequence encoding said caspase-7 polypeptide.

7. The method of claim 6, wherein said isolated nucleic acid comprises a constitutive promoter sequence or an inducible promoter sequence operably linked to said nucleic acid sequence encoding said caspase-7 polypeptide.

8. The method of claim 1, wherein said sample comprises a cytochrome c polypeptide.

9. The method of claim 1, wherein said sample comprises dATP.

10. The method of claim 1, wherein said Bcl2L12 polypeptide is a human Bcl2L12 polypeptide.

11. The method of claim 1, wherein said Bcl2L12 polypeptide is a mouse Bcl2L12 polypeptide.

12. The method of claim 1, wherein said Bcl2L12 polypeptide lacks a BH2 domain sequence.

13. The method of claim 1, wherein said Bcl2L12 polypeptide comprises the sequence set forth in SEQ ID NO:1 or 2, or amino acid sequence 1 to 310, to 267, or 1 to 167 of the sequence set forth in SEQ ID NO:1.

14. The method of claim 1, wherein said sample comprises a polypeptide substrate for said caspase-7 polypeptide.

15. The method of claim 14, wherein said polypeptide substrate comprises a DEVD (SEQ ID NO:27) amino acid sequence.

16. The method of claim 14, wherein said polypeptide substrate is fluorogenic or colorogenic.

17. The method of claim 16, wherein said polypeptide substrate comprises aminomethylcoumarin.

18. The method of claim 16, wherein said step (b) comprises determining whether or not the presence of said test compound increases the level of fluorescence in said sample to a level greater than the level of fluorescence in said control sample lacking said test compound, wherein an increase in the level of fluorescence in said sample indicates that said test compound is said compound that reduces Bc12L12 polypeptide-induced inhibition of caspase-7 polypeptide activation.

19. The method of claim 1, wherein said step (b) comprises determining whether or not the presence of said test compound increases the level of a caspase-7 p20 polypeptide in said sample to a level greater than the level of a caspase-7 p20 polypeptide in said control sample lacking said test compound, wherein an increase in the level of a caspase-7 p20 polypeptide in said sample indicates that said test compound is said compound that reduces Bc12L12 polypeptide-induced inhibition of caspase-7 polypeptide activation.

20. The method of claim 1, wherein said step (b) comprises determining whether or not the presence of said test compound increases the level of a caspase-7 p10 polypeptide in said sample to a level greater than the level of a caspase-7 p10 polypeptide in said control sample lacking said test compound, wherein an increase in the level of a caspase-7 p10 polypeptide in said sample indicates that said test compound is said compound that reduces Bc12L12 polypeptide-induced inhibition of caspase-7 polypeptide activation.

* * * * *

UNITED STATES PATENT AND TRADEMARK OFFICE
CERTIFICATE OF CORRECTION

PATENT NO. : 7,595,158 B2  
APPLICATION NO. : 11/259640  
DATED : September 29, 2009  
INVENTOR(S) : Alex Stegh Page 1 of 1

It is certified that error appears in the above-identified patent and that said Letters Patent is hereby corrected as shown below:

Title Page, item [56] References Cited, Other Publications, Fujita et al. reference, please delete "Differ. ," and insert --Differ.,-- therefor;

Title Page, item [56] References Cited, Other Publications, Jiang et al. reference, please delete "203" and insert --2003-- therefor;

Column 60, line 64 (Claim 13), please delete "to 267," and insert --1 to 267,-- therefor.

Signed and Sealed this

Tenth Day of November, 2009

David J. Kappos  
*Director of the United States Patent and Trademark Office*

SEQUENCE LISTING

<160> NUMBER OF SEQ ID NOS: 26

<210> SEQ ID NO 1
<211> LENGTH: 334
<212> TYPE: PRT
<213> ORGANISM: Homo sapiens

<400> SEQUENCE: 1

```
Met Gly Arg Pro Ala Gly Leu Phe Pro Pro Leu Cys Pro Phe Leu Gly
1               5                  10                  15

Phe Arg Pro Glu Ala Cys Trp Glu Arg His Met Gln Ile Glu Arg Ala
            20                  25                  30

Pro Ser Val Pro Pro Phe Leu Arg Trp Ala Gly Tyr Arg Pro Gly Pro
        35                  40                  45

Val Arg Arg Arg Gly Lys Val Glu Leu Ile Lys Phe Val Arg Val Gln
    50                  55                  60

Trp Arg Arg Pro Gln Val Glu Trp Arg Arg Arg Trp Gly Pro Gly
65                  70                  75                  80

Pro Gly Ala Ser Met Ala Gly Ser Glu Glu Leu Gly Leu Arg Glu Asp
                85                  90                  95

Thr Leu Arg Val Leu Ala Ala Phe Leu Arg Arg Gly Glu Ala Ala Gly
            100                 105                 110

Ser Pro Val Pro Thr Pro Pro Arg Ser Pro Ala Gln Glu Glu Pro Thr
        115                 120                 125

Asp Phe Leu Ser Arg Leu Arg Arg Cys Leu Pro Cys Ser Leu Gly Arg
    130                 135                 140

Gly Ala Ala Pro Ser Glu Ser Pro Arg Pro Cys Ser Leu Pro Ile Arg
145                 150                 155                 160

Pro Cys Tyr Gly Leu Glu Pro Gly Pro Ala Thr Pro Asp Phe Tyr Ala
                165                 170                 175

Leu Val Ala Gln Arg Leu Glu Gln Leu Val Gln Glu Gln Leu Lys Ser
            180                 185                 190

Pro Pro Ser Pro Glu Leu Gln Gly Pro Pro Ser Thr Glu Lys Glu Ala
        195                 200                 205

Ile Leu Arg Arg Leu Val Ala Leu Leu Glu Glu Ala Glu Val Ile
    210                 215                 220

Asn Gln Lys Leu Ala Ser Asp Pro Ala Leu Arg Ser Lys Leu Val Arg
225                 230                 235                 240

Leu Ser Ser Asp Ser Phe Ala Arg Leu Val Glu Leu Phe Cys Ser Arg
                245                 250                 255

Asp Asp Ser Ser Arg Pro Ser Arg Ala Cys Pro Gly Pro Pro Pro
            260                 265                 270

Ser Pro Glu Pro Leu Ala Arg Leu Ala Leu Ala Met Glu Leu Ser Arg
        275                 280                 285

Arg Val Ala Gly Leu Gly Gly Thr Leu Ala Gly Leu Ser Val Glu His
    290                 295                 300

Val His Ser Phe Thr Pro Trp Ile Gln Ala His Gly Gly Trp Glu Gly
305                 310                 315                 320

Ile Leu Ala Val Ser Pro Val Asp Leu Asn Leu Pro Leu Asp
            325                 330

<210> SEQ ID NO 2
<211> LENGTH: 255
<212> TYPE: PRT
<213> ORGANISM: Mus musculus

<400> SEQUENCE: 2

Met Ala Gly Ser Glu Glu Leu Gly Leu Arg Glu Asp Thr Leu Lys Val
1               5                  10                  15

Leu Thr Ala Phe Leu Lys Arg Gly Glu Val Ala Gly Ser Pro Val Pro
            20                  25                  30

Thr Pro Pro Arg Ser Pro Ala Gln Glu Glu Thr Thr Asp Phe Leu Ser
        35                  40                  45
```

-continued

```
Arg Leu Arg Arg Cys Leu Pro Cys Pro Leu Gly Arg Gly Ala Pro Pro
 50                  55                  60

Thr Glu Ser Ser Arg Pro His Phe Leu Pro Leu Arg Pro Cys Tyr Gly
 65                  70                  75                  80

Ser Glu Pro Gly Pro Ala Ser Ser Glu Phe Tyr Ala Leu Val Ala Gln
                 85                  90                  95

Arg Leu Glu Gln Leu Val Gln Glu Gln Leu Lys Ser Pro Pro Ser Ser
            100                 105                 110

Glu Phe Gln Gly Pro Pro Thr Glu Lys Glu Ala Leu Leu Arg Arg
            115                 120                 125

Leu Val Ala Leu Leu Glu Glu Glu Ala Glu Val Ile Asn Gln Lys Leu
130                 135                 140

Ala Ser Asp Pro Ala Leu His Arg Lys Leu Ala Arg Leu Ser Ala Gly
145                 150                 155                 160

Ser Phe Ala Arg Leu Val Glu Leu Phe Ser Ser Arg Glu Ser Ser Ser
                165                 170                 175

Ser Pro Asn Cys Ser Ser Pro Ser Leu Pro Cys Pro Gly Pro Pro Pro
            180                 185                 190

Pro Ser Pro Asp Pro Leu Ala Arg Leu Ala Leu Ala Met Glu Leu Ser
            195                 200                 205

Arg Arg Val Ala Gly Leu Gly Gly Pro Leu Ala Asn Leu Ser Val Glu
210                 215                 220

His Val His Ser Phe Leu Pro Trp Val Gln Ala His Gly Gly Trp Ala
225                 230                 235                 240

Gly Ile Leu Ala Ser Ser Pro Val Asp Leu Asn Leu Pro Leu Asp
                245                 250                 255

<210> SEQ ID NO 3
<211> LENGTH: 19
<212> TYPE: DNA
<213> ORGANISM: Artificial Sequence
<220> FEATURE:
<223> OTHER INFORMATION: Oligonucleotide

<400> SEQUENCE: 3
cgagaguccg acgaagaca                                              19

<210> SEQ ID NO 4
<211> LENGTH: 19
<212> TYPE: DNA
<213> ORGANISM: Artificial Sequence
<220> FEATURE:
<223> OTHER INFORMATION: Oligonucleotide

<400> SEQUENCE: 4
aacuccaccu agaagcccu                                              19

<210> SEQ ID NO 5
<211> LENGTH: 19
<212> TYPE: DNA
<213> ORGANISM: Artificial Sequence
<220> FEATURE:
<223> OTHER INFORMATION: Oligonucleotide

<400> SEQUENCE: 5
aagagccaac agacuuccu                                              19

<210> SEQ ID NO 6
<211> LENGTH: 19
```

```
<212> TYPE: DNA
<213> ORGANISM: Artificial Sequence
<220> FEATURE:
<223> OTHER INFORMATION: Oligonucleotide

<400> SEQUENCE: 6
aagcuggucc gccuguccu                                              19

<210> SEQ ID NO 7
<211> LENGTH: 19
<212> TYPE: DNA
<213> ORGANISM: Artificial Sequence
<220> FEATURE:
<223> OTHER INFORMATION: Oligonucleotide

<400> SEQUENCE: 7
ugguggagcu guucuguag                                              19

<210> SEQ ID NO 8
<211> LENGTH: 20
<212> TYPE: DNA
<213> ORGANISM: Artificial Sequence
<220> FEATURE:
<223> OTHER INFORMATION: Oligonucleotide

<400> SEQUENCE: 8
ggagaccgca agttgagtgg                                             20

<210> SEQ ID NO 9
<211> LENGTH: 20
<212> TYPE: DNA
<213> ORGANISM: Artificial Sequence
<220> FEATURE:
<223> OTHER INFORMATION: Oligonucleotide

<400> SEQUENCE: 9
gtcatcccgg ctacagaaca                                             20

<210> SEQ ID NO 10
<211> LENGTH: 20
<212> TYPE: DNA
<213> ORGANISM: Artificial Sequence
<220> FEATURE:
<223> OTHER INFORMATION: Oligonucleotide

<400> SEQUENCE: 10
atctcgcacc acaccttcta                                             20

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide

<400> SEQUENCE: 11
cgtcatactc ctgcttgctg                                             20

<210> SEQ ID NO 12
<211> LENGTH: 31
<212> TYPE: DNA
<213> ORGANISM: Artificial Sequence
<220> FEATURE:
<223> OTHER INFORMATION: Oligonucleotide

<400> SEQUENCE: 12
```

```
gtttgtacga gttcagtgga ggagaccgca a                                          31
```

<210> SEQ ID NO 13
<211> LENGTH: 31
<212> TYPE: DNA
<213> ORGANISM: Artificial Sequence
<220> FEATURE:
<223> OTHER INFORMATION: Oligonucleotide

<400> SEQUENCE: 13

```
gttgagtgga ggaggcggcg gtggggcccc g                                          31
```

<210> SEQ ID NO 14
<211> LENGTH: 8
<212> TYPE: PRT
<213> ORGANISM: Artificial Sequence
<220> FEATURE:
<223> OTHER INFORMATION: Fragment of Bcl2L12

<400> SEQUENCE: 14

Pro Gly Pro Pro Pro Pro Ser Pro
 1               5

<210> SEQ ID NO 15
<211> LENGTH: 50
<212> TYPE: PRT
<213> ORGANISM: Artificial Sequence
<220> FEATURE:
<223> OTHER INFORMATION: Fragment of BCL2L12

<400> SEQUENCE: 15

Gly Pro Ala Thr Pro Asp Phe Tyr Ala Leu Val Ala Gln Arg Leu Glu
 1               5                   10                  15

Gln Leu Val Gln Glu Gln Leu Lys Ser Pro Ser Pro Glu Leu Gln
            20                  25                  30

Gly Pro Pro Ser Thr Glu Lys Glu Ala Ile Leu Arg Arg Leu Val Ala
        35                  40                  45

Leu Leu
    50

<210> SEQ ID NO 16
<211> LENGTH: 49
<212> TYPE: PRT
<213> ORGANISM: Artificial Sequence
<220> FEATURE:
<223> OTHER INFORMATION: Fragment of IRF3

<400> SEQUENCE: 16

Asp Pro His Asp Pro His Lys Ile Tyr Glu Phe Val Asn Ser Gly Val
 1               5                   10                  15

Gly Asp Phe Ser Gln Pro Asp Thr Ser Pro Asp Thr Asn Gly Gly Gly
            20                  25                  30

Ser Thr Ser Asp Thr Gln Glu Asp Ile Leu Asp Glu Leu Leu Gly Asn
        35                  40                  45

Met

<210> SEQ ID NO 17
<211> LENGTH: 14
<212> TYPE: PRT
<213> ORGANISM: Artificial Sequence
<220> FEATURE:
<223> OTHER INFORMATION: Fragment of Bcl2L12

<400> SEQUENCE: 17

```
Trp Ile Gln Ala His Gly Gly Trp Glu Gly Ile Leu Ala Val
1               5                   10
```

<210> SEQ ID NO 18
<211> LENGTH: 14
<212> TYPE: PRT
<213> ORGANISM: Artificial Sequence
<220> FEATURE:
<223> OTHER INFORMATION: Fragment of Bcl-2

<400> SEQUENCE: 18

```
Trp Ile Gln Asp Asn Gly Gly Trp Asp Ala Phe Val Glu Leu
1               5                   10
```

<210> SEQ ID NO 19
<211> LENGTH: 14
<212> TYPE: PRT
<213> ORGANISM: Artificial Sequence
<220> FEATURE:
<223> OTHER INFORMATION: Fragment of Bax

<400> SEQUENCE: 19

```
Trp Ile Gln Asp Gln Gly Gly Trp Val Arg Leu Leu Ser Tyr
1               5                   10
```

<210> SEQ ID NO 20
<211> LENGTH: 14
<212> TYPE: PRT
<213> ORGANISM: Artificial Sequence
<220> FEATURE:
<223> OTHER INFORMATION: Fragment of Boo

<400> SEQUENCE: 20

```
Trp Leu Gln Ala Gln Gly Gly Trp Asp Gly Phe Cys His Phe
1               5                   10
```

<210> SEQ ID NO 21
<211> LENGTH: 14
<212> TYPE: PRT
<213> ORGANISM: Artificial Sequence
<220> FEATURE:
<223> OTHER INFORMATION: Fragment of Bcl-x

<400> SEQUENCE: 21

```
Trp Ile Gln Glu Asn Gly Gly Trp Asp Thr Phe Val Glu Leu
1               5                   10
```

<210> SEQ ID NO 22
<211> LENGTH: 14
<212> TYPE: PRT
<213> ORGANISM: Artificial Sequence
<220> FEATURE:
<223> OTHER INFORMATION: Fragment of Bcl-w

<400> SEQUENCE: 22

```
Trp Ile His Ser Ser Gly Gly Trp Ala Glu Phe Thr Ala Leu
1               5                   10
```

<210> SEQ ID NO 23
<211> LENGTH: 14
<212> TYPE: PRT
<213> ORGANISM: Artificial Sequence
<220> FEATURE:
<223> OTHER INFORMATION: Fragment of A1/BLF-1

<400> SEQUENCE: 23

```
Trp Ile Arg Gln Asn Gly Gly Trp Glu Asn Gly Phe Val Lys
1               5                   10

<210> SEQ ID NO 24
<211> LENGTH: 14
<212> TYPE: PRT
<213> ORGANISM: Artificial Sequence
<220> FEATURE:
<223> OTHER INFORMATION: Fragment of BHRF1

<400> SEQUENCE: 24

Trp Ile His Gln Gln Gly Gly Pro Ser Leu Leu Arg Gly Asn
1               5                   10

<210> SEQ ID NO 25
<211> LENGTH: 14
<212> TYPE: PRT
<213> ORGANISM: Artificial Sequence
<220> FEATURE:
<223> OTHER INFORMATION: Fragment of NR-13

<400> SEQUENCE: 25

Trp Met Glu Glu His Gly Gly Trp Asp Gly Phe Cys Arg Phe
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Fragment of LMW5-HR

<400> SEQUENCE: 26

Trp Met Ile Ser His Gly Gly Gln Glu Glu Phe Leu Ala Phe
1               5                   10
```